(12) United States Patent
Kurihara et al.

(10) Patent No.: US 10,868,258 B2
(45) Date of Patent: Dec. 15, 2020

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Miki Kurihara, Kanagawa (JP); Hideko Yoshizumi, Kanagawa (JP); Hiromitsu Kido, Kanagawa (JP); Tatsuyoshi Takahashi, Kanagawa (JP); Satoshi Seo, Kanagawa (JP)

(73) Assignee: Semiconductor Energy Laboratory Co., Ltd.

( * ) Notice: Subject to any disclaimer, the term of this patent is extended or adjusted under 35 U.S.C. 154(b) by 214 days.

(21) Appl. No.: 15/843,870

(22) Filed: Dec. 15, 2017

(65) Prior Publication Data

US 2018/0182976 A1    Jun. 28, 2018

(30) Foreign Application Priority Data

Dec. 23, 2016  (JP) ................................. 2016-250190

(51) Int. Cl.
| | | |
|---|---|---|
| *H01L 51/50* | (2006.01) | |
| *H01L 51/00* | (2006.01) | |
| *C07D 491/048* | (2006.01) | |
| *C07D 495/04* | (2006.01) | |

(52) U.S. Cl.
CPC ...... *H01L 51/0072* (2013.01); *C07D 491/048* (2013.01); *C07D 495/04* (2013.01); *H01L 51/0052* (2013.01); *H01L 51/0054* (2013.01); *H01L 51/0071* (2013.01); *H01L 51/0073* (2013.01); *H01L 51/0074* (2013.01); *H01L 51/0085* (2013.01); *H01L 51/508* (2013.01); *H01L 51/5016* (2013.01)

(58) Field of Classification Search
None
See application file for complete search history.

(56) References Cited

U.S. PATENT DOCUMENTS

| 6,602,618 B2 * | 8/2003 | Watanabe ........... H01L 51/0081 313/504 |
|---|---|---|
| 9,553,274 B2 | 1/2017 | Xia et al. |
| 2010/0231568 A1 * | 9/2010 | Yamashita ........... G09G 3/3233 345/211 |
| 2013/0140549 A1 | 6/2013 | Xia et al. |
| 2014/0131665 A1 | 5/2014 | Xia et al. |
| 2014/0291645 A1 | 10/2014 | Inoue et al. |

(Continued)

FOREIGN PATENT DOCUMENTS

| EP | 2 826 781 A1 | 1/2015 |
|---|---|---|
| JP | 2011-084531 A | 4/2011 |

(Continued)

*Primary Examiner* — Gregory D Clark
(74) *Attorney, Agent, or Firm* — Husch Blackwell LLP

(57) ABSTRACT

A novel organic compound is provided. Moreover, a light-emitting element with high emission efficiency and a long lifetime is provided. A novel organic compound having a bicarbazole skeleton and a benzofuropyrimidine skeleton or a benzothienopyrimidine skeleton that includes at least one condensed ring or two condensed rings is provided. Moreover, a light-emitting element including the organic compound is provided.

12 Claims, 25 Drawing Sheets

(56) References Cited

U.S. PATENT DOCUMENTS

| | | |
|---|---|---|
| 2015/0021555 A1 | 1/2015 | Kwong et al. |
| 2015/0021556 A1* | 1/2015 | Xia .................... H01L 51/0071 257/40 |
| 2016/0093818 A1 | 3/2016 | Inoue et al. |
| 2016/0336517 A1 | 11/2016 | Hirose et al. |
| 2016/0351829 A1 | 12/2016 | Hosoumi et al. |
| 2016/0351833 A1 | 12/2016 | Hosoumi et al. |
| 2017/0069852 A1 | 3/2017 | Kanamoto et al. |
| 2017/0170409 A1 | 6/2017 | Xia et al. |
| 2017/0186971 A1 | 6/2017 | Kanamoto et al. |

FOREIGN PATENT DOCUMENTS

| | | |
|---|---|---|
| JP | 2013-536196 | 9/2013 |
| JP | 2014-209611 A | 11/2014 |
| KR | 2015-0133998 A | 12/2015 |

* cited by examiner

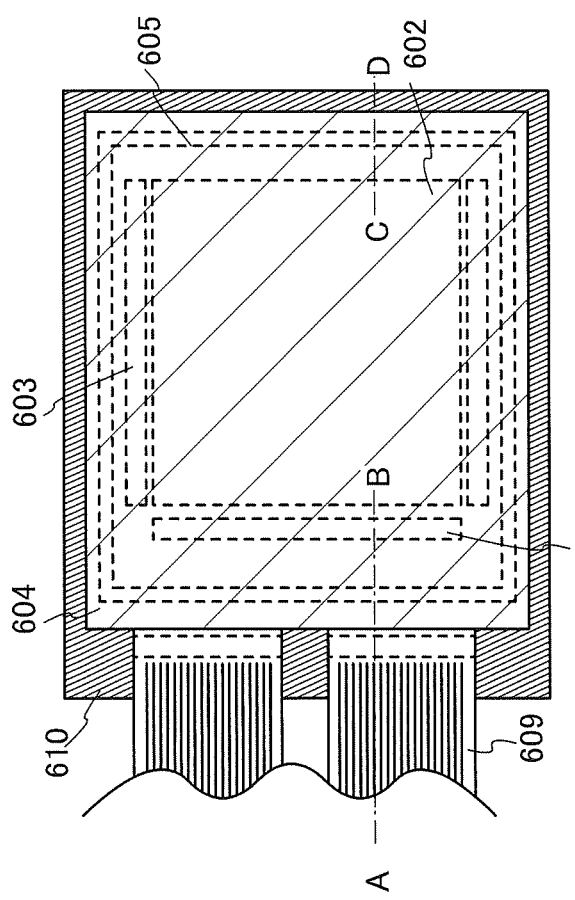
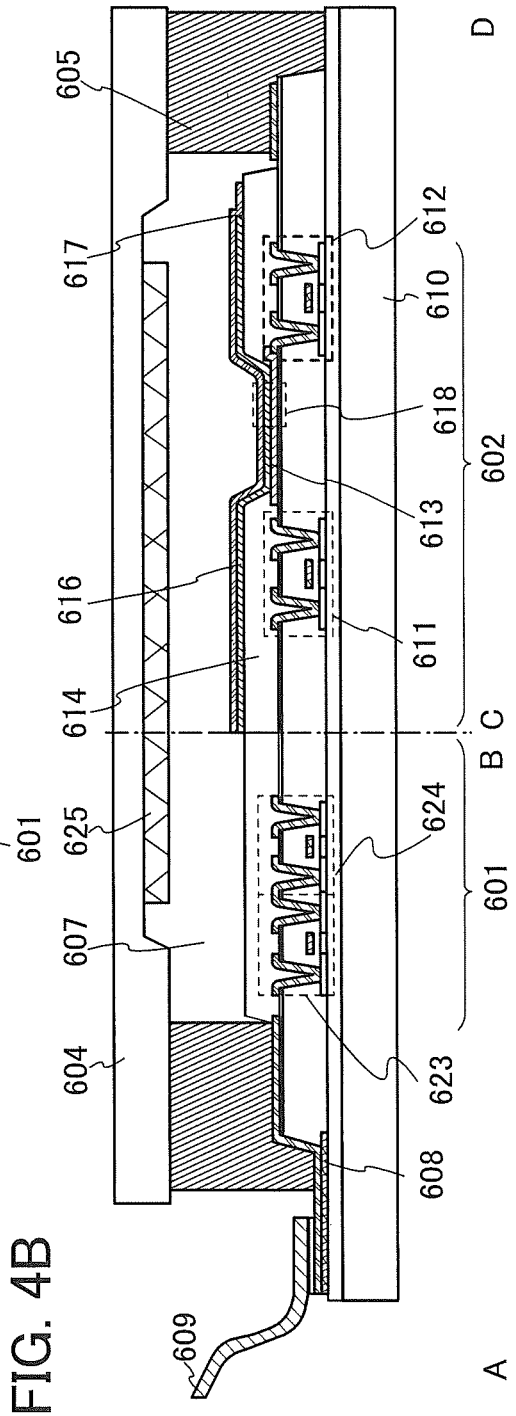
FIG. 4A
FIG. 4B

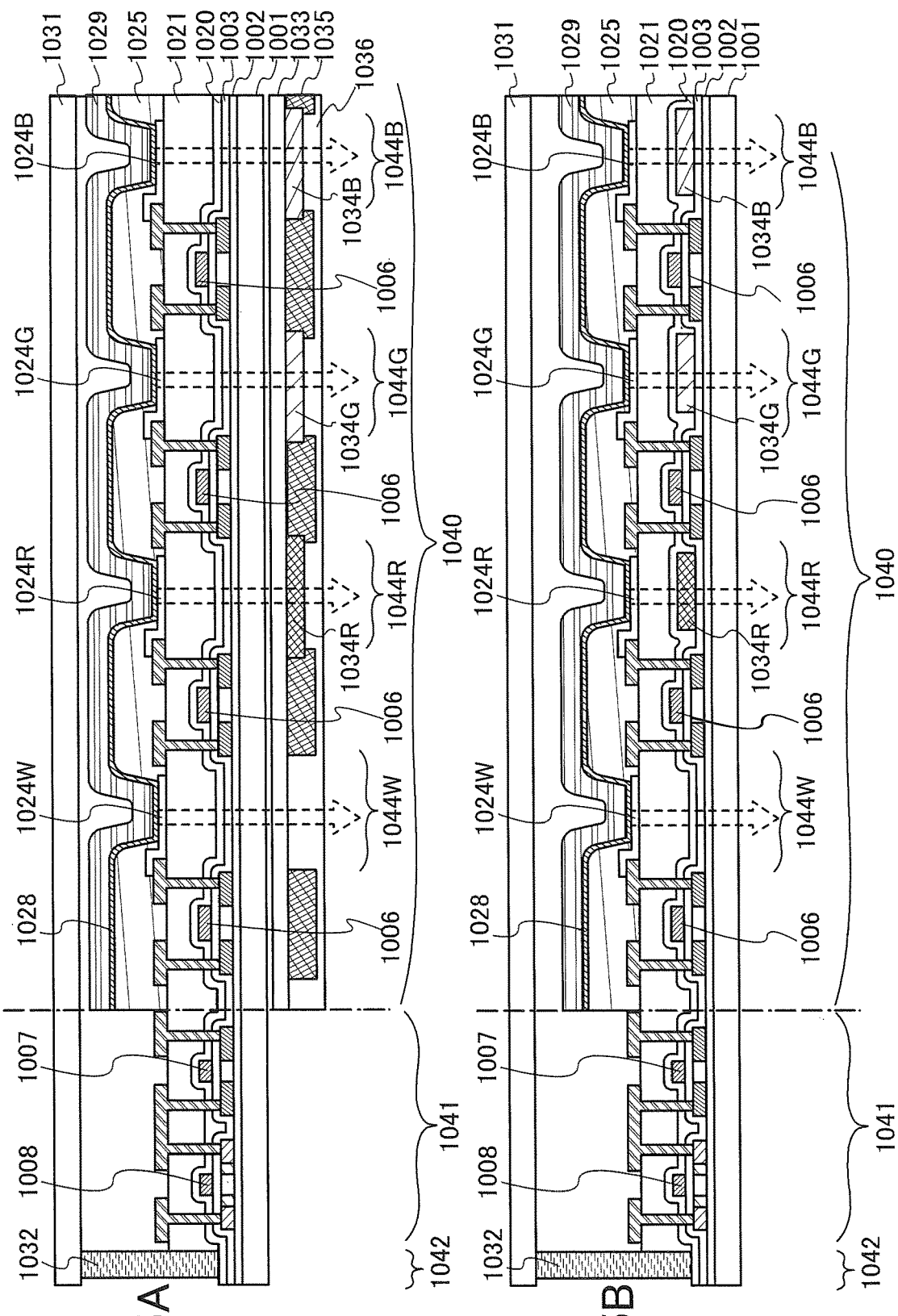

ORGANIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a novel organic compound. One embodiment of the present invention relates to a benzofuro[3,2-d]pyrimidine compound or a benzothieno[3,2-d]pyrimidine compound that has a bicarbazole skeleton and a condensed ring. In addition, one embodiment of the present invention relates to a light-emitting element, a light-emitting device, an electronic device, and a lighting device each of which includes the organic compound.

Note that one embodiment of the present invention is not limited to the above technical field. One embodiment of the present invention relates to an object, a method, or a manufacturing method. The present invention relates to a process, a machine, manufacture, or a composition of matter. In particular, one embodiment of the present invention relates to a semiconductor device, a light-emitting device, a display device, a lighting device, a light-emitting element, or a manufacturing method thereof. In addition, one embodiment of the present invention relates to a novel method for synthesizing a benzofuropyrimidine compound or a benzothienopyrimidine compound that has a bicarbazole skeleton and a condensed ring. Thus, specific examples of one embodiment of the present invention disclosed in this specification include a light-emitting element, a light-emitting device, an electronic device, and a lighting device, each of which includes the organic compound, and a manufacturing method thereof.

2. Description of the Related Art

Light-emitting elements (organic EL elements) including organic compounds and utilizing electroluminescence (EL) have been put to more practical use. In the basic structure of such light-emitting elements, an organic compound layer containing a light-emitting material (an EL layer) is interposed between a pair of electrodes. Carriers are injected by application of voltage to the element, and recombination energy of the carriers is used, whereby light emission can be obtained from the light-emitting material.

The light-emitting elements are self-luminous elements and thus have advantages such as high visibility and no need for backlight when used as pixels of a display, and are suitable as flat panel display elements. Displays including such light-emitting elements are also highly advantageous in that they can be thin and lightweight. Moreover, such a light-emitting element also has a feature that response speed is extremely fast.

Since light-emitting layers of such light-emitting elements can be successively formed two-dimensionally, planar light emission can be achieved. This feature is difficult to obtain with point light sources typified by incandescent lamps and LEDs or linear light sources typified by fluorescent lamps. Furthermore, light emission from an organic compound can be light emission which does not include UV light by selecting a material; thus, light-emitting elements also have great potential as planar light sources used in lighting devices and the like.

Displays or lighting devices including organic EL elements can be suitably used for a variety of electronic devices as described above; thus, research and development of light-emitting elements have progressed for higher efficiency or longer element lifetimes. In particular, an organic compound is mainly used in an EL layer and greatly affects an improvement in the characteristics of the light-emitting element. For this reason, a variety of novel organic compounds have been developed.

The lifetime and properties of a light-emitting element including an organic compound are greatly affected by the properties of a host material or an electron-transport material in some cases.

As host materials, substances having various skeletons are used. Various bicarbazole compounds have been reported because a bicarbazole compound particularly has a high triplet excitation level (T1 level). Note that it can be said that a light-emitting element using a bicarbazole compound have not sufficiently satisfy advanced requirements for various characteristics including efficiency and durability yet (e.g., Patent Document 1 and Patent Document 2).

REFERENCE

Patent Document

[Patent Document 1] Japanese Published Patent Application No. 2014-209611

[Patent Document 2] Japanese Translation of PCT International Application No. 2013-536196

SUMMARY OF THE INVENTION

In view of the above, an object of one embodiment of the present invention is to provide a novel organic compound. In particular, an object is to provide a novel heteroaromatic ring compound. Another object of one embodiment of the present invention is to provide a novel organic compound having an electron-transport property. Another object of one embodiment of the present invention is to provide a light-emitting element with a long lifetime. Another object of one embodiment of the present invention is to provide a light-emitting element with high emission efficiency. Another object of one embodiment of the present invention is to provide a light-emitting element with low driving voltage.

Another object of one embodiment of the present invention is to provide a light-emitting element, a light-emitting device, and an electronic device each having high reliability. Another object of one embodiment of the present invention is to provide a light-emitting element, a light-emitting device, and an electronic device each with low power consumption.

Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is an organic compound represented by General Formula (G0) shown below.

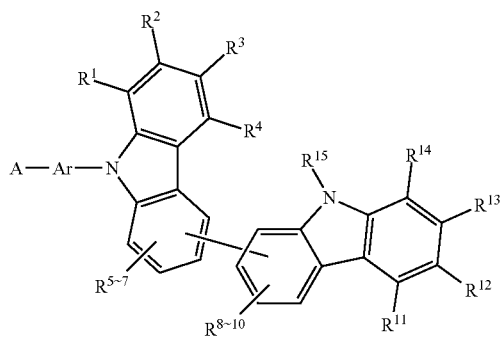

(G0)

In General Formula (G0), A represents a substituted or unsubstituted benzofuro[3,2-d]pyrimidine skeleton including at least a substituent including one condensed ring or two condensed rings or a substituted or unsubstituted benzothieno[3,2-d]pyrimidine skeleton including at least a substituent including one condensed ring or two condensed rings; each of $R^1$ to $R^{15}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

In the above structure, Ar is preferably bonded to the 4-position of the benzofuro[3,2-d]pyrimidine skeleton or the benzothieno[3,2-d]pyrimidine skeleton.

Another embodiment of the present invention is an organic compound represented by General Formula (G1) shown below.

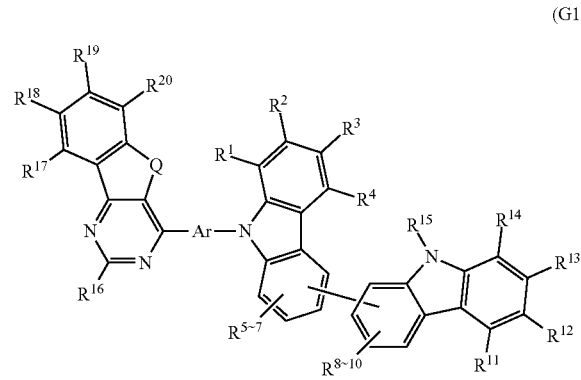

(G1)

In General Formula (G1), Q represents oxygen or sulfur; each of $R^1$ to $R^{15}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; any one of $R^{16}$ to $R^{20}$ represents a substituent including one condensed ring or two condensed rings and each of the others independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

Another embodiment of the present invention is an organic compound represented by General Formula (G2) shown below.

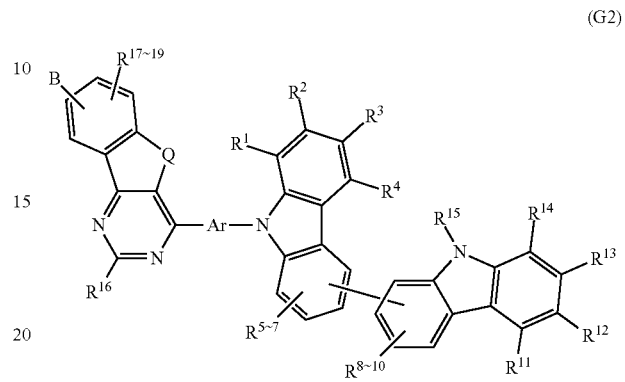

(G2)

In General Formula (G2), Q represents oxygen or sulfur; each of $R^1$ to $R^{19}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; Ar represents a substituted or unsubstituted arylene group having 6 to 25 carbon atoms, or a single bond; and B represents a substituent including one condensed ring or two condensed rings.

Another embodiment of the present invention is an organic compound represented by General Formula (G3) shown below.

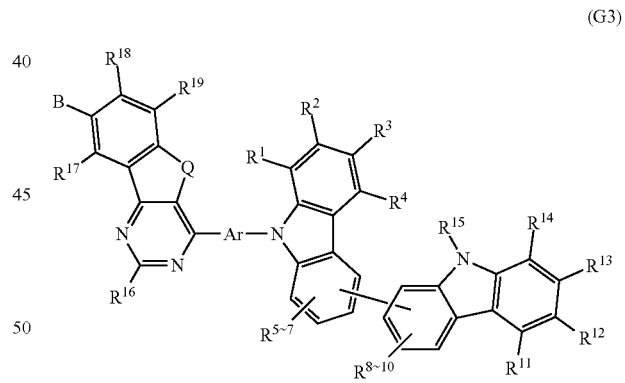

(G3)

In General Formula (G3), Q represents oxygen or sulfur; each of $R^1$ to $R^{19}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; Ar represents a substituted or unsubstituted arylene group having 6 to 25 carbon atoms, or a single bond; and B represents a substituent including one condensed ring or two condensed rings.

In the above structure, the number of carbon atoms in the condensed ring is preferably 10 to 20.

In the above structure, the condensed ring preferably has any one of a carbazole skeleton, a dibenzothiophene skeleton, and a dibenzofuran skeleton.

Another embodiment of the present invention is an organic compound represented by General Formula (G4) shown below.

(G4)

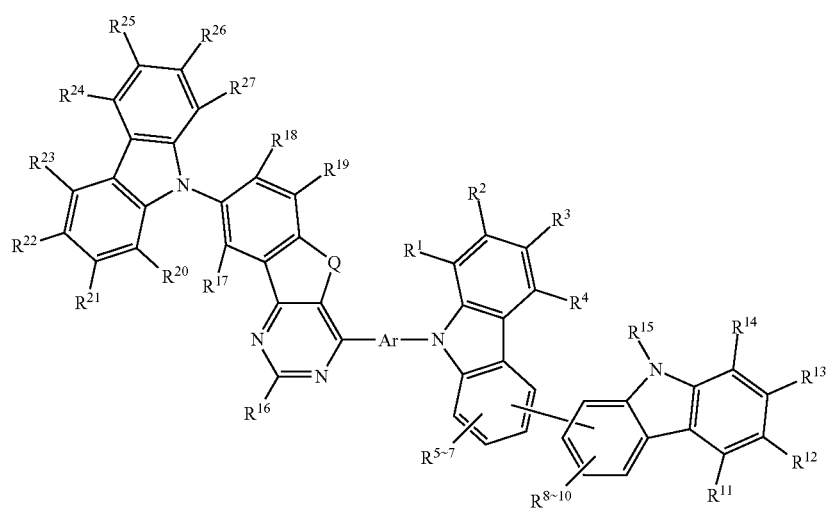

In General Formula (G4), Q represents oxygen or sulfur; each of $R^1$ to $R^{27}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

Another embodiment of the present invention is an organic compound represented by General Formula (G5) shown below.

In General Formula (G5), Q represents oxygen or sulfur; each of $R^1$ to $R^{34}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

Another embodiment of the present invention is an organic compound represented by General Formula (G6) shown below.

(G5)

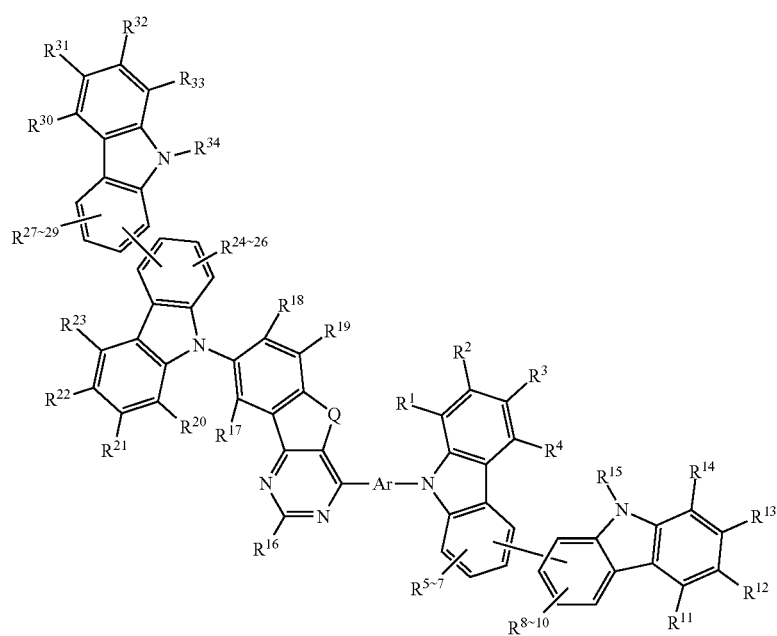

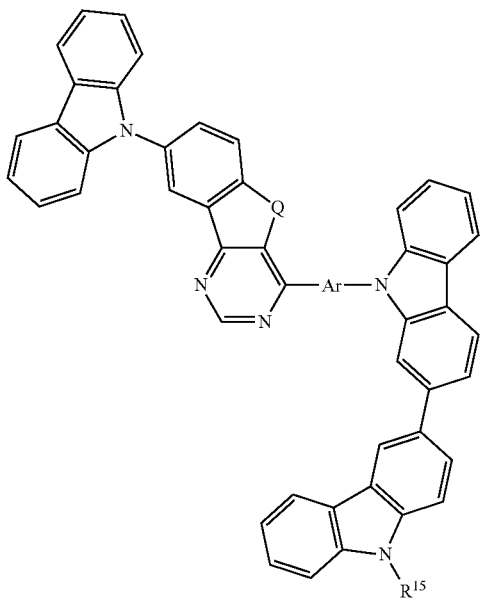

(G6)

In General Formula (G6), Q represents oxygen or sulfur; $R^{15}$ represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

Another embodiment of the present invention is an organic compound represented by General Formula (G7) shown below.

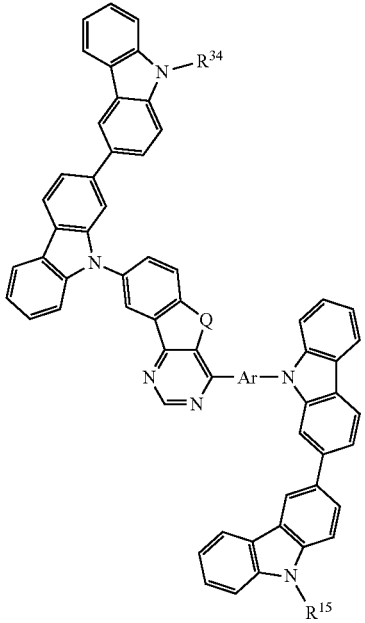

(G7)

In General Formula (G7), Q represents oxygen or sulfur; each of $R^{15}$ and $R^{34}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

Another embodiment of the present invention is a light-emitting element containing any of the above-described organic compounds.

The light-emitting element in the above embodiment includes an EL layer between an anode and a cathode. The EL layer includes at least one of a light-emitting layer, a hole-transport layer, a hole-injection layer, an electron-transport layer, and an electron-injection layer. Note that the EL layer may include another functional layer.

In the above structure, the light-emitting layer preferably contains a light-emitting material.

Another embodiment of the present invention is a display device including the light-emitting element having any of the above structures, and at least one of a color filter and a transistor. Another embodiment of the present invention is an electronic device including the display device, and at least one of a housing and a touch sensor. Another embodiment of the present invention is a lighting device including the light-emitting element having any of the above-described structures, and at least one of a housing and a touch sensor. The category of one embodiment of the present invention includes not only a light-emitting device including a light-emitting element but also an electronic device including a light-emitting device. Accordingly, a light-emitting device in this specification refers to an image display device or a light source (including a lighting device). A display module in which a connector such as a flexible printed circuit (FPC) or a tape carrier package (TCP) is connected to a light-emitting element, a display module in which a printed wiring board is provided on the tip of a TCP, and a display module in which an integrated circuit (IC) is directly mounted on a light-emitting element by a chip on glass (COG) method are also embodiments of the present invention.

One embodiment of the present invention can provide a novel organic compound. In particular, a novel heteroaromatic ring compound can be provided. Another embodiment of the present invention can provide a novel organic compound having an electron-transport property. Another embodiment of the present invention can provide a light-emitting element with a long lifetime. Another embodiment of the present invention can provide a light-emitting element with high emission efficiency. Another embodiment of the present invention can provide a light-emitting element with low driving voltage. Another embodiment of the present invention can provide a light-emitting element, a light-emitting device, and an electronic device each having high reliability. Another embodiment of the present invention can provide a light-emitting element, a light-emitting device, and an electronic device each with low power consumption.

Note that the description of these effects does not disturb the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

In the accompanying drawings:

FIGS. 4A and 4B are conceptual diagrams of an active matrix light-emitting device of one embodiment of the present invention;

FIGS. 5A and 5B are conceptual diagrams of an active matrix light-emitting device of one embodiment of the present invention;

DETAILED DESCRIPTION OF THE INVENTION

Figure 1A:
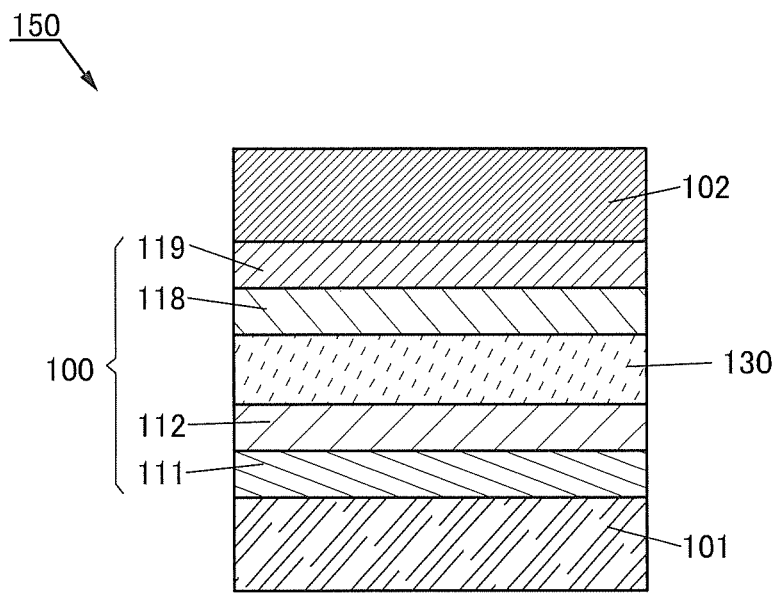
FIGS. 1A to 1C are schematic cross-sectional views illustrating a light-emitting element of one embodiment of the present invention and a schematic diagram showing the correlation of energy levels in a light-emitting layer.

Hereinafter, embodiments of the present invention will be described. Note that it is easily understood by those skilled in the art that modes and details disclosed herein can be modified in various ways without departing from the spirit and scope of the present invention. Therefore, the invention disclosed in this specification should not be interpreted as being limited to the description in the embodiments.

Note that in each drawing described in this specification, the size, the thickness, and the like of components such as an anode, an EL layer, an intermediate layer, and a cathode are exaggerated for clarity in some cases. Therefore, the sizes of the components are not limited to the sizes in the drawings and relative sizes between the components.

Note that the ordinal numbers such as "first", "second", and "third" in this specification and the like are used for convenience and do not denote the order of steps, the positional relation, or the like. Therefore, for example, description can be made even when "first" is replaced with "second" or "third", as appropriate. In addition, the ordinal numbers in this specification and the like are not necessarily the same as those which specify one embodiment of the present invention.

Note that in structures of the present invention described in this specification and the like, the same portions or portions having similar functions are denoted by common reference numerals in different drawings, and descriptions thereof are not repeated. Further, the same hatching pattern is applied to portions having similar functions, and the portions are not especially denoted by reference numerals in some cases.

In this specification, color is defined by three aspects of hue (corresponding to the wavelength of light of a single color), chroma (saturation, i.e., the degree to which it differs from white), and value (brightness, i.e., the intensity of light). In this specification, color may be defined by only one of the above three aspects or two of the aspects which are selected arbitrarily. In this specification, a difference between two colors of light means a difference in at least one of the above three aspects and includes a difference in the shapes of two spectra of light or in the distributions of the relative intensity of the peaks in the spectra.

Note that in this specification, the terms "film" and "layer" can be interchanged depending on the case or circumstances. For example, the term "conductive layer" can be changed into the term "conductive film" in some cases. Also, the term "insulating film" can be changed into the term "insulating layer" in some cases.

Note that in this specification, a condensed ring refers to an organic compound in which two or more carbocyclic compounds, two or more heterocyclic compounds, or one or more carbocyclic compounds and one or more heterocyclic compounds are bonded to each other by sharing two or more atoms.

Embodiment 1

In this embodiment, an organic compound of one embodiment of the present invention is described below.

The organic compound of one embodiment of the present invention is represented by General Formula (G0) shown below.

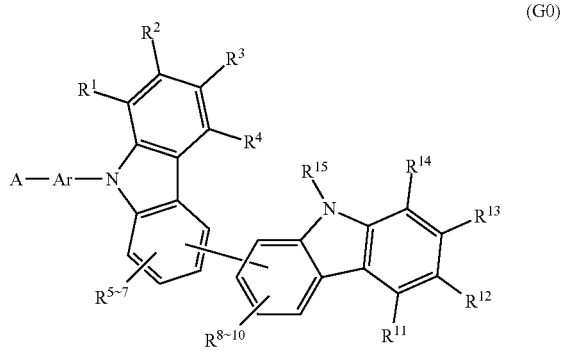

(G0)

In General Formula (G0), A represents a benzofuro[3,2-d]pyrimidine skeleton or a benzothieno[3,2-d]pyrimidine skeleton that includes at least a substituent including one condensed ring or two condensed rings; each of $R^1$ to $R^{15}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

In this case, Ar in General Formula (G0) is preferably bonded to the 4-position of the benzofuro[3,2-d]pyrimidine skeleton or the benzothieno[3,2-d]pyrimidine skeleton.

A structure in which a bicarbazole skeleton is bonded to the 4-position of the benzofuro[3,2-d]pyrimidine skeleton or the benzothieno[3,2-d]pyrimidine skeleton directly or through an arylene group is preferable because the structure has high electrochemical stability and a high carrier-transport property and a highly-reliable light-emitting element with low driving voltage can be provided by using the structure. Furthermore, the benzofuro[3,2-d]pyrimidine skeleton or the benzothieno[3,2-d]pyrimidine skeleton that includes a substituent including one condensed ring or two condensed rings is effective in improving electrochemical stability and film quality, so that the reliability of the light-emitting element can be improved.

The organic compound of one embodiment of the present invention is represented by General Formula (G1) shown below.

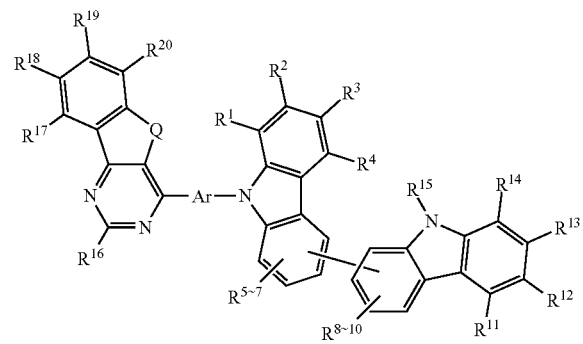

(G1)

In General Formula (G1), Q represents oxygen or sulfur; each of $R^1$ to $R^{15}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; any one of $R^{16}$ to $R^{20}$ represents a substituent including one condensed ring or two condensed rings and each of the others independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

The organic compound of one embodiment of the present invention is represented by General Formula (G2) shown below.

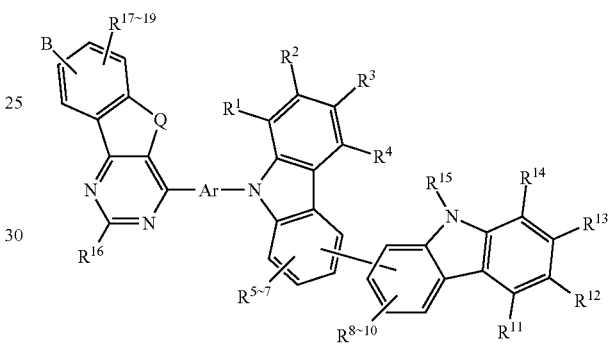

(G2)

In General Formula (G2), Q represents oxygen or sulfur; each of $R^1$ to $R^{19}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; Ar represents a substituted or unsubstituted arylene group having 6 to 25 carbon atoms, or a single bond; and B represents a substituent including one condensed ring or two condensed rings.

As shown in General Formulae (G1) and (G2), the structure in which one condensed ring or two condensed rings is/are included in the 6-, 7-, 8-, or 9-position of the benzofuro[3,2-d]pyrimidine skeleton or the benzothieno[3,2-d]pyrimidine skeleton is particularly effective in improving electrochemical stability and film quality, so that the reliability of a light-emitting element can be drastically improved.

The organic compound of one embodiment of the present invention is represented by General Formula (G3) shown below. As shown in General Formula (G3), the substituent including one condensed ring or two condensed rings is preferably bonded to the 8-position of the benzofuro[3,2-d]pyrimidine skeleton or the benzothieno[3,2-d]pyrimidine skeleton. The structure not only has high electrochemical stability and high film quality but also can exhibit a high T1 level.

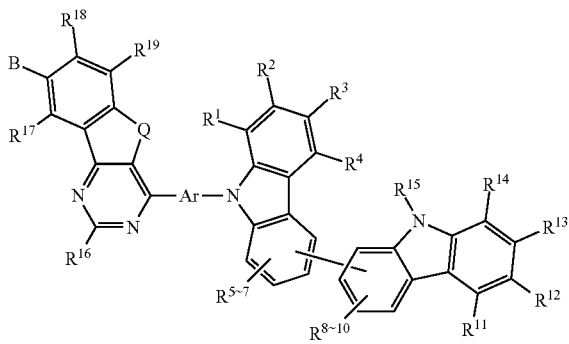

(G3)

In General Formula (G3), Q represents oxygen or sulfur; each of $R^1$ to $R^{19}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; Ar represents a substituted or unsubstituted arylene group having 6 to 25 carbon atoms, or a single bond; and B represents a substituent including one condensed ring or two condensed rings.

In the above structure, when the condensed ring is too small, the effect is small, whereas when the condensed ring is too large, the sublimation property or solubility is reduced. Thus, the number of carbon atoms in the condensed ring is preferably 10 to 20. Examples of such a condensed ring include a condensed aromatic ring such as a naphthalene ring, a fluorene ring, a phenanthrene ring, or a triphenylene ring and a condensed heteroaromatic ring such as a carbazole ring, a dibenzofuran ring, a dibenzothiophene ring, a benzonaphthofuran ring, a benzonaphthothiophene ring, an indolocarbazole ring, a benzofurocarbazole ring, a benzothienocarbazole ring, an indenocarbazole ring, or a dibenzocarbazole ring. Note that the substituent including one condensed ring or two condensed rings (B in General Formulae (G2) and (G3)) may include not only these condensed aromatic rings or condensed heteroaromatic rings but also a benzene ring. That is, the substituent including one condensed ring or two condensed rings (B in General Formulae (G2) and (G3)) may be formed by a combination of the substituted or unsubstituted condensed aromatic ring, the substituted or unsubstituted condensed heteroaromatic ring, and a substituted or unsubstituted benzene ring. For example, the condensed heteroaromatic ring may be bonded to a benzofuropyrimidine skeleton or a benzothienopyrimidine skeleton through a phenylene group or a biphenyldiyl group.

In the above structure, the condensed ring preferably has any one of a carbazole skeleton, a dibenzothiophene skeleton, and a dibenzofuran skeleton, in which case the organic compound of one embodiment of the present invention can have high electrochemical stability and a high carrier-transport property. Furthermore, with the skeleton, a high T1 level can be easily kept.

The organic compound of one embodiment of the present invention is represented by General Formula (G4) shown below. A structure in which a substituent having a carbazole skeleton is included in the 8-position of the benzofuro[3,2-d]pyrimidine skeleton or the benzothieno[3,2-d]pyrimidine skeleton is preferable because the structure can exhibit a particularly high T1 level.

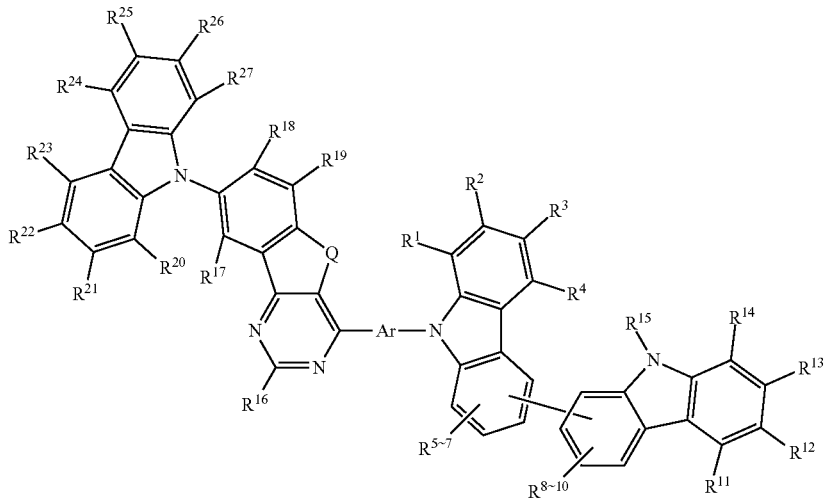

(G4)

In General Formula (G4), Q represents oxygen or sulfur; each of $R^1$ to $R^{27}$ independently represents any of hydrogen, an alkyl group having 1 to 6 carbon atoms, a substituted or unsubstituted cycloalkyl group, having 3 to 7 carbon atoms, and a substituted or unsubstituted aryl group having 6 to 13 carbon atoms; and Ar represents a substituted or unsubstituted arylene group having 6 to 25 carbon atoms, or a single bond.

The organic compound of one embodiment of the present invention is represented by General Formula (G5) shown below. A structure in which a substituent having a carbazole skeleton is included in the 8-position of a benzofuro[3,2-d]pyrimidine skeleton or a benzothieno[3,2-d]pyrimidine skeleton is preferable because the structure can exhibit a particularly high T1 level.

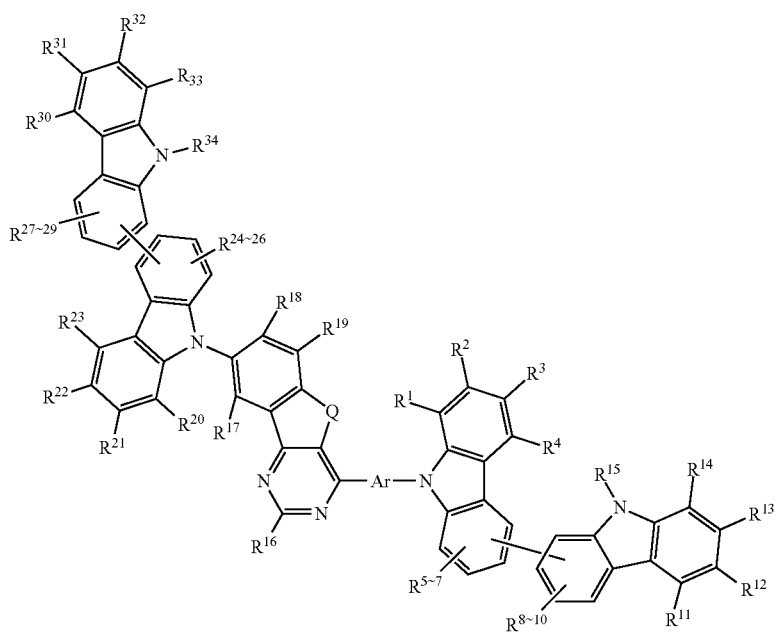

(G5)

In General Formula (G5), Q represents oxygen or sulfur; each of $R^1$ to $R^{34}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

The organic compound of one embodiment of the present invention is represented by General Formula (G6) shown below. A bicarbazole skeleton is preferably a 2,3'-bi-9H-carbazole skeleton because the organic compound can have a particularly high carrier-transport property.

In General Formula (G6), Q represents oxygen or sulfur; $R^{15}$ represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

The organic compound of one embodiment of the present invention is represented by General Formula (G7) shown below. A bicarbazole skeleton is preferably a 2,3'-bi-9H-carbazole skeleton because the organic compound can have a particularly high carrier-transport property.

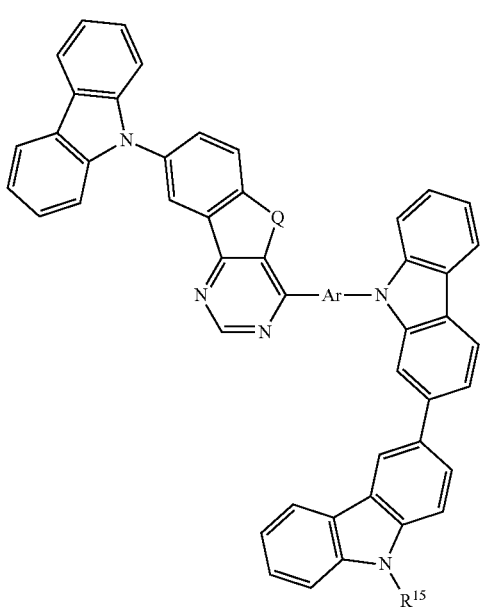

(G6)

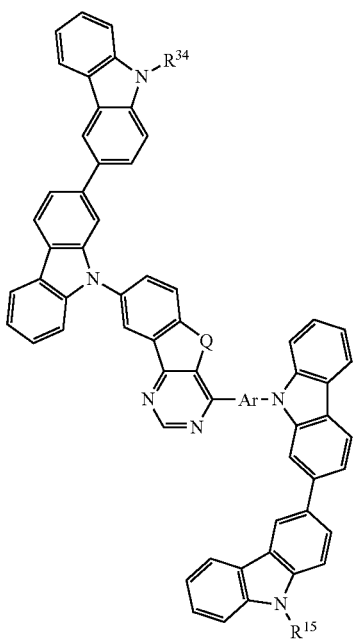

(G7)

In General Formula (G7), Q represents oxygen or sulfur; each of $R^{15}$ and $R^{34}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms, or a single bond.

In General Formulae (G0) to (G7), Ar represents a substituted or unsubstituted arylene group having 6 to 25 carbon atoms. Examples of the arylene group include a phenylene group, a naphthylene group, a biphenyldiyl group, a fluorenediyl group, and a spirofluorenediyl group. Specifically, for example, groups represented by Structural Formulae (Ar-1) to (Ar-27) shown below can be used. Note that the group represented by Ar is not limited thereto and may include a substituent.

(Ar-1)

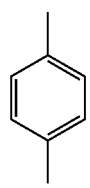

(Ar-2)

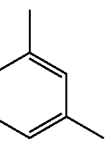

(Ar-3)

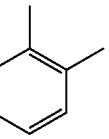

(Ar-4)

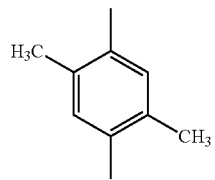

(Ar-5)

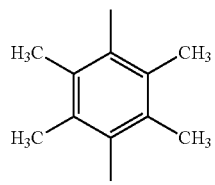

(Ar-6)

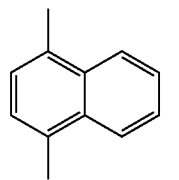

(Ar-7)

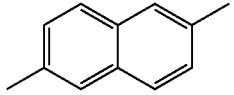

(Ar-8)

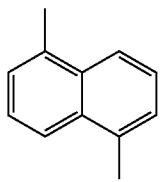

(Ar-9)

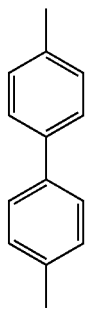

(Ar-10)

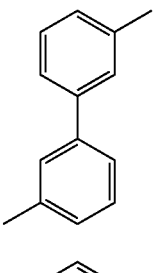

(Ar-11)

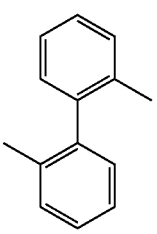

(Ar-12)

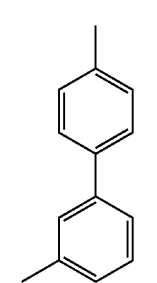

(Ar-13)

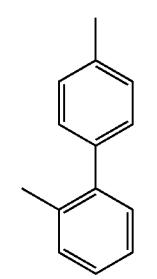

(Ar-14)
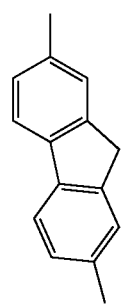
(Ar-15)
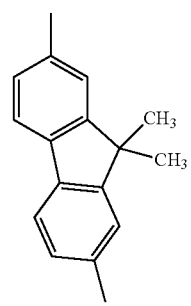
(Ar-16)
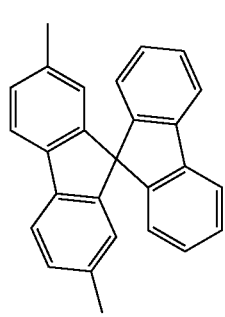
(Ar-17)
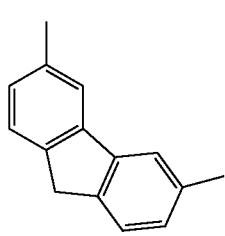
(Ar-18)
(Ar-19)
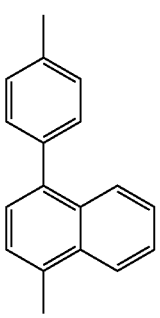
(Ar-20)
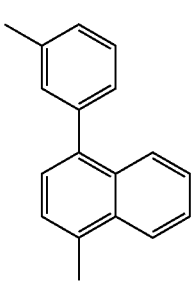
(Ar-21)
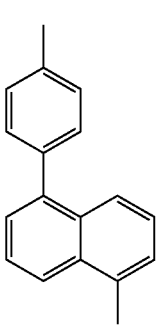
(Ar-22)
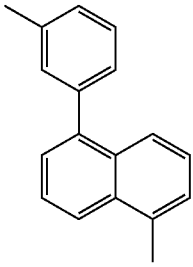
(Ar-23)
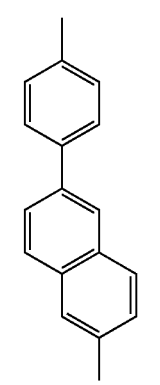

-continued

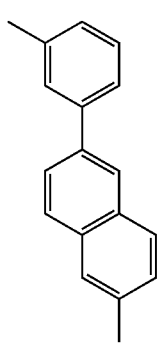
(Ar-24)

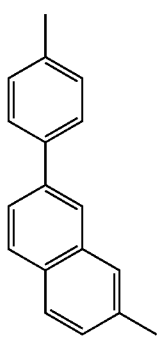
(Ar-25)

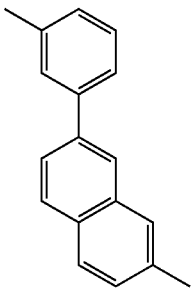
(Ar-26)

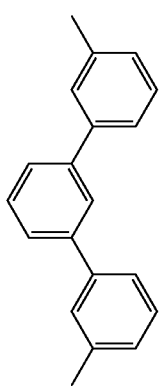
(Ar-27)

In General Formulae (G0) to (G7), each of $R^1$ to $R^{34}$ represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms. Examples of the alkyl group include a methyl group, an ethyl group, a propyl group, an isopropyl group, a butyl group, an isobutyl group, a tert-butyl group, and an n-hexyl group. Examples of the cycloalkyl group include a cyclopropyl group, a cyclobutyl group, a cyclopentyl group, and a cyclohexyl group. Examples of the aryl group include a phenyl group, a naphthyl group, a biphenylyl group, and a fluorenyl group. For example, groups represented by Structural Formulae (R-1) to (R-27) shown below can be given. Note that the groups represented by $R^1$ to $R^{34}$ are not limited thereto.

In the case where a condensed ring includes a substituent, the substituent can be an alkyl group having 1 to 6 carbon atoms, a cycloalkyl group having 3 to 7 carbon atoms, or an aryl group having 6 to 13 carbon atoms, for example. Although groups represented by Structural Formulae (R-1) to (R-27) shown below can be given as examples of the substituent, the groups are not limited thereto.

 (R-1)

 (R-2)

 (R-3)

 (R-4)

 (R-5)

 (R-6)

 (R-7)

 (R-8)

 (R-9)

 (R-10)

 (R-11)

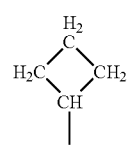 (R-12)
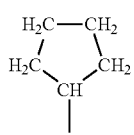 (R-13)
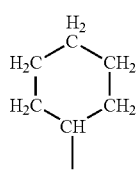 (R-14)
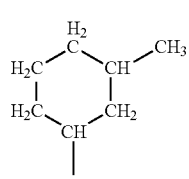 (R-15)
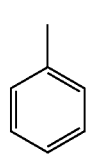 (R-16)
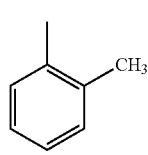 (R-17)
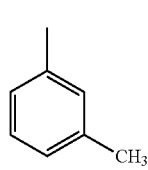 (R-18)
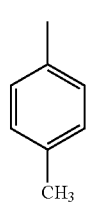 (R-19)
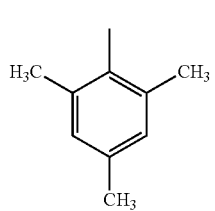 (R-20)
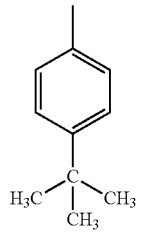 (R-21)
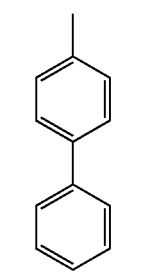 (R-22)
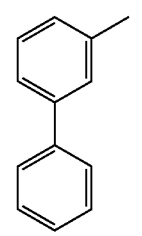 (R-23)
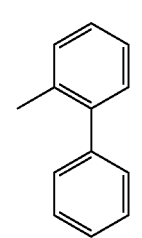 (R-24)
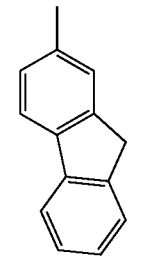 (R-25)
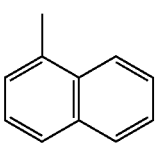 (R-26)
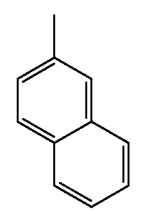 (R-27)

<Specific Examples of Compounds>
Specific examples of structures of the compounds represented by General Formulae (G0) to (G7) include compounds represented by Structural Formulae (101) to (152) shown below. Note that the compounds represented by General Formulae (G0) to (G7) are not limited to the following examples.
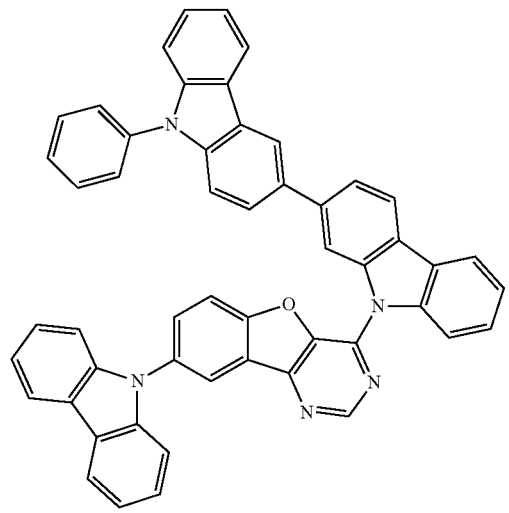
(100)
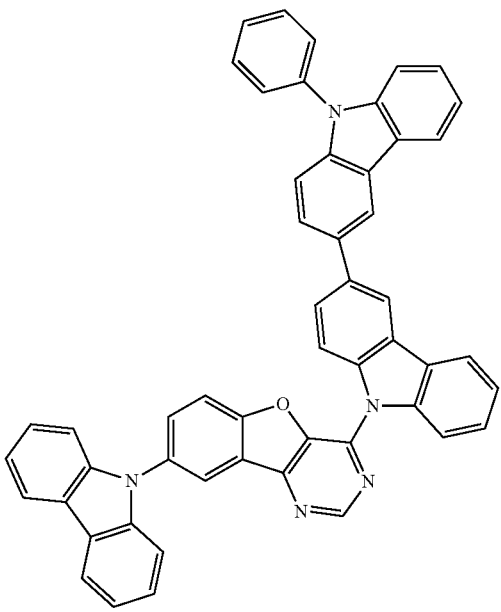
(101)
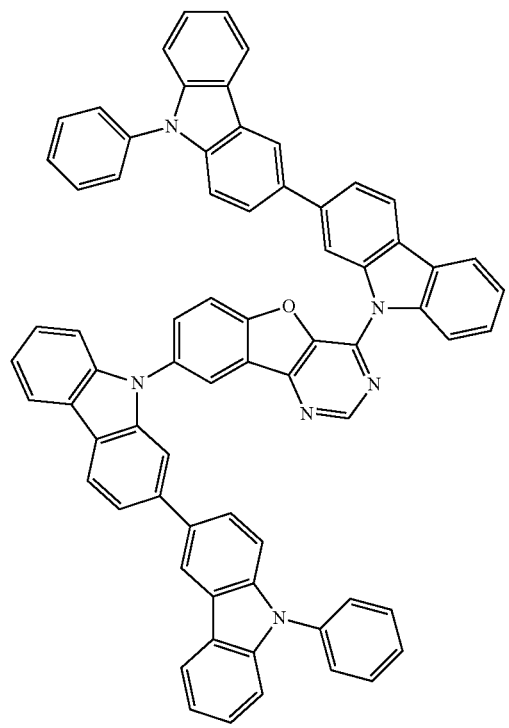
(102)

-continued
(103)
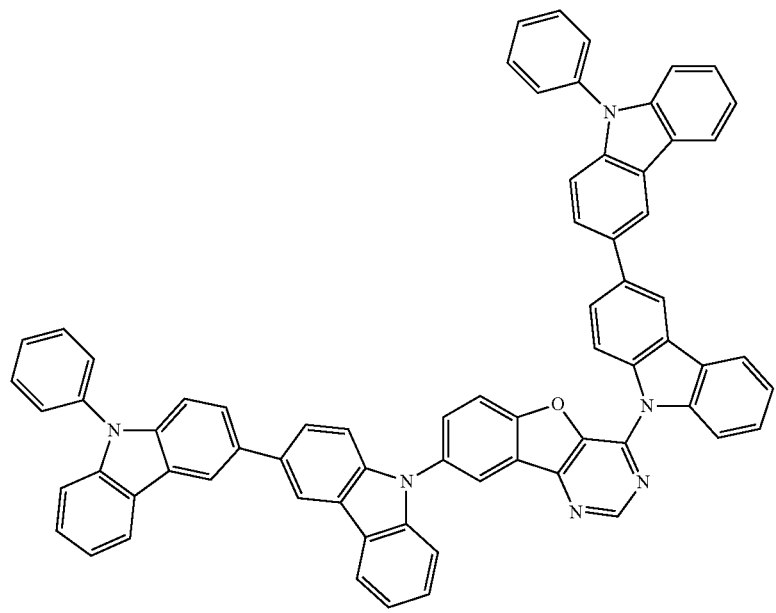
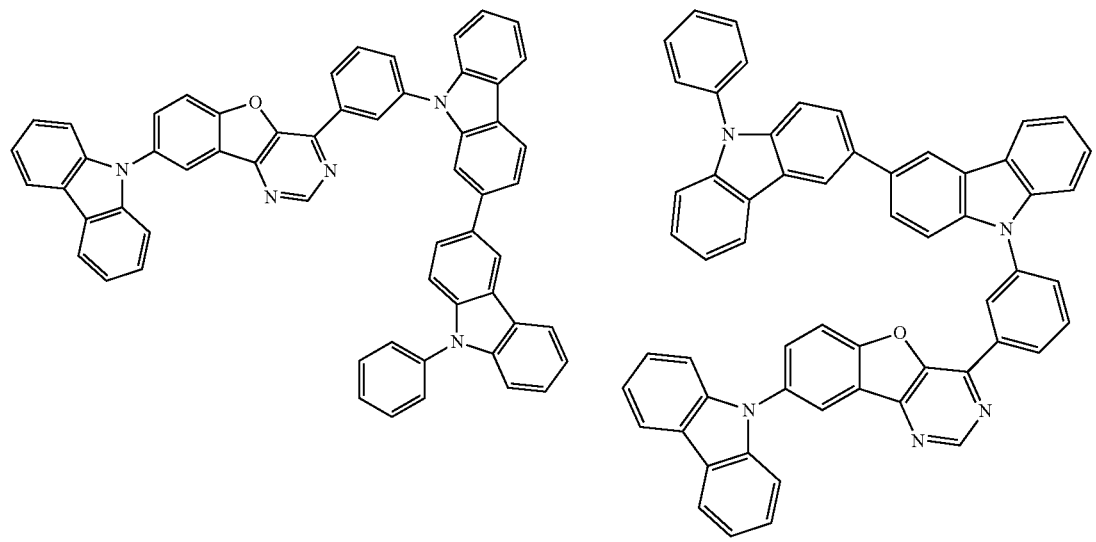

(106)
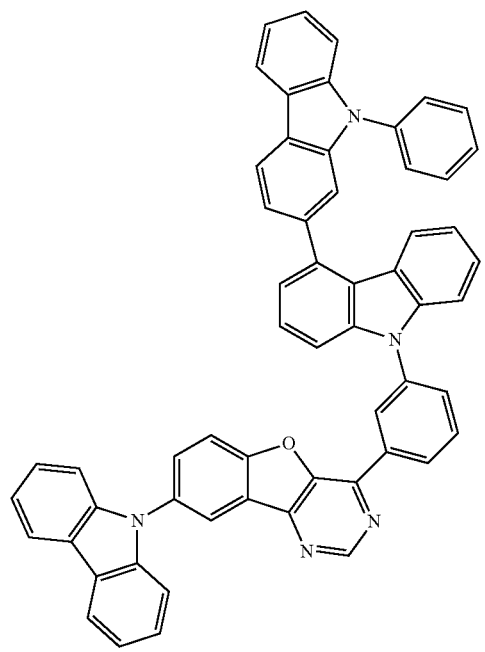
(107)
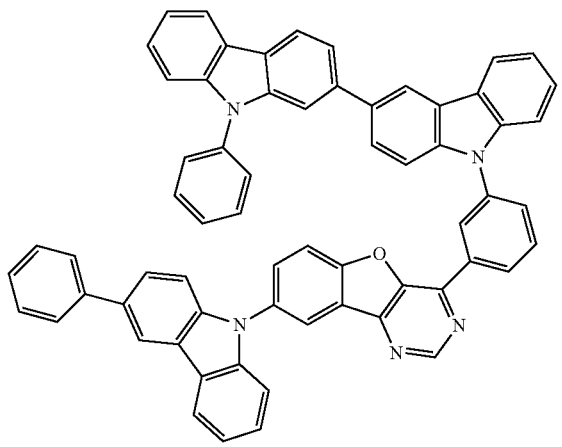
(108)
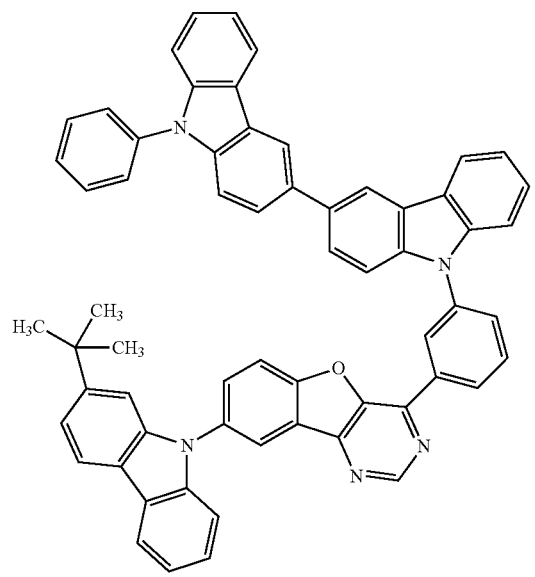
(109)
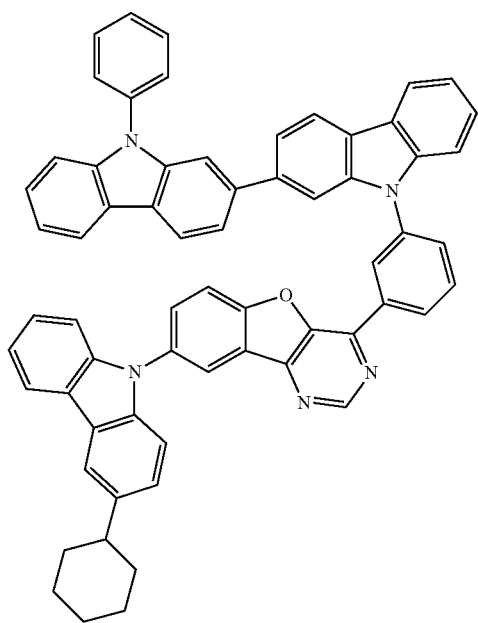

-continued
(110)
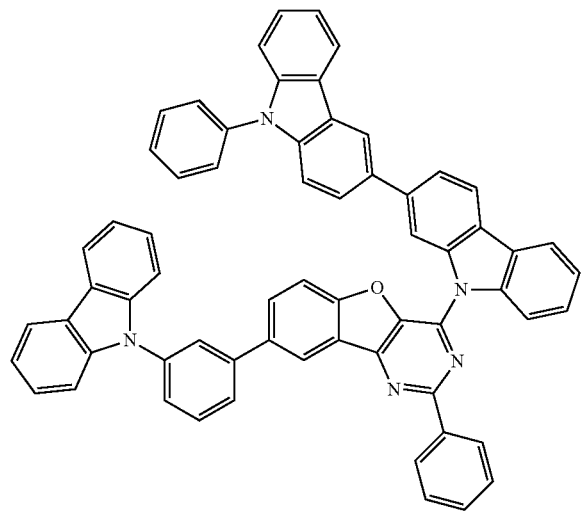
(111)
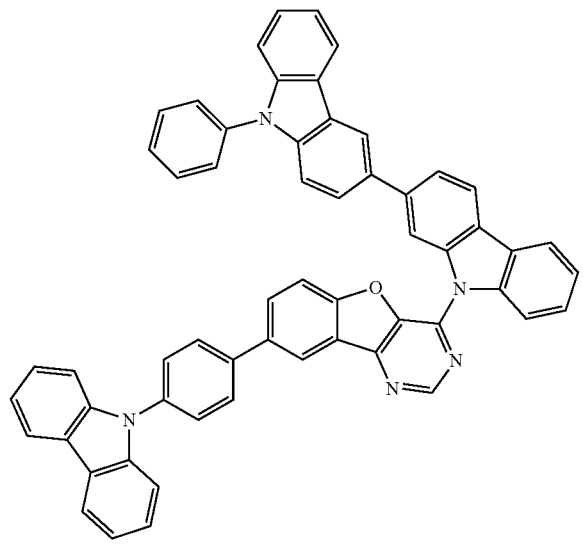
(112)
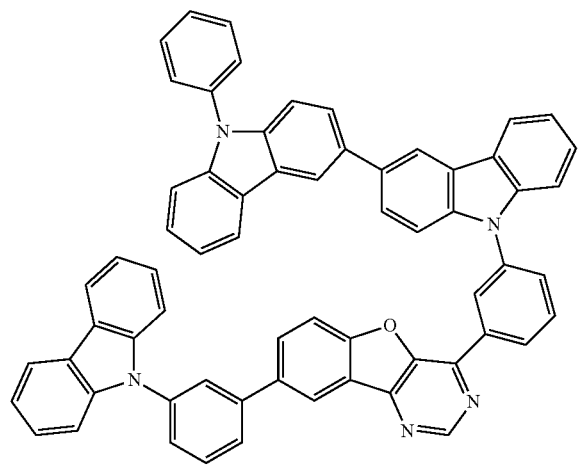
(113)
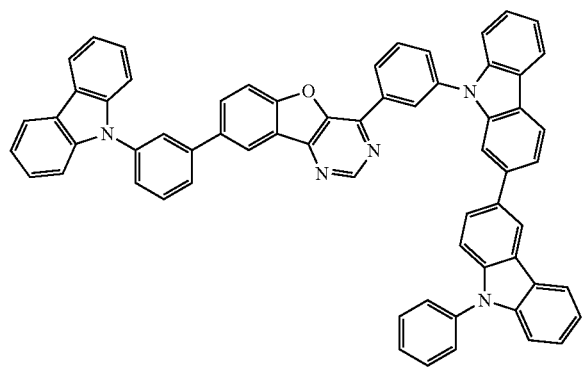
(114)
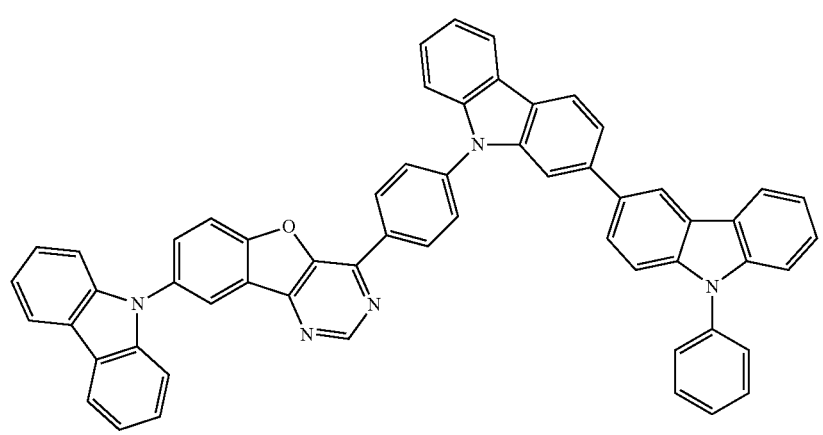

-continued
(115)
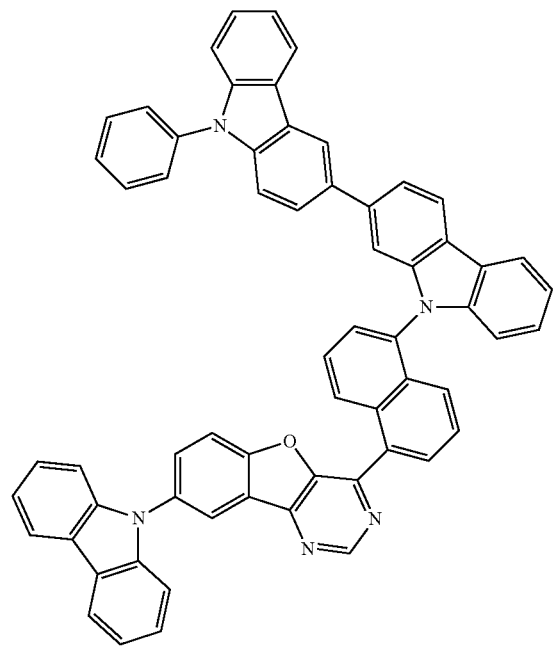
(116)
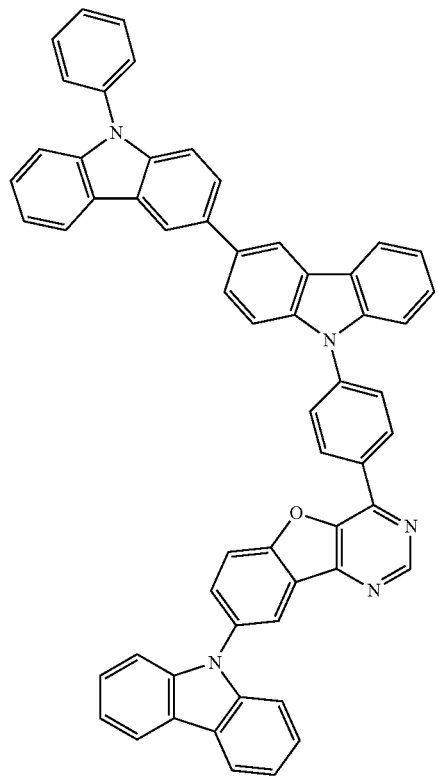
(117)
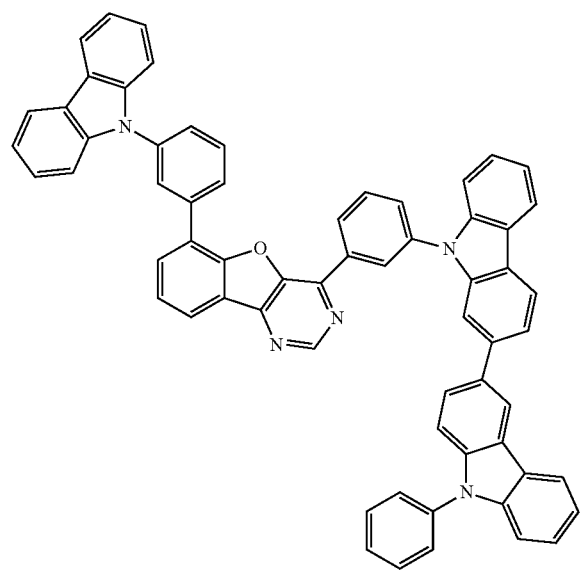
(118)
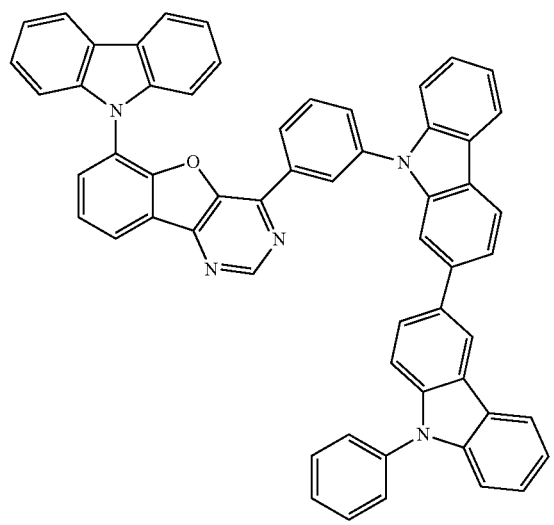

-continued
(119)
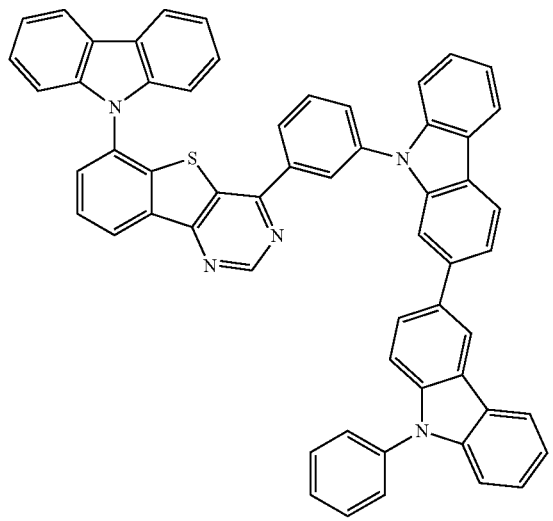
(120)
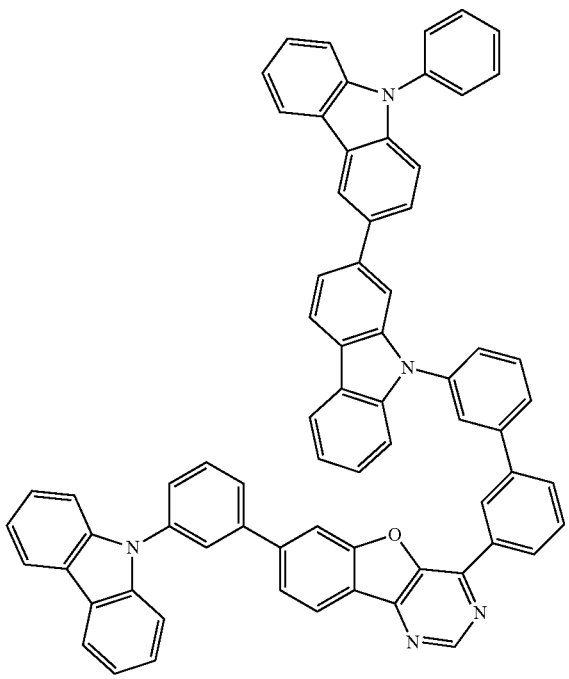
(121)
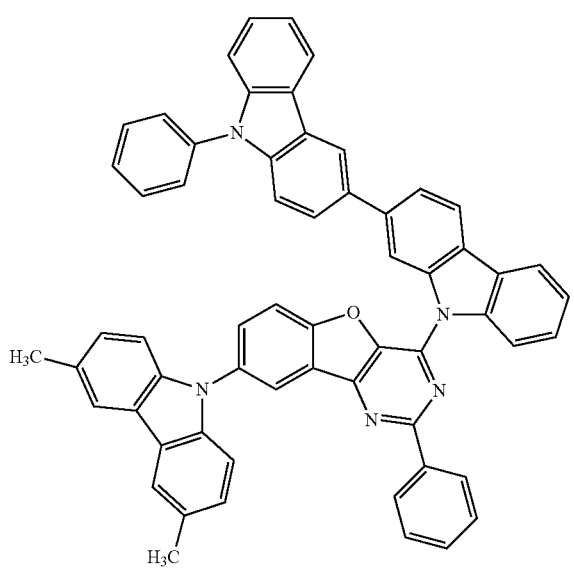

(122)
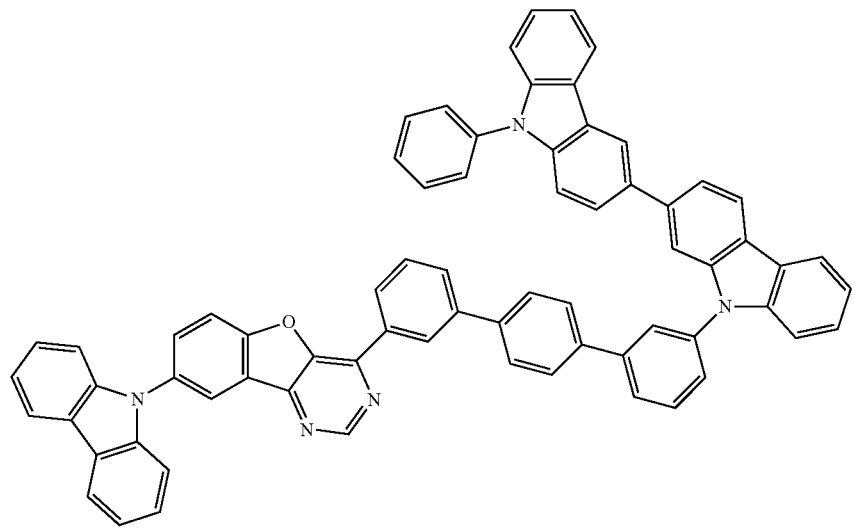
(123)
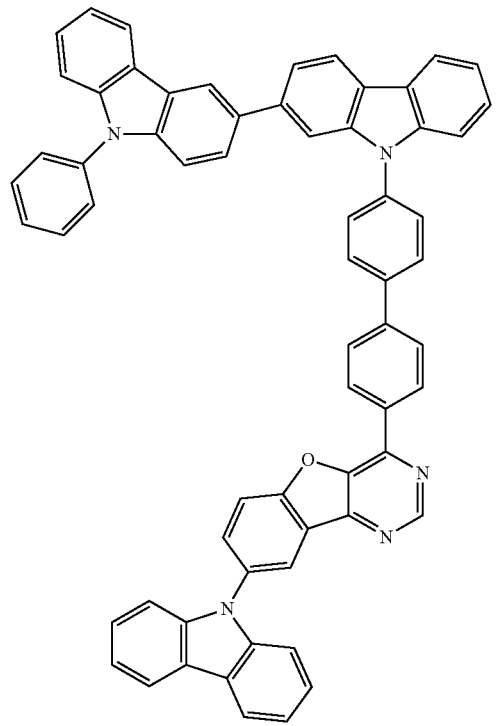
(124)
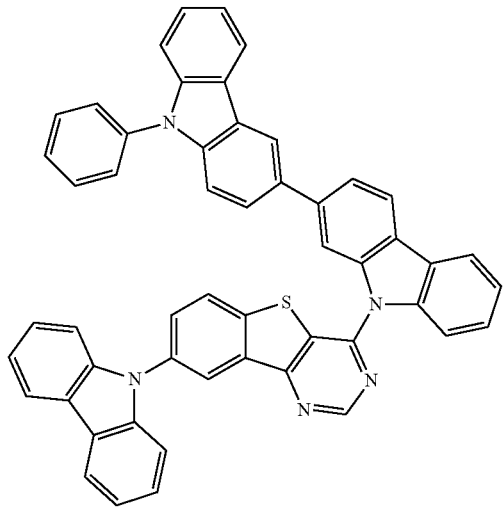

-continued
(125)
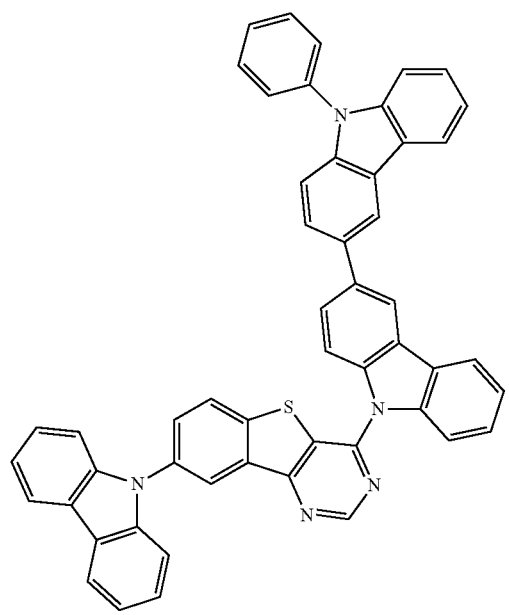
(126)
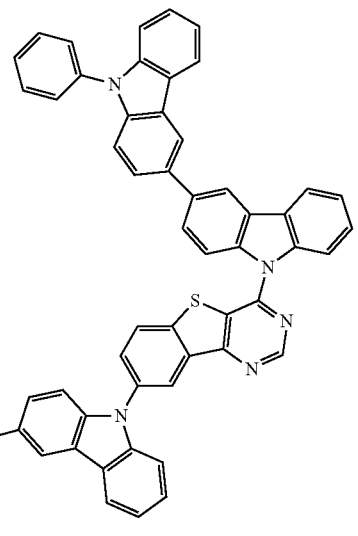
(127)
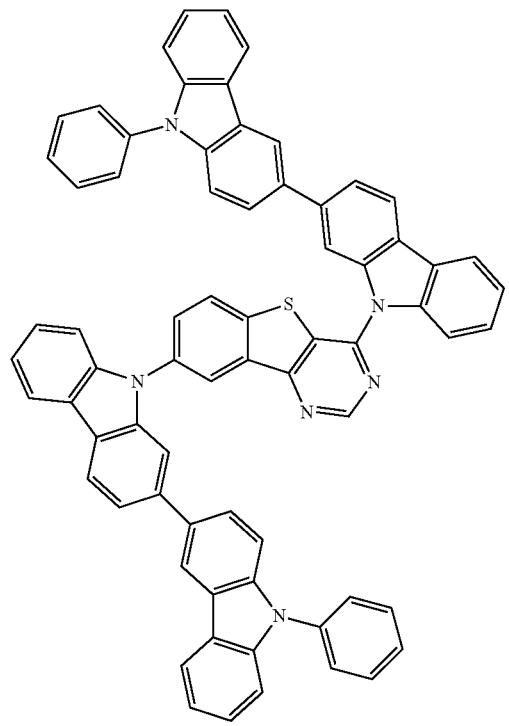
(128)
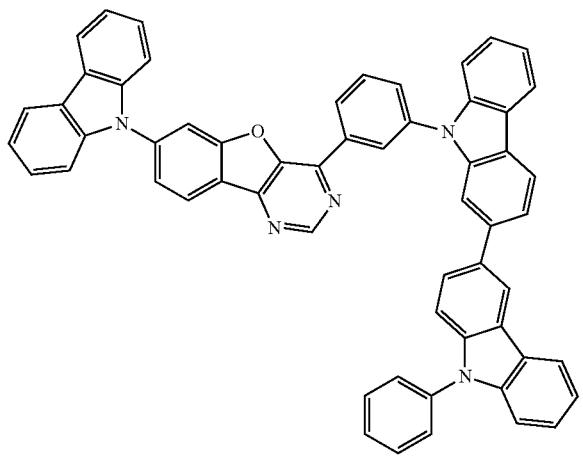

-continued
(129)
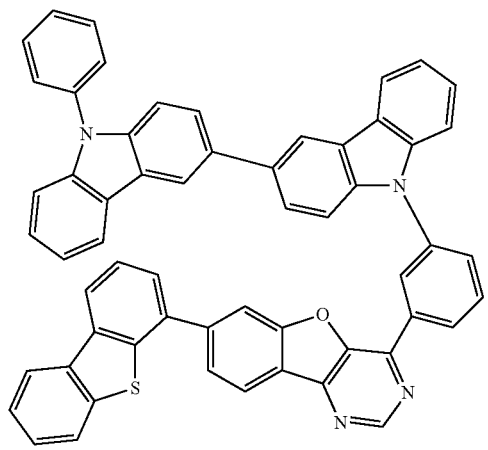
(130)
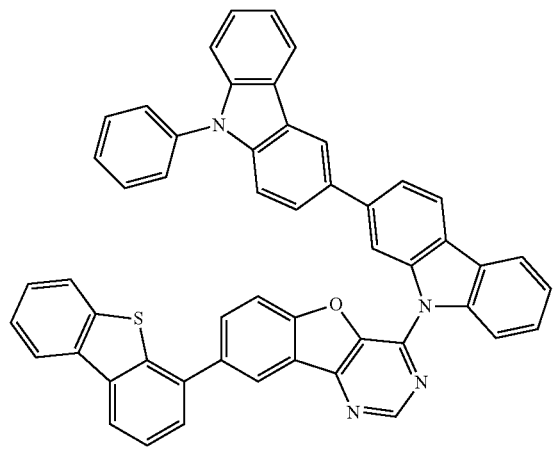
(131)
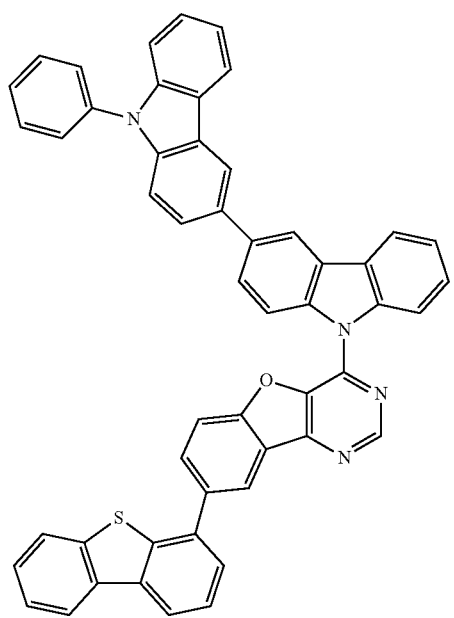
(132)
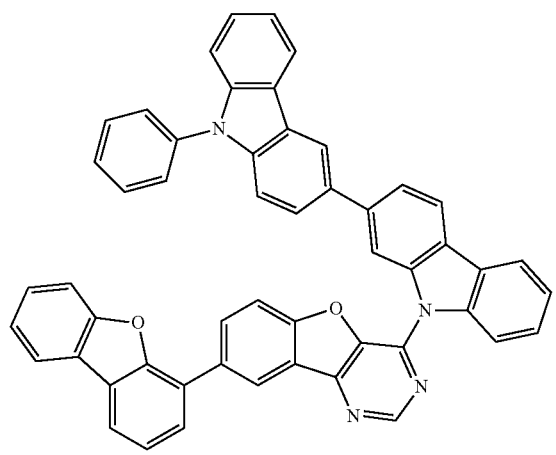

(133)
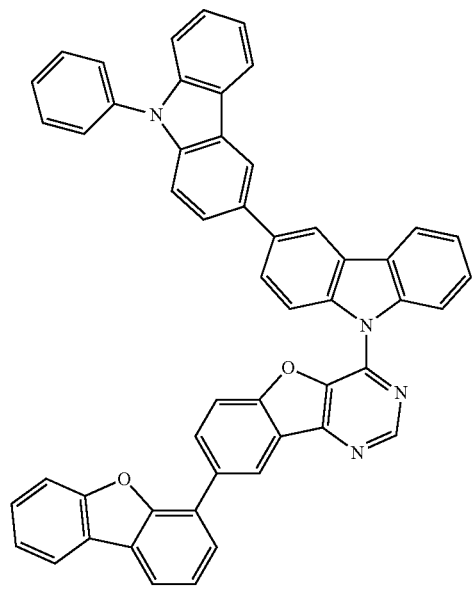
(134)
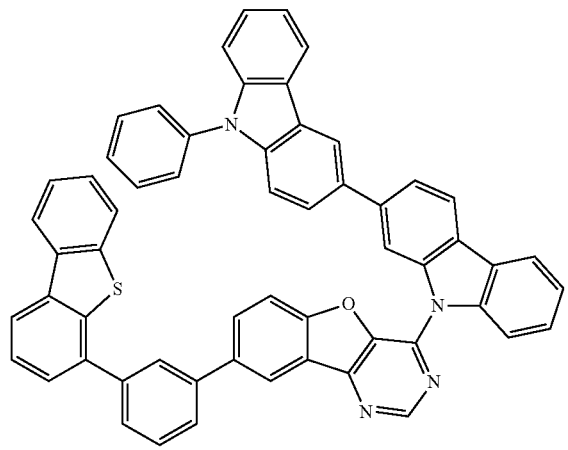
(135)
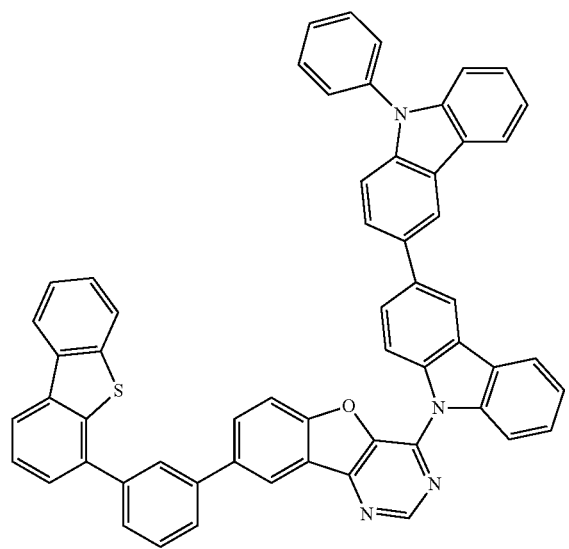
(136)
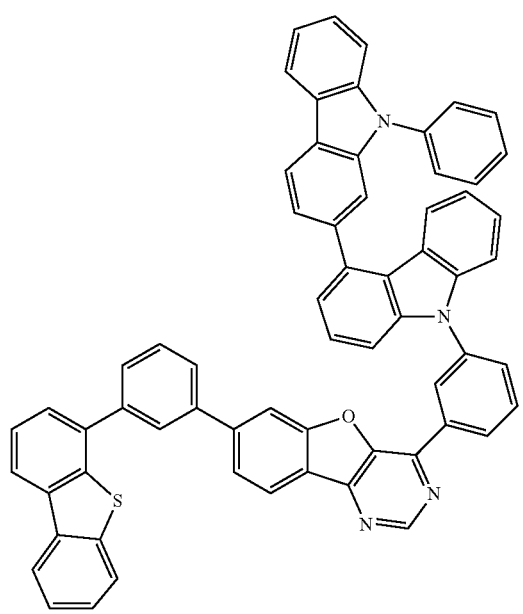

(137)
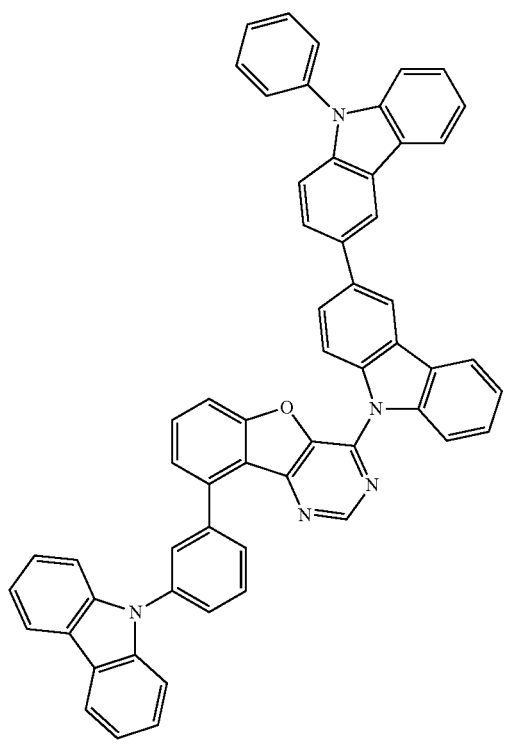
(138)
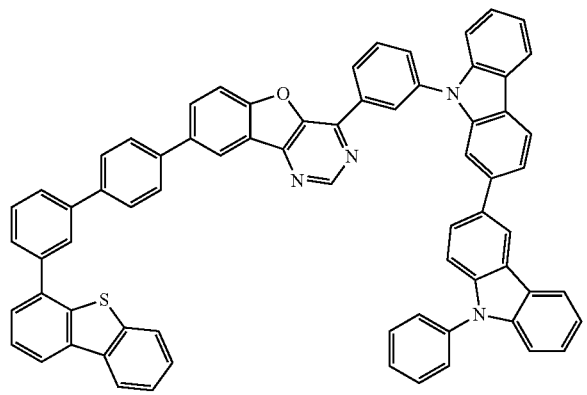
(139)
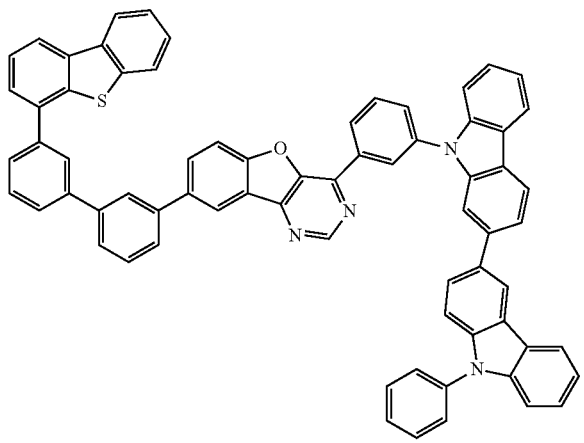
(140)
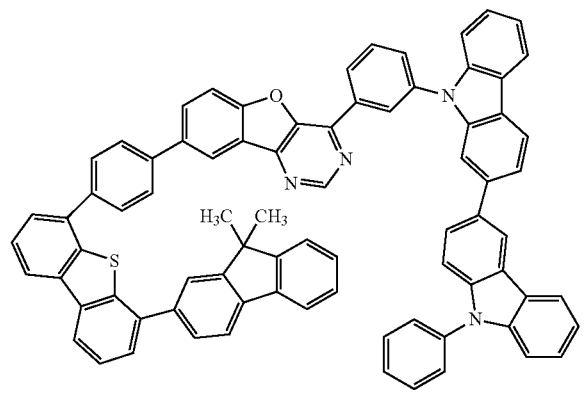

-continued
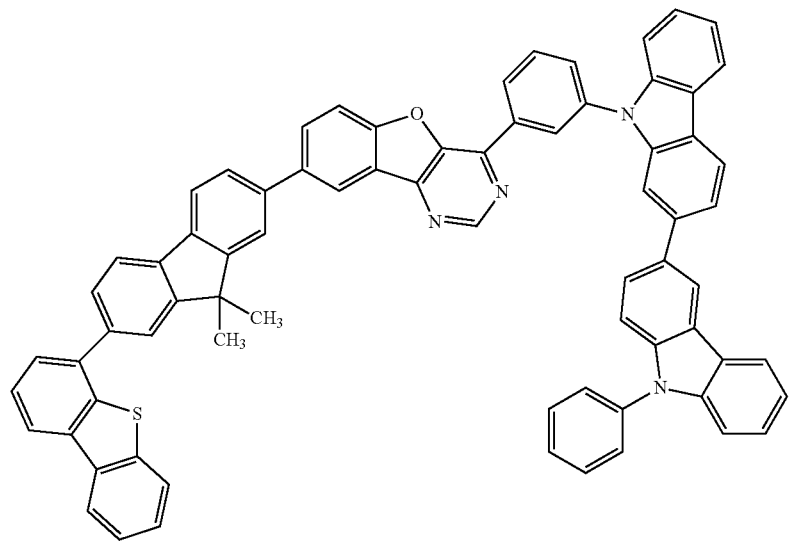
(141)
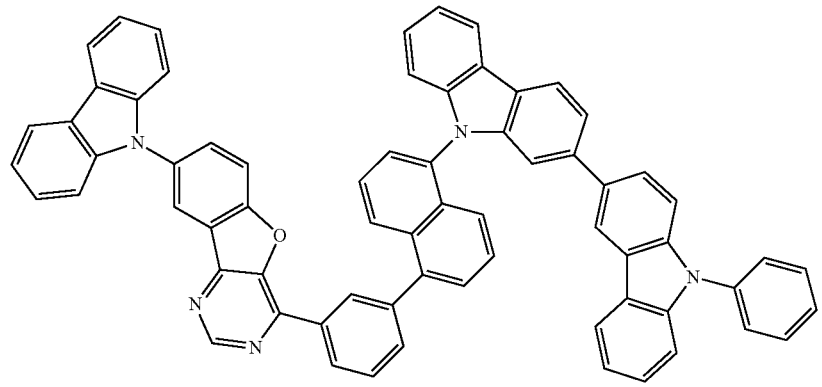
(142)
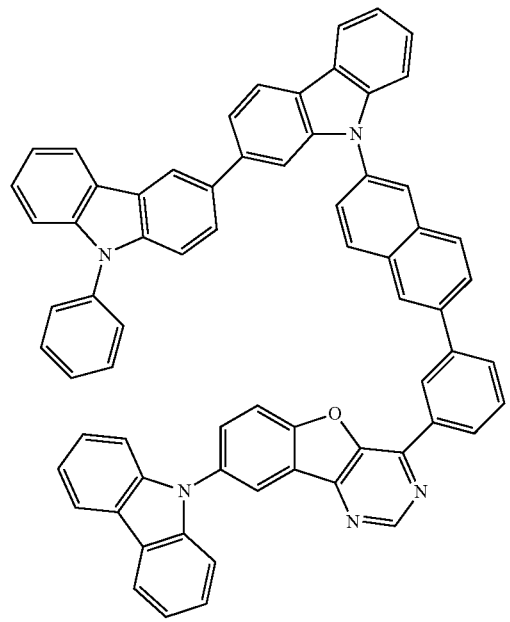
(143)
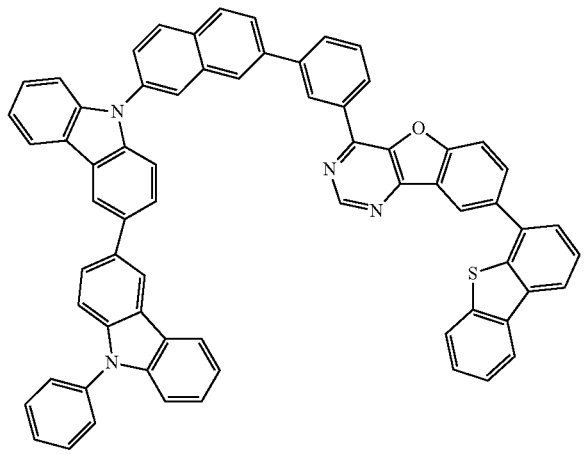
(144)

-continued
(145)
(146)
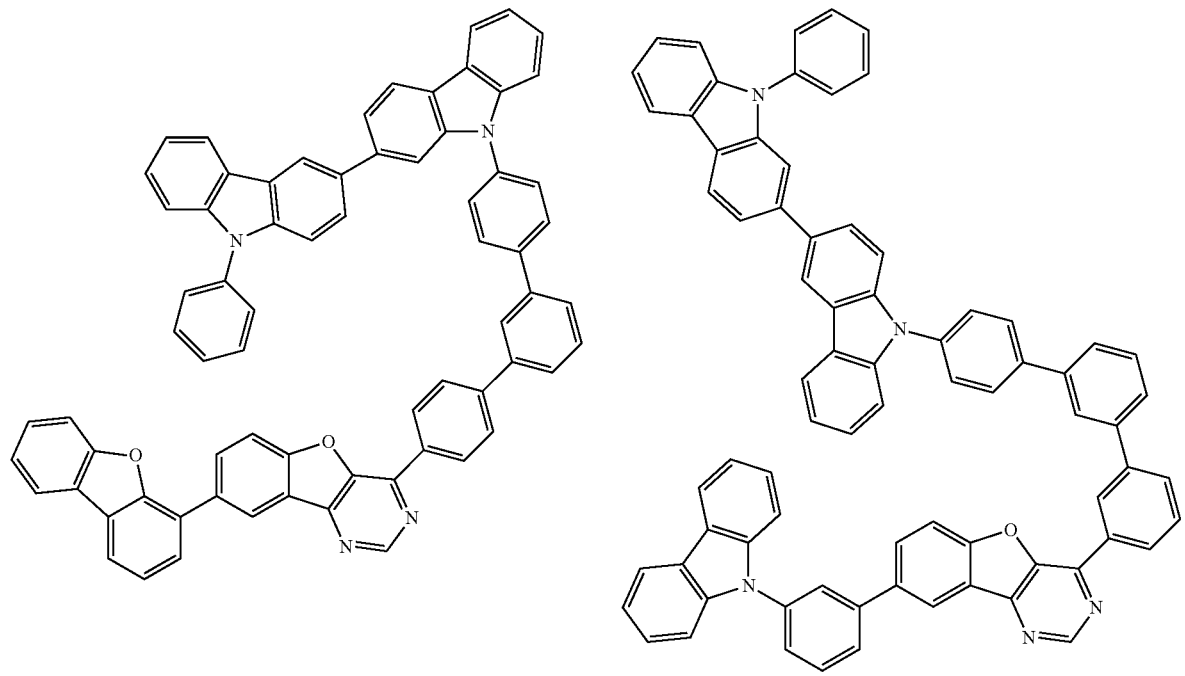
(147)
(148)
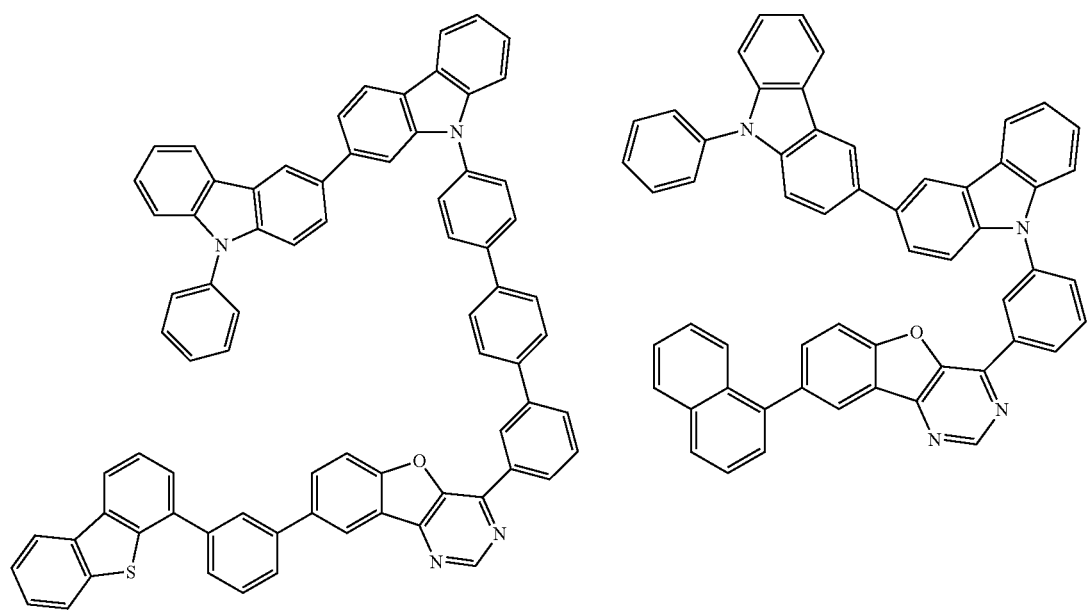

-continued (149)

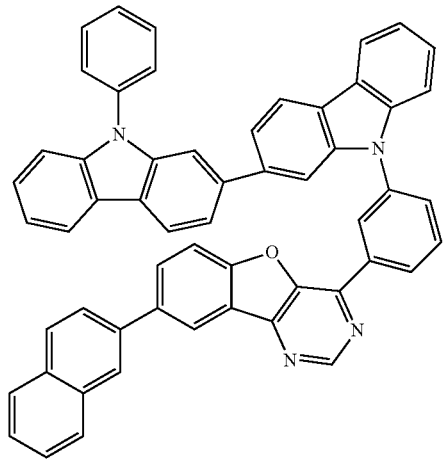

(150)

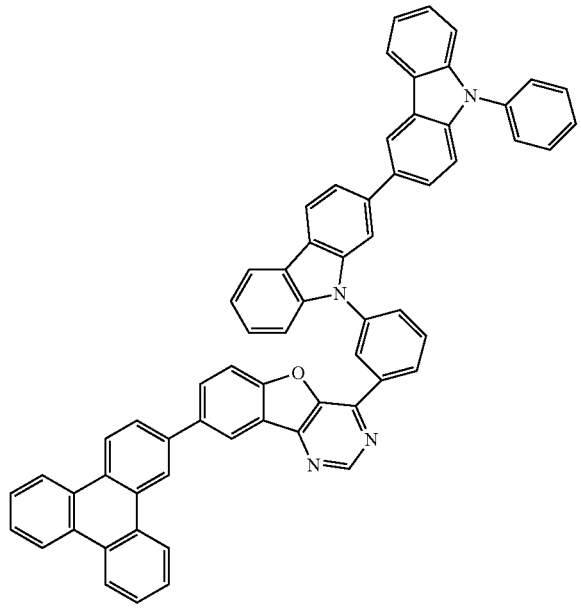

The organic compound of one embodiment of the present invention has a bicarbazole skeleton, a benzofuropyrimidine skeleton or a benzothienopyrimidine skeleton, and a substituent including one condensed ring or two condensed rings. The organic compound of one embodiment of the present invention has a wide band gap; thus, a light-emitting element including the compound can have high emission efficiency. In addition, the organic compound of one embodiment of the present invention has a high carrier-transport property; thus, a light-emitting element including the compound can have low driving voltage. The organic compound of one embodiment of the present invention is highly resistant to repetition of oxidation and reduction; thus, a light-emitting element including the compound can have high reliability.

In general, a compound in which π conjugated systems spread across a molecule, which is typified by an aromatic compound, is used as a host material or an electron-transport material of a light-emitting element. In particular, a π-electron deficient compound is favorably used. A condensed heterocyclic skeleton having a diazine skeleton is particularly preferable as the π-electron deficient compound because of having a high T1 level, high stability, and high reliability. Furthermore, a benzofuropyrimidine skeleton and a benzothienopyrimidine skeleton are particularly preferable because of having a high acceptor property.

Here, the present inventors have found that an organic compound having a bicarbazole skeleton, a benzofuropyrimidine skeleton or a benzothienopyrimidine skeleton, and a substituent including one condensed ring or two condensed rings has a high T1 level and can be favorably used as a host material of a light-emitting element, and a light-emitting element including the organic compound as a host material has high reliability.

A benzofuro[3,2-d]pyrimidine skeleton and a benzothieno[3,2-d]pyrimidine skeleton are preferably used as the benzofuropyrimidine skeleton and the benzothienopyrimidine skeleton, respectively, because of being available at low cost.

A structure in which a benzofuro[3,2-d]pyrimidine skeleton or a benzothieno[3,2-d]pyrimidine skeleton includes a substituent including one condensed ring or two condensed rings is preferable because the structure is effective in improving electrochemical stability and film quality, so that the reliability of a light-emitting element can be improved.

A structure in which a bicarbazole skeleton is bonded to the 4-position of the benzofuro[3,2-d]pyrimidine skeleton or the benzothieno[3,2-d]pyrimidine skeleton directly or through an arylene group is preferable because the structure has high electrochemical stability and a high carrier-transport property and a highly reliable light-emitting element with low driving voltage can be provided.

In the case where the bicarbazole skeleton is directly bonded to the benzofuropyrimidine skeleton or the benzothienopyrimidine skeleton, a relatively low molecular compound is formed, and therefore, a structure that is suitable for vacuum evaporation is obtained, which is preferable for a material for a light-emitting element. In general, a lower molecular weight tends to reduce heat resistance after film formation. However, because of high rigidity of the benzofuropyrimidine skeleton, the benzothienopyrimidine skeleton, and the bicarbazole skeleton, the compound of one embodiment of the present invention can have sufficient heat resistance even with a relatively low molecular weight. The structure is preferable because a band gap and an excitation energy level are increased.

A structure in which a benzofuro[3,2-d]pyrimidine skeleton or a benzothieno[3,2-d]pyrimidine skeleton includes a substituent including one condensed ring or two condensed rings in the 6-, 7-, 8-, or 9-position is preferable because the structure is particularly effective in improving electrochemical stability and film quality, so that the reliability of a light-emitting element can be drastically improved.

When the number of carbon atoms in the condensed ring is too large, a carrier-transport property is hindered in some cases. Thus, the number of carbon atoms in the condensed ring skeleton is preferably 10 to 20.

Examples of such a condensed ring include, as described above, a condensed aromatic ring such as a naphthalene ring, a fluorene ring, a phenanthrene ring, or a triphenylene ring and a condensed heteroaromatic ring such as a carbazole ring, a dibenzofuran ring, a dibenzothiophene ring, a benzonaphthofuran ring, a benzonaphthothiophene ring, an indolocarbazole ring, a benzofurocarbazole ring, a benzothienocarbazole ring, an indenocarbazole ring, or a dibenzocarbazole ring. Note that the substituent including one condensed ring or two condensed rings (B in General Formulae (G2) and (G3)) may include not only these condensed aromatic rings or condensed heteroaromatic rings but also a benzene ring. That is, the substituent including one condensed ring or two condensed rings (B in General Formulae (G2) and (G3)) may be formed by a combination of the substituted or unsubstituted condensed aromatic ring, the substituted or unsubstituted condensed heteroaromatic ring, and a substituted or unsubstituted benzene ring. For example, the condensed heteroaromatic ring may be bonded to a benzofuropyrimidine skeleton or a benzothienopyrimidine skeleton through a phenylene group or a biphenyldiyl group.

In the above structure, the condensed ring preferably has any one of a carbazole skeleton, a dibenzothiophene skeleton, and a dibenzofuran skeleton, in which case the organic compound of one embodiment of the present invention can have a high T1 level, high electrochemical stability, and a high carrier-transport property.

The organic compound of one embodiment of the present invention can be regarded as a bipolar material because the organic compound includes a benzofuropyrimidine skeleton having an electron-transport property and a carbazole skeleton having a hole-transport property in one molecule. Such a material with a high carrier-transport property is preferable because a light-emitting element with low driving voltage can be provided by using the material as a host material.

The compound of one embodiment of the present invention includes a π-electron rich heteroaromatic ring (a bicarbazole skeleton) and a π-electron deficient heteroaromatic ring (a benzofuropyrimidine skeleton or a benzothienopyrimidine skeleton). Accordingly, a donor-acceptor excited state is easily formed in a molecule. Furthermore, the π-electron rich heteroaromatic ring (the bicarbazole skeleton) and the π-electron deficient heteroaromatic ring (the benzofuropyrimidine skeleton or the benzothienopyrimidine skeleton) are bonded directly or through an arylene group, which can improve both the donor property and the acceptor property. By increasing both the donor property and the acceptor property in the molecule, an overlap between a region where the highest occupied molecular orbital (HOMO) is distributed and a region where the lowest unoccupied molecular orbital (LUMO) is distributed can be small, and the energy difference between the singlet excitation energy level and the triplet excitation energy level of the compound can be small. Moreover, the triplet excitation energy level of the compound can be kept high. Note that the molecular orbital refers to spatial distribution of electrons in a molecule, and can show the probability of finding of electrons. In addition, with the molecular orbital, electron configuration of the molecule (spatial distribution and energy of electrons) can be described in detail.

When a difference between the singlet excitation energy level and the triplet excitation energy level is small, with low thermal energy at 100° C. or lower, preferably at approximately room temperature, the triplet excitation energy can be upconverted to the singlet excitation energy by reverse intersystem crossing. Therefore, the compound of one embodiment of the present invention is suitably used as a compound that has a function of converting the triplet excitation energy into the singlet excitation energy or a compound that has a function of converting the triplet excitation energy into the singlet excitation energy and converting it into light emission. For efficient reverse intersystem crossing, the difference between the singlet excitation energy level and the triplet excitation energy level is preferably greater than 0 eV and less than or equal to 0.3 eV, more preferably greater than 0 eV and less than or equal to 0.2 eV, still more preferably greater than 0 eV and less than or equal to 0.1 eV.

Note that when the region where the HOMO is distributed and the region where the LUMO is distributed overlap each other and transition dipole moment between the HOMO level and the LUMO level is larger than 0, light emission can be obtained from an excited state related to the HOMO level and the LUMO level (e.g., the lowest singlet excited state). Therefore, the compound of one embodiment of the present invention is suitable as a light-emitting material that has a function of converting the triplet excitation energy into the singlet excitation energy; in other words, the compound is suitable as a thermally activated delayed fluorescence material.

A film of the compound of this embodiment can be formed by an evaporation method (including a vacuum evaporation method), an inkjet method, a coating method, gravure printing, or the like.

This embodiment can be combined with any other embodiment as appropriate.

Embodiment 2

In this embodiment, a method for synthesizing the organic compound of one embodiment of the present invention represented by General Formula (G0) is described. Note that the methods for synthesizing the compound of one embodiment of the present invention are not limited to the synthesis methods below.

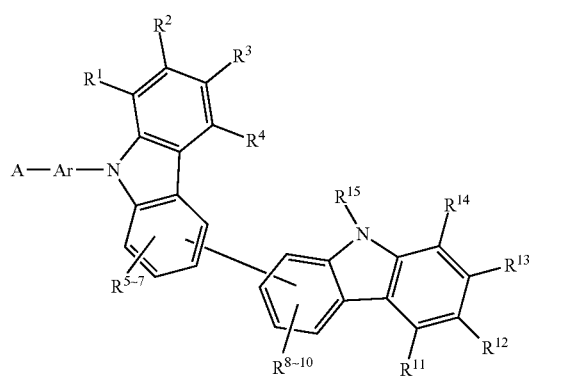

(G0)

The bicarbazole compound represented by General Formula (G0) can be synthesized by a simple synthesis scheme as follows. For example, as shown below in Scheme (a), a halogen compound of a benzofuropyrimidine including a substituent including one condensed ring or two condensed rings or a halogen compound of a benzothienopyrimidine including a substituent including one condensed ring or two condensed rings (A1), or a dihalogen compound of a substituted or unsubstituted benzofuropyrimidine or a dihalogen compound of a substituted or unsubstituted benzothienopyrimidine (A1') reacts with an arylboronic acid compound of a bicarbazole derivative (A2) or a bicarbazole derivative (A2') to form the compound represented by General Formula (G0). Alternatively, the compound represented by General Formula (G0) may be obtained in such a manner that an intermediate (B2) is obtained through a reaction with a halogen-substituted aryl boronic acid (B1) and then made to react with the bicarbazole derivative (A2'), as shown below in Scheme (b). Alternatively, the compound represented by General Formula (G0) may be obtained in such a manner that an intermediate (C1) is obtained through a reaction with one of halogens of the dihalogen compound of a substituted or unsubstituted benzofuropyrimidine or the dihalogen compound of a substituted or unsubstituted benzothienopyrimidine (A1') and one of the arylboronic acid compound of a bicarbazole derivative (A2) and the bicarbazole derivative (A2') and then made to react with a boronic acid compound of a derivative including one condensed ring or two condensed rings (C2), as shown below in Scheme (c).

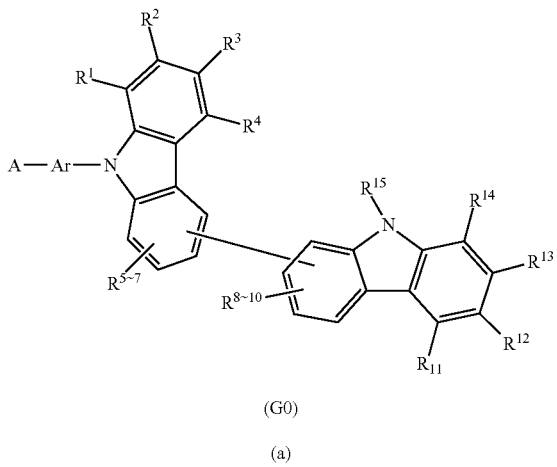

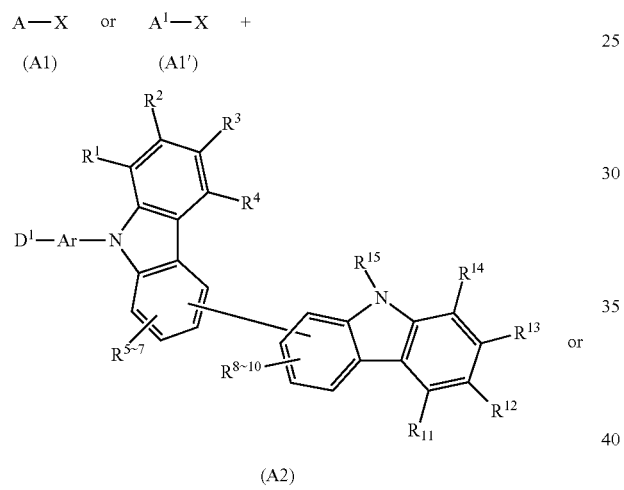

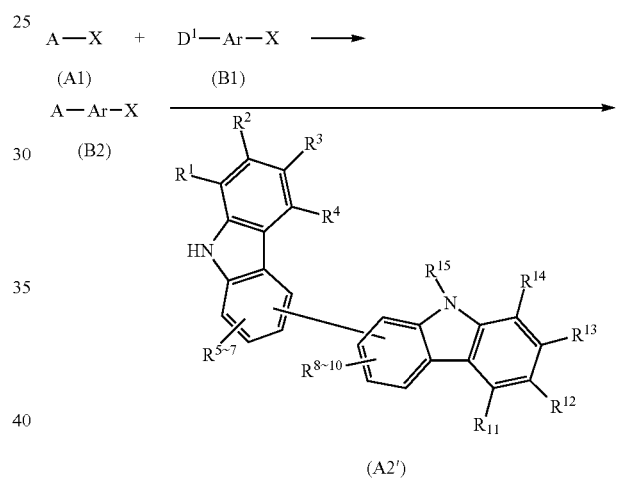

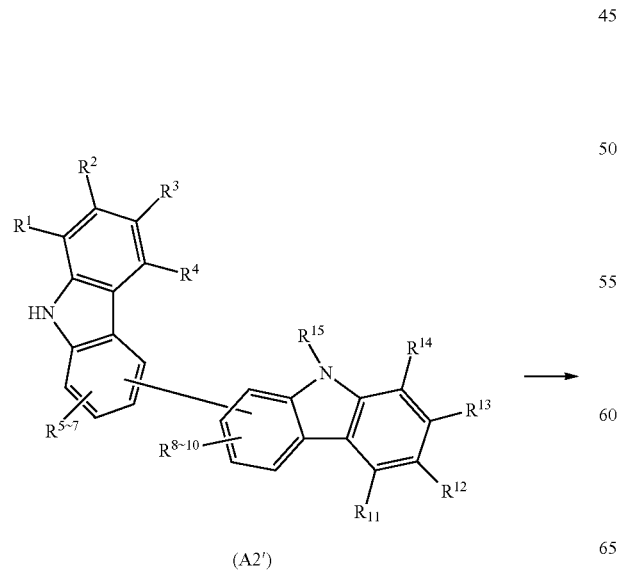

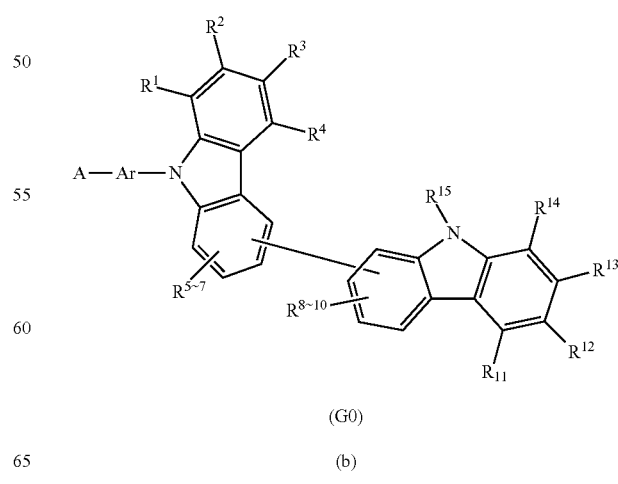

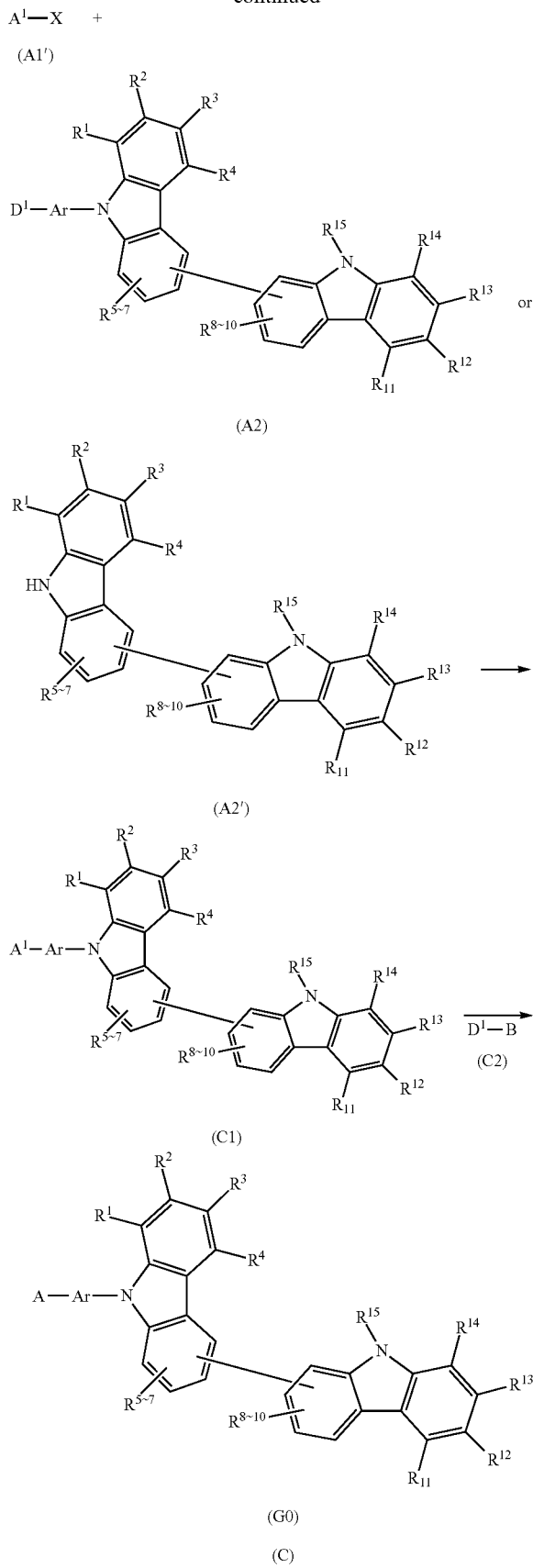

X in the formula represents a halogen element. $D^1$ represents a boronic acid, a boronic ester, a cyclic-triolborate salt, or the like. As the cyclic-triolborate salt, a lithium salt, a potassium salt, or a sodium salt may be used. $A^1$ represents a compound in which a halogen element is bonded to a substituted or unsubstituted benzofuropyrimidine skeleton or a substituted or unsubstituted benzothienopyrimidine skeleton. B represents a derivative including one condensed ring or two condensed rings. A represents a benzofuropyrimidine skeleton or a benzothienopyrimidine skeleton that includes at least a substituent including one condensed ring or two condensed rings, and Ar represents a substituted or unsubstituted arylene group having 6 to 25 carbon atoms, or a single bond.

A variety of the above compounds (A1), (A1'), (A2), (A2'), (B1), (B2), (C1), and (C2) are commercially available or can be obtained by synthesis, which means that various types of the bicarbazole compound represented by General Formula (G0) can be synthesized. Thus, there are various examples of the organic compound of one embodiment of the present invention.

The above is the description of the example of a method for synthesizing the bicarbazole compound of one embodiment of the present invention; however, the present invention is not limited thereto and various synthesis methods may be employed.

Embodiment 3

In this embodiment, structure examples of light-emitting elements including the organic compound of one embodiment of the present invention are described below with reference to FIGS. 1A to 1C and FIGS. 2A and 2B.

FIG. 1A is a cross-sectional view of a light-emitting element 150 of one embodiment of the present invention. The light-emitting element 150 includes at least a pair of electrodes (an electrode 101 and an electrode 102) and an EL layer 100 provided between the pair of electrodes.

The EL layer 100 includes at least a light-emitting layer 130. In addition, the EL layer 100 includes functional layers such as a hole-injection layer 111, a hole-transport layer 112, an electron-transport layer 118, and an electron-injection layer 119.

Although description is given assuming that the electrode 101 serves as an anode and the electrode 102 serves as a cathode in this embodiment, the structure of the light-emitting element is not limited thereto. That, is, it is possible that the electrode 101 serves as a cathode and the electrode 102 serves as an anode. In that case, the stacking order of layers is reversed. In other words, the hole-injection layer, the hole-transport layer, the light-emitting layer, the electron-transport layer, and the electron-injection layer may be stacked in this order from the anode side.

The structure of the EL layer 100 is not limited to the above, and the EL layer 100 may include a functional layer that is capable of improving or inhibiting a hole- or electron-transport property, or suppressing diffusion of excitons, for example. The functional layers may each be a single layer or stacked layers.

In the light-emitting element 150, at least one of the layers in the EL layer 100 contains the organic compound of one embodiment of the present invention. The organic compound is contained preferably in the electron-transport layer 118 or the hole-transport layer 112, further preferably in the light-emitting layer 130.

In the case where the organic compound of one embodiment of the present invention is contained in the light-emitting layer 130, the organic compound can be favorably used as a host material because the organic compound has a high hole-transport property and a wide band gap.

The organic compound of one embodiment of the present invention is favorable for a thermally activated delayed fluorescence material because an energy difference between the singlet excitation energy level and the triplet excitation energy level can be small. Accordingly, with use of the compound of one embodiment of the present invention as a light-emitting material, a light-emitting element can have high emission efficiency.

The compound having an excellent carrier-transport property is suitable for a host material or a carrier-transport material in a light-emitting element. Thus, the structure of this embodiment can provide a light-emitting element with low driving voltage.

The compound having an excellent carrier-transport property is suitable for a host material or a carrier-transport material in a light-emitting element.

<Structure Example 1 of Light-Emitting Element>

Figure 1B:
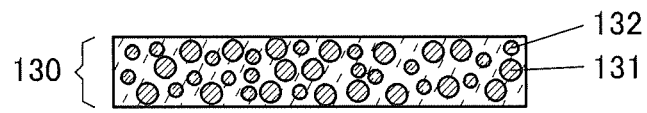

FIG. 1B is a schematic cross-sectional view illustrating an example of the light-emitting layer 130 in FIG. 1A. The light-emitting layer 130 in FIG. 1B includes a material 131 and a host material 132.

The material 131 may be a light-emitting organic material, and the light-emitting organic material is preferably a material capable of emitting fluorescence (hereinafter also referred to as a fluorescent material).

In the light-emitting element 150 of one embodiment of the present invention, voltage application between a pair of electrodes (the electrodes 101 and 102) causes electrons and holes to be injected from the cathode and the anode, respectively, into the EL layer 100 and thus current flows. By recombination of the injected electrons and holes, excitons are formed. The ratio of singlet excitons to triplet excitons (hereinafter referred to as exciton generation probability) which are generated by carrier (electrons and holes) recombination is approximately 1:3 according to the statistically obtained probability. Accordingly, in a light-emitting element that uses a fluorescent material, the probability of generation of singlet excitons, which contribute to light emission, is 25% and the probability of generation of triplet excitons, which do not contribute to light emission, is 75%. Therefore, converting the triplet excitons, which do not contribute to light emission, into singlet excitons, which contribute to light emission, is important for increasing the emission efficiency of the light-emitting element.

For this reason, the material 131 preferably has a function of converting a triplet exciton into a singlet exciton by reverse intersystem crossing. Accordingly, the material 131 is preferably a thermally activated delayed fluorescence material. That is, the compound of one embodiment of the present invention which has a bicarbazole skeleton and a benzofuropyrimidine skeleton or a benzothienopyrimidine skeleton can be used as the material 131.

A difference between the singlet excitation energy level and the triplet excitation energy level of the material 131 is preferably greater than 0 eV and less than or equal to 0.3 eV, more preferably greater than 0 eV and less than or equal to 0.2 eV, further more preferably greater than 0 eV and less than or equal to 0.1 eV.

Figure 1C:
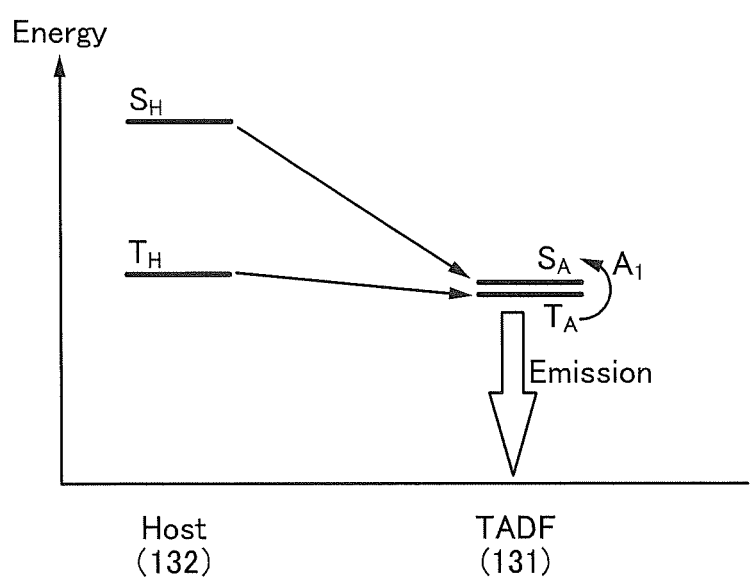

FIG. 1C shows the correlation of energy levels of the material 131 and the host material 132 in the light-emitting layer 130. The following explains what the teams and signs in FIG. 1C represent:

TADF (131): the material 131;
Host (132): the host material 132;
$S_A$: the S1 level of the material 131;
$T_A$: the T1 level of the material 131;
$S_H$: the S1 level of the host material 132; and
$T_H$: the T1 level of the host material 132.

In the case where carriers are recombined in the light-emitting layer 130 and the singlet excited state and the triplet excited state of the host material 132 are formed, energy of the singlet excited state transfers from the S1 level ($S_H$) of the host material 132 to the S1 level ($S_A$) of the material 131, and energy of the triplet excited state transfers from the T1 level ($T_H$) of the host material 132 to the T1 level ($T_A$) of the material 131; thus, the singlet excited state and the triplet excited state of the material 131 are formed.

Alternatively, carriers are recombined in the material 131, and the singlet excited state having excitation energy that corresponds to the S1 level ($S_A$) and the triplet excited state having excitation energy that corresponds to the T1 level ($T_A$) are formed.

In either case, the singlet excited state and the triplet excited state of the material 131 are formed by the carrier recombination.

In the light-emitting element 150 of one embodiment of the present invention, the S1 level ($S_A$) and the T1 level ($T_A$) of the material 131 included in the light-emitting layer 130 are energy levels adjacent to each other.

Since the S1 level ($S_A$) and the T1 level ($T_A$) of the material 131 are adjacent energy levels, the material 131 has a function of converting triplet excitation energy into singlet excitation energy by reverse intersystem crossing (see Route $A_1$ in FIG. 1C). Thus, the triplet excitation energy generated in the light-emitting layer 130 is partly converted into singlet excitation energy by the material 131. For this conversion, the energy difference between the S1 level ($S_A$) and the T1 level ($T_A$) of the material 131 is preferably greater than 0 eV and less than or equal to 0.3 eV. Fluorescence is obtained from the material 131 in the singlet excited state.

To obtain efficient light emission from the singlet excited state of the material 131, the fluorescence quantum yield of the material 131 is preferably high, and specifically, 50% or higher, further preferably 70% or higher, still further preferably 90% or higher.

In order to make reverse intersystem crossing occur efficiently, the T1 level ($T_A$) of the material 131 is preferably lower than the T1 level ($T_H$) of the host material 132. Thus, quenching of the triplet excitation energy of the material 131 caused by the host material 132 is less likely to occur, which causes efficient reverse intersystem crossing in the material 131. In order to obtain efficient light emission in the material 131, the S1 level ($S_A$) of the material 131 is preferably lower than the S1 level ($S_H$) of the host material 132. Thus, transfer of singlet excitation energy from the material 131 to the host material 132 can be suppressed.

The material 131 preferably has the bicarbazole skeleton that has a strong donor property, in which case a hole that has been injected to the light-emitting layer 130 is easily injected to the material 131 and easily transported. In addition, the material 131 preferably has the benzofuropyrimidine skeleton or the benzothienopyrimidine skeleton that has a strong acceptor property, in which case an electron that has been injected to the light-emitting layer 130 is easily injected to the material 131 and easily transported. In that case, the host material 132 preferably has a donor skeleton whose donor property is weaker than that of the donor skeleton included in the material 131 and an acceptor skeleton whose acceptor property is weaker than that of the acceptor skeleton included in the material 131. With this structure, reaction for forming an exciplex by the material 131 and the host material 132 can be suppressed.

For example, when the HOMO level of the material 131 is higher than that of the host material 132 and the LUMO level of the material 131 is lower than that of the host material 132, both the electron and the hole which are carriers injected to the light-emitting layer 130 are easily injected to the material 131 and easily transported. Thus, the carrier recombination easily occurs in the material 131, which is preferable.

In the case where the combination of the material 131 and the host material 132 is a combination of a compound having a hole-transport property and a compound having an electron-transport property, the carrier balance can be easily controlled depending on the mixture ratio. Specifically, the weight ratio of the compound having a hole-transport property to the compound having an electron-transport property is preferably within a range of 1:9 to 9:1. Since the carrier balance can be easily controlled with the structure, a carrier recombination region can also be controlled easily.

Note that the light-emitting layer 130 does not necessarily includes the host material 132 as long as the carrier balance in the light-emitting layer 130 can be controlled by only the material 131. Alternatively, the light-emitting layer 130 may include a material in addition to the material 131 and the host material 132 in order to control the carrier balance.

As described above, when the reverse intersystem crossing process of Route $A_1$ efficiently occurs, triplet excitation energy of the material 131 is efficiently converted into singlet excitation energy; thus, the light-emitting element 150 can emit light with high emission efficiency.

When the light-emitting layer 130 has the above-described structure, light emission from the material 131 of the light-emitting layer 130 can be obtained efficiently.

<Structure Example 2 of Light-Emitting Element>

Next, a light-emitting element with a structure different from the above structure is described below with reference to FIGS. 2A and 2B. For details of components in this structure example similar to those in the above-described structures, the above structure examples can be referred to.

Figure 2A:
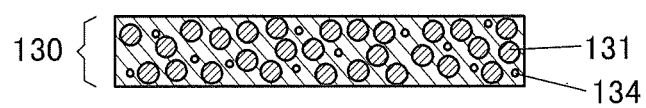
FIGS. 2A and 2B are a schematic cross-sectional view illustrating a light-emitting element of one embodiment of the present invention and a schematic diagram illustrating the correlation of energy levels in a light-emitting layer.

FIG. 2A is a schematic cross-sectional view illustrating an example of the light-emitting layer 130 in FIG. 1A. The light-emitting layer 130 includes the material 131 and a guest material 134.

The guest material 134 may be a light-emitting organic material, and the light-emitting organic material is preferably a material capable of emitting phosphorescence (hereinafter also referred to as a phosphorescent material). A structure in which a fluorescent material is used as the guest material 134 is described below. Note that the guest material 134 may be rephrased as the phosphorescent material.

Figure 2B:
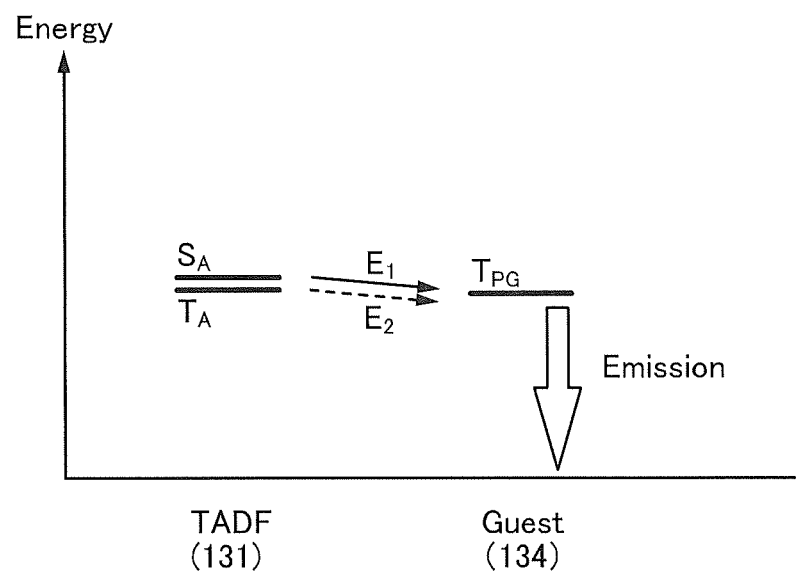

FIG. 2B shows the correlation of energy levels of the material 131 and the guest material 134. The following explains what the terms and signs in FIG. 2B represent:

TADF (131): the material 131;
Guest (134): the guest material 134 (phosphorescent material)
$S_A$: the S1 level of the material 131;
$T_A$: the T1 level of the material 131; and
$T_{PG}$: the T1 level of the guest material 134 (phosphorescent material).

Carriers are recombined in the light-emitting layer 130 and the singlet excited state and the triplet excited state of the material 131 are formed.

By transferring both the singlet excitation energy and the triplet excitation energy of the material 131 to the T1 level ($T_{PG}$) of the guest material 134 (phosphorescent material), light emission can be obtained from the guest material 134 (see Routes $E_1$ and $E_2$ in FIG. 2B).

The T1 level ($T_A$) of the material 131 is preferably higher than the T1 level ($T_{PG}$) of the guest material 134. With such a relation between the T1 levels, the singlet excitation energy and the triplet excitation energy of the material 131 can transfer from the S1 level ($S_A$) and the T1 level ($T_A$) of the material 131 to the T1 level ($T_{PG}$) of the guest material 134.

When the light-emitting layer 130 has the above-described structure, light emission from the guest material 134 (phosphorescent material) of the light-emitting layer 130 can be obtained efficiently.

Note that in the case where carrier recombination occurs in the material 131, the organic compound of one embodiment of the present invention is preferably used as the material 131 in order to reduce the driving voltage of the light-emitting element 150. In this embodiment, the material 131 does not necessarily has high efficiency of reverse intersystem crossing from $T_A$ to $S_A$, and the emission quantum yield from $S_A$ does not need to be high; therefore, the material 131 does not necessarily emit thermally activated delayed fluorescence.

<Material>

Next, components of a light-emitting element of one embodiment of the present invention are described in detail below.

<<Light-Emitting Layer>>

Materials that can be used for the light-emitting layer 130 are described below.

<<Material 131>>

An energy difference between the S1 level and the T1 level of the material 131 is preferably small. Specifically, the energy difference between the S1 level and the T1 level is preferably greater than 0 eV and less than or equal to 0.3 eV, more preferably greater than 0 eV and less than or equal to 0.2 eV, more preferably greater than 0 eV and less than or equal to 0.1 eV. Such a material is, for example, a thermally activated delayed fluorescence material. As the thermally activated delayed fluorescence material, the compound described in Embodiment 1 is favorably used.

Note that the material 131 does not necessarily have a function of emitting thermally activated delayed fluorescence as long as the energy difference between the S1 level and the T1 level is small.

<<Guest Material 134>>

As the guest material 134, an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given.

Examples of the substance that has an emission peak in the blue or green wavelength range include organometallic iridium complexes having a 4H-triazole skeleton, such as tris{2-[5-(2-methylphenyl)-4-(2,6-dimethylphenyl)-4H-1,2,4-triazol-3-yl-κN²]phenyl-κC}iridium(III) (abbreviation: Ir(mpptz-dmp)₃), tris(5-methyl-3,4-diphenyl-4H-1,2,4-triazolato)iridium(III) (abbreviation: Ir(Mptz)₃), tris[4-(3-biphenyl)-5-isopropyl-3-phenyl-4H-1,2,4-triazolato]iridium(III) (abbreviation: Ir(iPrptz-3b)₃), and tris[3-(5-biphenyl)-5-isopropyl-4-phenyl-4H-1,2,4-triazolato]iridium(III) (abbreviation: Ir(iPr5btz)₃); organometallic iridium complexes having a 1H-triazole skeleton, such as tris[3-methyl-1-(2-methylphenyl)-5-phenyl-1H-1,2,4-triazolato]iridium(III) (abbreviation: Ir(Mptz1-mp)$_3$) and tris(1-methyl-5-phenyl-3-propyl-1H-1,2,4-triazolato)iridium(III) (abbreviation: Ir(Prptz1-Me)$_3$); organometallic iridium complexes having an imidazole skeleton, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which a phenylpyridine derivative having an electron-withdrawing group is a ligand, such as bis[2-(4',6'-difluorophenyppyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: Ir(CF$_3$ppy)$_2$(pic)), and bis[2-(4',6'-difluorophenyppyridinato-N,C$^{2'}$]iridium(III) acetylacetonate (abbreviation: FIr(acac)). Among the materials given above, the organometallic iridium complexes having a 4H-triazole skeleton have high reliability and high emission efficiency and are thus especially preferable.

Examples of the substance that has an emission peak in the green or yellow wavelength range include organometallic iridium complexes having a pyrimidine skeleton, such as tris(4-methyl-6-phenylpyrimidinato)iridium(III) (abbreviation: Ir(mppm)$_3$), tris(4-t-butyl-6-phenylpyrimidinato)iridium(III) (abbreviation: Ir(tBuppm)$_3$), (acetylacetonato)bis(6-methyl-4-phenylpyrimidinato)iridium(III) (abbreviation: Ir(mppm)$_2$(acac)), (acetylacetonato)bis(6-tert-butyl-4-phenylpyrimidinato)iridium(III) (abbreviation: Ir(tBuppm)$_2$(acac)), (acetylacetonato)bis[4-(2-norbornyl)-6-phenylpyrimidinato]iridium(III) (abbreviation: Ir(nbppm)$_2$(acac)), (acetylacetonato)bis[5-methyl-6-(2-methylphenyl)-4-phenylpyrimidinato]iridium(III) (abbreviation: Ir(mpmppm)$_2$(acac)), (acetylacetonato)bis{4,6-dimethyl-2-[6-(2,6-dimethylphenyl)-4-pyrimidinyl-κN$^3$]phenyl-κC}iridium(III) (abbreviation: Ir(dmppm-dmp)$_2$(acac)), (acetylacetonato)bis(4,6-diphenylpyrimidinato)iridium(III) (abbreviation: Ir(dppm)$_2$(acac)); organometallic iridium complexes having a pyrazine skeleton, such as (acetylacetonato)bis(3,5-dimethyl-2-phenylpyrazinato)iridium(III) (abbreviation: Ir(mppr-Me)$_2$(acac)) and (acetylacetonato)bis(5-isopropyl-3-methyl-2-phenylpyrazinato)iridium(III) (abbreviation: Ir(mppr-iPr)$_2$(acac)); organometallic iridium complexes having a pyridine skeleton, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C$^{2'}$)iridium(III) (abbreviation: Ir(pq)$_3$), and bis(2-phenylquinolinato-N,C$^{2'}$)iridium(III) acetylacetonate (abbreviation: Ir(pq)$_2$(acac)); organometallic iridium complexes such as bis(2,4-diphenyl-1,3-oxazolato-N,C$^{2'}$)iridium(III) acetylacetonate (abbreviation: Ir(dpo)$_2$(acac)), bis{2-[4'-(perfluorophenyl)phenyl]pyridinato-N, C$^{2'}$}iridium(III) acetylacetonate (abbreviation: Ir(p-PF-ph)$_2$(acac)), and bis(2-phenylbenzothiazolato-N,C$^{2'}$)iridium(III) acetylacetonate (abbreviation: Ir(bt)$_2$(acac)); and a rare earth metal complex such as tris(acetylacetonato)(monophenanthroline)terbium(III) (abbreviation: Tb(acac)$_3$(Phen)). Among the materials given above, the organometallic iridium complexes having a pyrimidine skeleton have distinctively high reliability and emission efficiency and are thus particularly preferable.

Examples of the substance that has an emission peak in the yellow or red wavelength range include organometallic iridium complexes having a pyrimidine skeleton, such as (diisobutyrylmethanato)bis[4,6-bis(3-methylphenyl)pyrimidinato]iridium(III) (abbreviation: Ir(5mdppm)$_2$(dibm)), bis [4,6-bis(3-methylphenyl)pyrimidinato](dipivaloylmethanato)iridium(III) (abbreviation: Ir(5mdppm)$_2$(dpm)), and bis[4,6-di(naphthalen-1-yl)pyrimidinato](dipivaloylmethanato)iridium(III) (abbreviation: Ir(d1npm)$_2$(dpm)); organometallic iridium complexes having a pyrazine skeleton, such as (acetylacetonato)bis(2,3,5-triphenylpyrazinato)iridium(III) (abbreviation: Ir(tppr)$_2$(acac)), bis(2,3,5-triphenylpyrazinato) (dipivaloylmethanato)iridium(III) (abbreviation: Ir(tppr)$_2$(dpm)), and (acetylacetonato)bis[2,3-bis(4-fluorophenyl)quinoxalinato]iridium(III) (abbreviation: Ir(Fdpq)$_2$(acac)); organometallic iridium complexes having a pyridine skeleton, such as tris(1-phenylisoquinolinato-N, C$^{2'}$)iridium(III) (abbreviation: Ir(piq)$_3$) and bis(1-phenylisoquinolinato-N,C$^{2'}$)iridium(III) acetylacetonate (abbreviation: Ir(piq)$_2$(acac)); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(III) (abbreviation: Eu(DBM)$_3$(Phen)) and tris [1-(2-thenoyl)-3,3,3-trifluoroacetonato](monophenanthroline)europium(III) (abbreviation: Eu(TTA)$_3$(Phen)). Among the materials given above, the organometallic iridium complexes having a pyrimidine skeleton have distinctively high reliability and emission efficiency and are thus particularly preferable. Further, the organometallic iridium complexes having a pyrazine skeleton can provide red light emission with favorable chromaticity.

As the light-emitting material included in the light-emitting layer 130, any material can be used as long as the material can convert the triplet excitation energy into light emission. As an example of the material that can convert triplet excitation energy into light emission, a thermally activated delayed fluorescence (TADF) material can be given in addition to the phosphorescent material. Therefore, the term "phosphorescent material" in the description can be replaced with the term "thermally activated delayed fluorescence material". The thermally activated delayed fluorescence material is a material having a small energy difference between the S1 level and the T1 level and has a function of converting the triplet excitation energy into the singlet excitation energy by reverse intersystem crossing. Thus, the thermally activated delayed fluorescence material can up-convert a triplet excited state into a singlet excited state (i.e., reverse intersystem crossing is possible) using a little thermal energy and efficiently exhibit light emission (fluorescence) from the singlet excited state. Conditions for efficiently obtaining thermally activated delayed fluorescence are as follows: the energy difference between the S1 level and the T1 level is preferably greater than 0 eV and less than or equal to 0.3 eV, more preferably greater than 0 eV and less than or equal to 0.2 eV, further more preferably greater than 0 eV and less than or equal to 0.1 eV.

In the case where the thermally activated delayed fluorescence material is composed of one kind of material, any of the following materials can be used, for example.

First, a fullerene, a derivative thereof, an acridine derivative such as proflavine, eosin, and the like can be given. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride, complex (PtCl$_2$(OEP)).

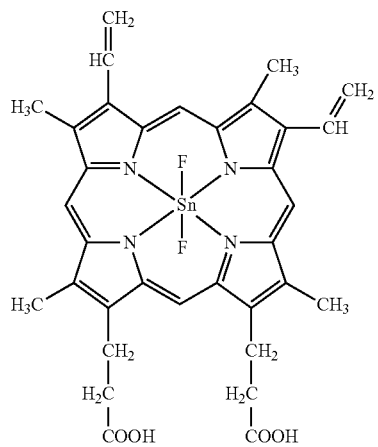

SnF$_2$(Proto IX)

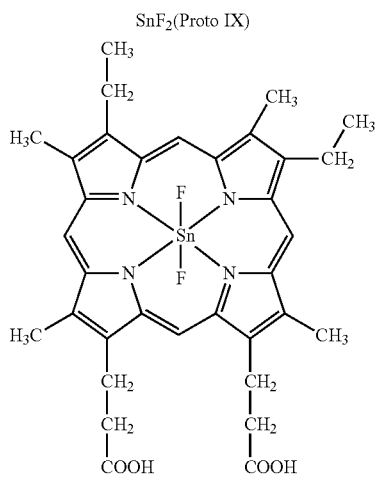

SnF$_2$(Meso IX)

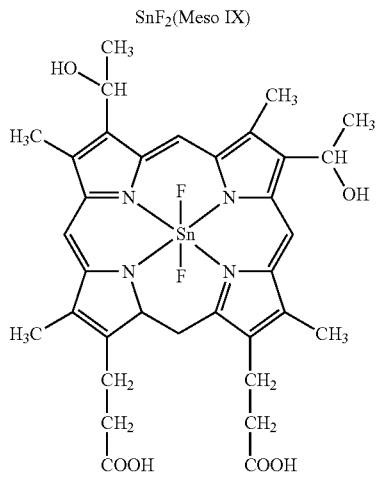

SnF$_2$(Hemato IX)

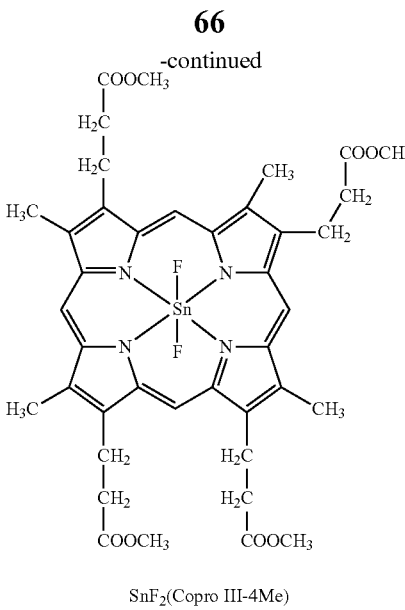

SnF$_2$(Copro III-4Me)

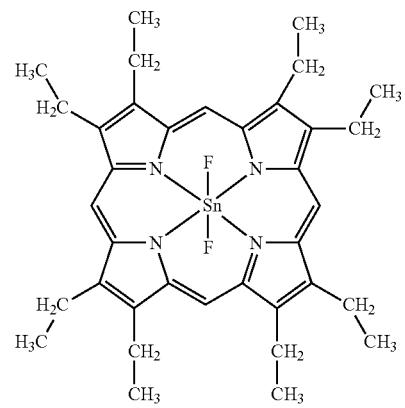

SnF$_2$(OEP)

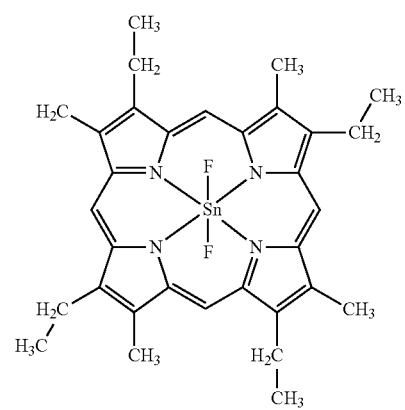

SnF$_2$(Etio I)

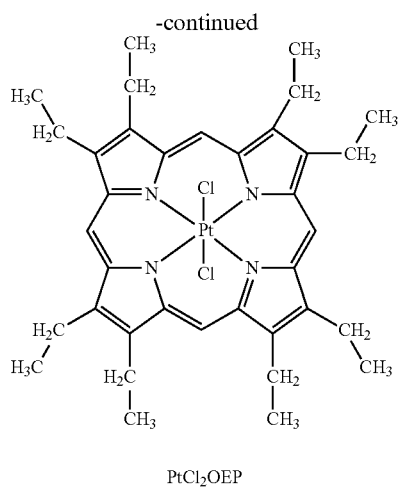

PtCl₂OEP

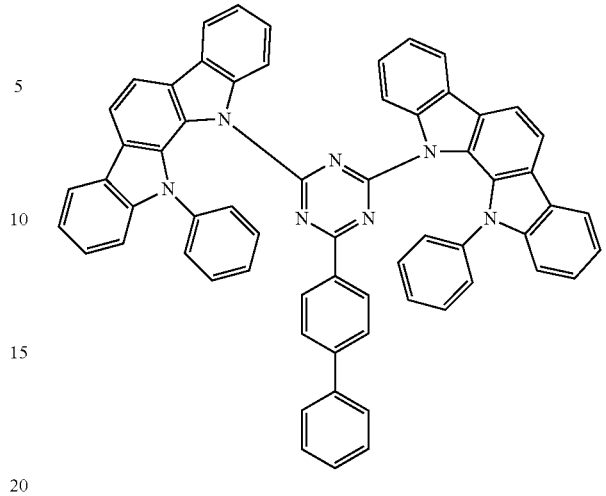

PIC-TRZ

As the thermally activated delayed fluorescence material composed of one kind of material, a heterocyclic compound including a π-electron rich heteroaromatic ring and a π-electron deficient heteroaromatic ring can also be used. Specifically, 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. The heterocyclic compound is preferably used because of having the π-electron rich heteroaromatic ring and the it-electron deficient heteroaromatic ring, for which the electron-transport property and the hole-transport property are high. Among skeletons having the π-electron deficient heteroaromatic ring, a diazine skeleton (a pyrimidine skeleton, a pyrazine skeleton, or a pyridazine skeleton) and a triazine skeleton have stability and high reliability and are particularly preferable. Among skeletons having the π-electron rich heteroaromatic ring, an acridine skeleton, a phenoxazine skeleton, a phenothiazine skeleton, a furan skeleton, a thiophene skeleton, and a pyrrole skeleton have stability and high reliability; therefore, one or more of these skeletons are preferably included. As the pyrrole skeleton, an indole skeleton, a carbazole skeleton, or a 9-phenyl-3,3'-bi-9H-carbazole skeleton is particularly preferred. Note that a substance in which the it-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased and the difference between the level of the singlet excited state and the level of the triplet excited state becomes small.

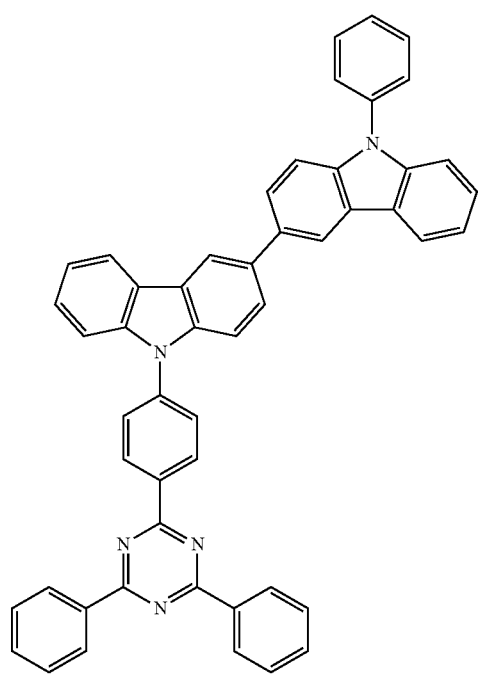

PCCzPTzn

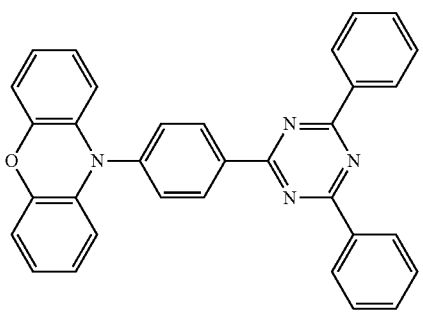

PXZ-TRZ

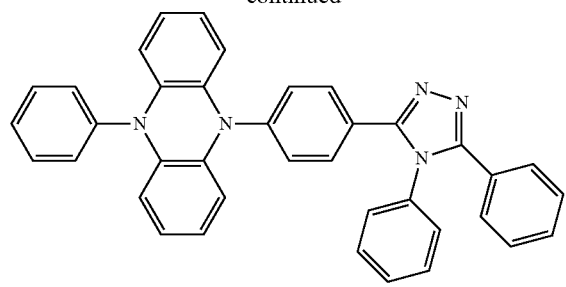

PPZ-3TPT

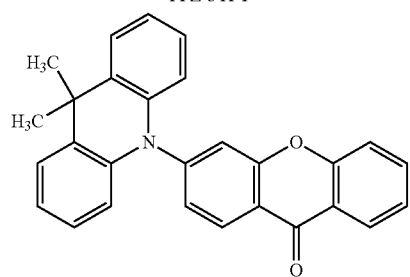

ACRXTN

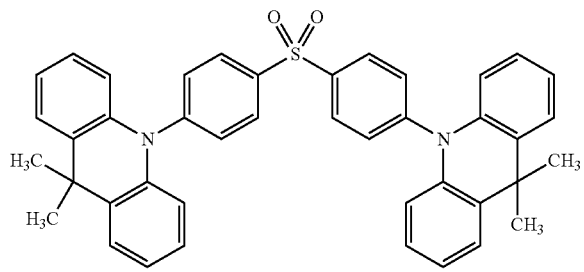

DMAC-DPS

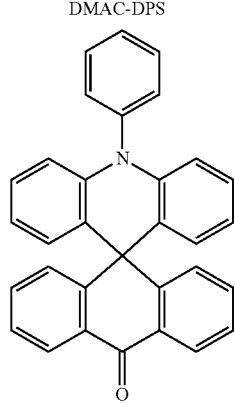

ACRSA

It is preferable that the material 131 and the guest material 134 (the phosphorescent material) be selected such that the emission peak of the material 131 overlaps with an absorption band, specifically an absorption band on the longest wavelength side, of a triplet metal to ligand charge transfer (MLCT) transition of the guest material 134 (the phosphorescent material). This makes it possible to provide a light-emitting element with drastically improved emission efficiency. Note that in the case where a thermally activated delayed fluorescent material is used instead of the phosphorescent material, it is preferable that the absorption band on the longest wavelength side be a singlet absorption band.

Fluorescent materials described below can also be used for the guest material 134. The guest material 134 is preferably, but not particularly limited to, an anthracene derivative, a tetracene derivative, a chrysene derivative, a phenanthrene derivative, a pyrene derivative, a perylene derivative, a stilbene derivative, an acridone derivative, a coumarin derivative, a phenoxazine derivative, a phenothiazine derivative, or the like, and for example, any of the following materials can be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9-phenyl-9H-fluoren-9-yl)phenyl]-N,N'-bis(4-tert-butylphenyl)pyrene-1,6-diamine (abbreviation: 1,6tBu-FLPAPrn), N,N'-diphenyl-N,N'-bis[4-(9-phenyl-9H-fluoren-9-yl)phenyl]-3,8-dicyclohexylpyrene-1, 6-diamine (abbreviation: ch-1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N, 9-triphenylanthracen-9-amine (abbreviation: DPhAPhA), coumarin 6, coumarin 545T, N,N'-diphenylquinacridone (abbreviation: DPQd), rubrene, 2,8-di-tert-butyl-5,11-bis(4-tert-butylphenyl)-6,12-diphenyltetracene (abbreviation: TBRb), Nile red, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tertbutyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinozin-9-yl)ethenyl]-4H-pyran-4-ylidene}propanedinitrile (abbreviation: BisDCJTM), and 5,10,15,20-tetraphenylbisbenzo[5,6]indeno[1,2,3-cd: 1',2',3'-lm]perylene.

It is preferable that the material 131 and the guest material 134 be selected such that the emission peak of the material 131 overlaps with an absorption band on the longest wavelength side (low energy side) of the guest material 134. This makes it possible to provide a light-emitting element with drastically improved emission efficiency.

<<Host material 132>>

Examples of the compound that can be used as the host material 132 are, but not particularly limited to, a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, and a phenanthroline derivative. Other examples are an aromatic amine and a carbazole derivative.

Alternatively, as the host material 132, any of the following hole-transport materials and electron-transport materials can be used. In addition, the organic compound of one embodiment of the present invention can be favorably used.

A material having a property of transporting more holes than electrons can be used as the hole-transport material, and a material having a hole mobility of $1\times10^{-6}$ cm$^2$/Vs or higher is preferable. Specifically, an aromatic amine, a carbazole derivative, an aromatic hydrocarbon, a stilbene derivative, or the like can be used. Furthermore, the hole-transport material may be a high molecular compound.

Examples of the material having a high hole-transport property are aromatic amine compounds such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis (3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole derivative are 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCz1PN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole derivative are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Other examples are pentacene, coronene, and the like. The aromatic hydrocarbon having a hole mobility of $1\times10^{-6}$ cm$^2$/Vs or higher and having 14 to 42 carbon atoms is particularly preferable.

The aromatic hydrocarbon may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Other examples are high molecular compounds such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl) methacrylamide] (abbreviation: PTPDMA), and poly[N,N'-bis(4-butylphenyl)-N,N'-bis(phenyl)benzidine] (abbreviation: poly-TPD).

Examples of the material having a high hole-transport property are aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris[N-(1-naphthyl)-N-phenylamino]triphenylamine (abbreviation: 1'-TNATA), 4,4',4''-tris(N,N'-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino] spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4''-(9-phenyl-9H-carbazol-3-yl) triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N''-triphenyl-N,N',N''-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl]

fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]-spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). Other examples are amine compounds, carbazole compounds, thiophene compounds, furan compounds, fluorene compounds; triphenylene compounds; phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 3,6-di(9H-carbazol-9-yl)-9-phenyl-9H-carbazole (abbreviation: PhCzGI), 2,8-di(9H-carbazol-9-yl)-dibenzothiophene (abbreviation: Cz2DBT), 4-{3-[3-(9-phenyl-9H-fluoren-9-yl)phenyl]phenyl}dibenzofuran (abbreviation: mmDBFFLB 4,4',4"-(benzene-1,3,5-triyl)tri(dibenzofuran) (abbreviation: DBF3P-II), 1,3,5-tri(dibenzothiophen-4-yl)-benzene (abbreviated as DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II). The substances described here are mainly substances having a hole mobility of $1\times10^{-6}$ cm$^2$/Vs or higher. Note that other than these substances, any substance that has a property of transporting more holes than electrons may be used.

As the electron-transport material, a material having a property of transporting more electrons than holes can be used, and a material having an electron mobility of $1\times10^{-6}$ cm$^2$/Vs or higher is preferable. A π-electron deficient heteroaromatic compound such as a nitrogen-containing heteroaromatic compound, a metal complex, or the like can be used as the material that easily accepts electrons (the material having an electron-transport property). Specific examples include a metal complex having a quinoline ligand, a benzoquinoline ligand, an oxazole ligand, or a thiazole ligand, an oxadiazole derivative, a triazole derivative, a phenanthroline derivative, a pyridine derivative, a bipyridine derivative, a pyrimidine derivative, and the like.

Examples include metal complexes having a quinoline or benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq) and bis(8-quinolinolato)zinc(II) (abbreviation: Znq), and the like. Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ) can be used. Other than such metal complexes, any of the following can be used: heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: C011), 3-(4-biphenylyl)-4-phenyl-5-(4-tert-butylphenyl)-1,2,4-triazole (abbreviation: TAZ), 9-[4-(4,5-diphenyl-4H-1,2,4-triazol-3-yl)phenyl]-9H-carbazole (abbreviation: CzTAZ1), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), bathophenanthroline (abbreviation: BPhen), and bathocuproine (abbreviation: BCP); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-[3-(3,9'-bi-9H-carbazol-9-yl)phenyl]dibenzo[f,h]quinoxaline (abbreviation: 2mCzCzPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton such as PCCzPTzn; heterocyclic compounds having a pyridine skeleton such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB); and heteroaromatic compounds such as 4,4'-bis(5-methylbenzoxazol-2-yl)stilbene (abbreviation: BzOs). Among the heterocyclic compounds, the heterocyclic compounds having diazine skeletons (pyrimidine, pyrazine, pyridazine) or having a pyridine skeleton are highly reliable and stable and is thus preferably used. In addition, the heterocyclic compounds having the skeletons have a high electron-transport property to contribute to a reduction in driving voltage. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-pipyridine-6,6'-diyl)] (abbreviation: PF-BPy) can be used. The substances described here are mainly substances having an electron mobility of $1\times10^{-6}$ cm$^2$/Vs or higher. Note that other substances may also be used as long as their electron-transport properties are higher than their hole-transport properties.

The light-emitting layer 130 can have a structure in which two or more layers are stacked. For example, in the case where the light-emitting layer 130 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material.

The light-emitting layer 130 may contain a material other than the material 131, the host material 132, and the guest material 134.

Note that the light-emitting layer 130 can be formed by an evaporation method (including a vacuum evaporation method), an inkjet method, a coating method, gravure printing, or the like. Besides the above-mentioned materials, an inorganic compound such as a quantum dot or a high molecular compound (e.g., an oligomer, a dendrimer, and a polymer) may be used.

Examples of a material of a quantum dot include a Group 14 element, a Group 15 element, a Group 16 element, a compound of a plurality of Group 14 elements, a compound of an element belonging to any of Groups 4 to 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, and semiconductor clusters.

Specific examples include, but are not limited to, cadmium selenide (CdSe); cadmium sulfide (CdS); cadmium telluride (CdTe); zinc selenide (ZnSe); zinc oxide (ZnO); zinc sulfide (ZnS); zinc telluride (ZnTe); mercury sulfide (HgS); mercury selenide (HgSe); mercury telluride (HgTe); indium arsenide (InAs); indium phosphide (InP); gallium arsenide (GaAs); gallium phosphide (GaP); indium nitride (InN); gallium nitride (GaN); indium antimonide (InSb); gallium antimonide (GaSb); aluminum phosphide (AlP); aluminum arsenide (AlAs); aluminum antimonide (AlSb); lead(II) selenide (PbSe); lead(II) telluride (PbTe); lead(II) sulfide (PbS); indium selenide ($In_2Se_3$); indium telluride ($In_2Te_3$); indium sulfide ($In_2S_3$); gallium selenide ($Ga_2Se_3$); arsenic(III) sulfide ($As_2S_3$); arsenic(III) selenide ($As_2Se_3$); arsenic(III) telluride ($As_2Te_3$); antimony(III) sulfide ($Sb_2S_3$); antimony(III) selenide ($Sb_2Se_3$); antimony(III) telluride ($Sb_2Te_3$); bismuth(III) sulfide ($Bi_2S_3$); bismuth(III) selenide ($Bi_2Se_3$); bismuth(III) telluride ($Bi_2Te_3$); silicon (Si); silicon carbide (SiC); germanium (Ge); tin (Sn); selenium (Se); tellurium (Te); boron (B); carbon (C); phosphorus (P); boron nitride (BN); boron phosphide (BP); boron arsenide (BAs); aluminum nitride (AlN); aluminum sulfide ($Al_2S_3$); barium sulfide (BaS); barium selenide (BaSe); barium telluride (BaTe); calcium sulfide (CaS); calcium selenide (CaSe); calcium telluride (CaTe); beryllium sulfide (BeS); beryllium selenide (BeSe); beryllium telluride (BeTe); magnesium sulfide (MgS); magnesium selenide (MgSe); germanium sulfide (GeS); germanium selenide (GeSe); germanium telluride (GeTe); tin(IV) sulfide ($SnS_2$); tin(II) sulfide (SnS); tin(II) selenide (SnSe); tin(II) telluride (SnTe); lead(II) oxide (PbO); copper(I) fluoride (CuF); copper(I) chloride (CuCl); copper(I) bromide (CuBr); copper(I) iodide (CuI); copper(I) oxide ($Cu_2O$); copper(I) selenide ($Cu_2Se$); nickel(II) oxide (NiO); cobalt(II) oxide (CoO); cobalt(II) sulfide (CoS); triiron tetraoxide ($Fe_3O_4$); iron(II) sulfide (FeS); manganese(II) oxide (MnO); molybdenum(IV) sulfide ($MoS_2$); vanadium(II) oxide (VO); vanadium(IV) oxide ($VO_2$); tungsten(IV) oxide ($WO_2$); tantalum (V) oxide ($Ta_2O_5$); titanium oxide (e.g., $TiO_2$, $Ti_2O_5$, $Ti_2O_3$, or $Ti_5O_9$); zirconium oxide ($ZrO_2$); silicon nitride ($Si_3N_4$); germanium nitride ($Ge_3N_4$); aluminum oxide ($Al_2O_3$); barium titanate ($BaTiO_3$); a compound of selenium, zinc, and cadmium (CdZnSe); a compound of indium, arsenic, and phosphorus (InAsP); a compound of cadmium, selenium, and sulfur (CdSeS); a compound of cadmium, selenium, and tellurium (CdSeTe); a compound of indium, gallium, and arsenic (InGaAs); a compound of indium, gallium, and selenium (InGaSe); a compound of indium, selenium, and sulfur (InSeS); a compound of copper, indium, and sulfur (e.g., $CuInS_2$); and combinations thereof. What is called an alloyed quantum dot, whose composition is represented by a given ratio, may be used. For example, an alloyed quantum dot represented by $CdS_xSe_{1-x}$ (where x is any number between 0 and 1 inclusive) is a means effective in obtaining blue light because the emission wavelength can be changed by changing x.

As the quantum dot, any of a core-type quantum dot, a core-shell quantum dot, a core-multishell quantum dot, and the like can be used. Note that when a core is covered with a shell formed of another inorganic material having a wider band gap, the influence of defects and dangling bonds existing at the surface of a nanocrystal can be reduced. Since such a structure can significantly improve the quantum efficiency of light emission, it is preferable to use a core-shell or core-multishell quantum dot. Examples of the material of a shell include zinc sulfide (ZnS) and zinc oxide (ZnO).

Quantum dots have a high proportion of surface atoms and thus have high reactivity and easily cohere together. For this reason, it is preferable that a protective agent be attached to, or a protective group be provided at the surfaces of quantum dots. The attachment of the protective agent or the provision of the protective group can prevent cohesion and increase solubility in a solvent. It can also reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxyethylene n-nonylphenyl ether; tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolines; aminoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

The quantum dots may be quantum rods, which are rod-like shape quantum dots. A quantum rod emits directional light polarized in the c-axis direction; thus, quantum rods can be used as a light-emitting material to obtain a light-emitting element with higher external quantum efficiency. Alternatively, the quantum dots may have a perovskite structure.

In the case of using quantum dots as the light-emitting material in the light-emitting layer, the thickness of the light-emitting layer is set to 3 nm to 100 nm, preferably 10 nm to 100 nm, and the light-emitting layer is made to contain 1 volume % to 100 volume % of the quantum dots. Note that it is preferable that the light-emitting layer be composed of the quantum dots. To form a light-emitting layer in which the quantum dots are dispersed as light-emitting materials in host materials, the quantum dots may be dispersed in the host materials, or the host materials and the quantum dots may be dissolved or dispersed in an appropriate liquid medium, and then a wet process (e.g., a spin coating method, a casting method, a die coating method, blade coating method, a roll coating method, an ink jet method, a printing method, a spray coating method, a curtain coating method, or a Langmuir-Blodgett method) may be employed.

An example of the liquid medium used for the wet process is an organic solvent of ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); dimethyl sulfoxide (DMSO); or the like.

<<Hole-Injection Layer>>

The hole-injection layer 111 has a function of reducing a barrier for hole injection from one of the pair of electrodes (the electrode 101 or the electrode 102) to promote hole injection and is formed using a transition metal oxide, a phthalocyanine derivative, or an aromatic amine, for example. As the transition metal oxide, molybdenum oxide, vanadium oxide, ruthenium oxide, tungsten oxide, manganese oxide, or the like can be given. As the phthalocyanine derivative, phthalocyanine, metal phthalocyanine, or the like can be given. As the aromatic amine, a benzidine derivative, a phenylenediamine derivative, or the like can be given. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron accepting property and a layer containing a hole-transport material may also be used. In a steady state or in the presence of an electric field, electric charge can be transferred between these materials. As examples of the material having an electron-accepting property, organic acceptors such as a quinodimethane derivative, a chloranil derivative, and a hexaazatriphenylene derivative can be given. A specific example is a compound having an electron-withdrawing group (a halogen group or a cyano group), such as 7,7,8,8-tetracyano-2,3,5,6-tetrafluoroquinodimethane (abbreviation: $F_4$-TCNQ), chloranil, or 2,3,6,7,10,11-hexacyano-1,4,5,8,9,12-hexaazatriphenylene (abbreviation: HAT-CN). Alternatively, a transition metal oxide such as an oxide of a metal from Group 4 to Group 8 can also be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because it is stable in the air, has a low hygroscopic property, and is easily handled.

A material having a property of transporting more holes than electrons can be used as the hole-transport material, and a material having a hole mobility of $1\times10^{-6}$ cm$^2$/Vs or higher is preferable. Specifically, any of the aromatic amine, carbazole derivative, aromatic hydrocarbon, stilbene derivative, and the like described as examples of the hole-transport material that can be used in the light-emitting layer 130 can be used. Furthermore, the hole-transport material may be a high molecular compound.

<<Hole-Transport Layer>>

The hole-transport layer 112 is a layer containing a hole-transport material and can be formed using any of the hole-transport materials given as examples of the material of the hole-injection layer 111. In order that the hole-transport layer 112 has a function of transporting holes injected into the hole-injection layer 111 to the light-emitting layer 130, the HOMO level of the hole-transport layer 112 is preferably equal or close to the HOMO level of the hole-injection layer 111.

As the hole-transport material, a substance having a hole mobility of $1\times10^{-6}$ cm$^2$/Vs or higher is preferably used. Note that any substance other than the above substances may be used as long as the hole-transport property is higher than the electron-transport property. The layer including a substance having a high hole-transport property is not limited to a single layer, and two or more layers containing the aforementioned substances may be stacked.

<<Electron-Transport Layer>>

The electron-transport layer 118 has a function of transporting, to the light-emitting layer 130, electrons injected from the other of the pair of electrodes (the electrode 101 or the electrode 102) through the electron-injection layer 119. A material having a property of transporting more electrons than holes can be used as the electron-transport material, and a material having an electron mobility of $1\times10^{-6}$ cm$^2$/Vs or higher is preferable. As the compound which easily accepts electrons (the material having an electron-transport property), a π-electron deficient heteroaromatic compound such as a nitrogen-containing heteroaromatic compound, a metal complex, or the like can be used, for example. Specifically, a metal complex having a quinoline ligand, a benzoquinoline ligand, an oxazole ligand, or a thiazole ligand, which is described as the electron-transport material that can be used in the light-emitting layer 130, can be given. In addition, an oxadiazole derivative, a triazole derivative, a phenanthroline derivative, a pyridine derivative, a bipyridine derivative, a pyrimidine derivative, and the like can be given. A substance having an electron mobility of $1\times10^{-6}$ cm$^2$/Vs or higher is preferable. Note that other than these substances, any substance that has a property of transporting more electrons than holes may be used for the electron-transport layer. The electron-transport layer 118 is not limited to a single layer, and may include stacked two or more layers containing the aforementioned substances.

Between the electron-transport layer 118 and the light-emitting layer 130, a layer that controls transfer of electron carriers may be provided. The layer that controls transfer of electron carriers is a layer formed by addition of a small amount of a substance having a high electron-trapping property to a material having a high electron-transport property described above, and the layer is capable of adjusting carrier balance by suppressing transfer of electron carriers. Such a structure is very effective in preventing a problem (such as a reduction in element lifetime) caused when electrons pass through the light-emitting layer.

An n-type compound semiconductor may also be used, and an oxide such as titanium oxide ($TiO_2$), zinc oxide (ZnO), silicon oxide ($SiO_2$), tin oxide ($SnO_2$), tungsten oxide ($WO_3$), tantalum oxide ($Ta_2O_5$), barium titanate (BaTiO$_3$), barium zirconate (BaZrO$_3$), zirconium oxide ($ZrO_2$), hafnium oxide ($HfO_2$), aluminum oxide ($Al_2O_3$), yttrium oxide ($Y_2O_3$), or zirconium silicate ($ZrSiO_4$); a nitride such as silicon nitride ($Si_3N_4$); cadmium sulfide (CdS); zinc selenide (ZnSe); or zinc sulfide (ZnS) can be used, for example.

<<Electron-Injection Layer>>

The electron-injection layer 119 has a function of reducing a barrier for electron injection from the electrode 102 to promote electron injection and can be formed using a Group 1 metal or a Group 2 metal, or an oxide, a halide, or a carbonate of any of the metals, for example. Alternatively, a composite material containing an electron-transport material (described above) and a material having a property of donating electrons to the electron-transport material can also be used. As the material having an electron-donating property, a Group 1 metal, a Group 2 metal, an oxide of any of the metals, or the like can be given. Specifically, an alkali metal, an alkaline earth metal, or a compound thereof, such as lithium fluoride (LiF), sodium fluoride (NaF), cesium fluoride (CsF), calcium fluoride (CaF$_2$), or lithium oxide (LiO$_x$), can be used. Alternatively, a rare earth metal compound like erbium fluoride (ErF$_3$) can be used. Electride may also be used for the electron-injection layer 119. Examples of the electride include a substance in which electrons are added at high concentration to calcium oxide-aluminum oxide. The electron-injection layer 119 can be formed using the substance that can be used for the electron-transport layer 118.

A composite material in which an organic compound and an electron donor (donor) are mixed may also be used for the electron-injection layer 119. Such a composite material is excellent in an electron-injection property and an electron-transport property because electrons are generated in the organic compound by the electron donor. In this case, the organic compound is preferably a material that is excellent in transporting the generated electrons. Specifically, the above-listed substances for forming the electron-transport layer 118 (e.g., the metal complexes and heteroaromatic compounds) can be used, for example. As the electron donor, a substance showing an electron-donating property with respect to the organic compound may be used. Specifically, an alkali metal, an alkaline earth metal, and a rare earth metal are preferable, and lithium, sodium, cesium, magnesium, calcium, erbium, and ytterbium are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that the light-emitting layer, the hole-injection layer, the hole-transport layer, the electron-transport layer, and the electron-injection layer described above can each be formed by an evaporation method (including a vacuum evaporation method), an inkjet method, a coating method, a gravure printing method, or the like. Besides the above-mentioned materials, an inorganic compound such as a quantum dot or a high molecular compound (e.g., an oligomer, a dendrimer, and a polymer) may be used in the light-emitting layer, the hole-injection layer, the hole-transport layer, the electron-transport layer, and the electron-injection layer.

<<Pair of Electrodes>>

The electrodes 101 and 102 function as an anode and a cathode of each light-emitting element. The electrodes 101 and 102 can be formed using a metal, an alloy, or a conductive compound, a mixture or a stack thereof, or the like.

One of the electrode 101 and the electrode 102 is preferably formed using a conductive material having a function of reflecting light. Examples of the conductive material include aluminum (Al), an alloy containing Al, and the like. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, it is possible to reduce costs for manufacturing a light-emitting element with aluminum. Alternatively, Ag, an alloy of silver (Ag) and N (N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), or gold (Au)), or the like can be used. Examples of the alloy containing silver include an alloy containing silver, palladium, and copper, an alloy containing silver and copper, an alloy containing silver and magnesium, an alloy containing silver and nickel, an alloy containing silver and gold, an alloy containing silver and ytterbium, and the like. Besides, a transition metal such as tungsten, chromium (Cr), molybdenum (Mo), copper, or titanium can be used.

Light emitted from the light-emitting layer is extracted through the electrode 101 and/or the electrode 102. Thus, at least one of the electrode 101 and the electrode 102 is preferably formed using a conductive material having a function of transmitting light. As the conductive material, a conductive material having a visible light transmittance higher than or equal to 40% and lower than or equal to 100%, preferably higher than or equal to 60% and lower than or equal to 100%, and a resistivity lower than or equal to $1\times10^{-2}$ Ω·cm can be used.

The electrodes 101 and 102 may each be formed using a conductive material having functions of transmitting light and reflecting light. As the conductive material, a conductive material having a visible light reflectivity higher than or equal to 20% and lower than or equal to 80%, preferably higher than or equal to 40% and lower than or equal to 70%, and a resistivity lower than or equal to $1\times10^{-2}$ Ω·cm can be used. For example, one or more kinds of conductive metals and alloys, conductive compounds, and the like can be used. Specifically, a metal oxide such as indium tin oxide (hereinafter, referred to as ITO), indium tin oxide containing silicon or silicon oxide (ITSO), indium oxide-zinc oxide (indium zinc oxide), indium oxide-tin oxide containing titanium, indium titanium oxide, or indium oxide containing tungsten oxide and zinc oxide can be used. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and ytterbium (Yb), or the like can be used.

In this specification and the like, as the material transmitting light, a material that transmits visible light and has conductivity is used. Examples of the material include, in addition to the above-described oxide conductor typified by an ITO, an oxide semiconductor and an organic conductor containing an organic substance. Examples of the organic conductive containing an organic substance include a composite material in which an organic compound and an electron donor (donor material) are mixed and a composite material in which an organic compound and an electron acceptor (acceptor material) are mixed. Alternatively, an inorganic carbon-based material such as graphene may be used. The resistivity of the material is preferably lower than or equal to $1\times10^{5}$ Ω·cm, further preferably lower than or equal to $1\times10^{4}$ Ω·cm.

Alternatively, the electrode 101 and/or the electrode 102 may be formed by stacking two or more of these materials.

Furthermore, to increase light extraction efficiency, a material having a higher refractive index than an electrode that has a function of transmitting light may be formed in contact with the electrode. Such a material may be a conductive material or a non-conductive material as long as having a function of transmitting visible light. For example, in addition to the above-described oxide conductor, an oxide semiconductor and an organic material are given as examples. As examples of the organic material, materials of the light-emitting layer, the hole-injection layer, the hole-transport layer, the electron-transport layer, and the electron-injection layer are given. Alternatively, an inorganic carbon-based material or a metal thin film that allows transmission of light can be used. A plurality of layers each of which is formed using the material having a high refractive index and has a thickness of several nanometers to several tens of nanometers may be stacked.

In the case where the electrode 101 or the electrode 102 functions as the cathode, the electrode preferably contains a material having a low work function (lower than or equal to 3.8 eV). The examples include an element belonging to Group 1 or 2 of the periodic table (e.g., an alkali metal such as lithium, sodium, or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, an alloy containing aluminum and silver, and the like.

In the case where the electrode 101 or the electrode 102 is used as an anode, a material having a high work function (higher than or equal to 4.0 eV) is preferably used.

Alternatively, the electrodes 101 and 102 may each be a stack of a conductive material having a function of reflecting light and a conductive material having a function of transmitting light. In that case, the electrodes 101 and 102 can each have a function of adjusting the optical path length so that desired light emitted from each light-emitting layer resonates and is intensified; thus, such a structure is preferable.

As the method for forming the electrode 101 and the electrode 102, a sputtering method, an evaporation method, a printing method, a coating method, a molecular beam epitaxy (MBE) method, a CVD method, a pulsed laser deposition method, an atomic layer deposition (ALD) method, or the like can be used as appropriate.

<<Substrate>>

A light-emitting element in one embodiment of the present invention may be formed over a substrate of glass, plastic, or the like. As the way of stacking layers over the substrate, layers may be sequentially stacked from the electrode 101 side or sequentially stacked from the electrode 102 side.

For the substrate over which the light-emitting element of one embodiment of the present invention can be formed, glass, quartz, plastic, or the like can be used, for example. Alternatively, a flexible substrate can be used. The flexible substrate means a substrate that can be bent, such as a plastic substrate made of polycarbonate or polyarylate, for example. Alternatively, a film, an inorganic vapor deposition film, or the like can be used. Another material may be used as long as the substrate functions as a support in a manufacturing process of the light-emitting element or an optical element or as long as it has a function of protecting the light-emitting element or an optical element.

In this specification and the like, a light-emitting element can be formed using any of a variety of substrates, for example. There is no particular limitation on the type of substrate. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper which include a fibrous material, a base material film, and the like. As an example of a glass substrate, a barium borosilicate glass substrate, an aluminoborosilicate glass substrate, a soda lime glass substrate, and the like can be given. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a resin such as acrylic. Furthermore, polypropylene, polyester, polyvinyl fluoride, and polyvinyl chloride can be given as examples. Other examples are polyamide, polyimide, aramid, epoxy, an inorganic vapor deposition film, paper, and the like.

Alternatively, a flexible substrate may be used as the substrate such that the light-emitting element is provided directly on the flexible substrate. Further alternatively, a separation layer may be provided between the substrate and the light-emitting element. The separation layer can be used when part or the whole of a light-emitting element formed over the separation layer is separated from the substrate and transferred onto another substrate. In such a case, the light-emitting element can be transferred to a substrate having low heat resistance or a flexible substrate as well. For the above separation layer, a stack including inorganic films, which are a tungsten film and a silicon oxide film, and a structure in which a resin film of polyimide or the like is formed over a substrate can be used, for example.

In other words, after the light-emitting element is formed using a substrate, the light-emitting element may be transferred to another substrate. Example of the substrate to which the light-emitting element is transferred are, in addition to the above substrates, a cellophane substrate, a stone substrate, a wood substrate, a cloth substrate (including a natural fiber (e.g., silk, cotton, and hemp), a synthetic fiber (e.g., nylon, polyurethane, and polyester), a regenerated fiber (e.g., acetate, cupra, rayon, and regenerated polyester), and the like), a leather substrate, a rubber substrate, and the like. When such a substrate is used, a light-emitting element with high durability, high heat resistance, reduced weight, or reduced thickness can be formed.

The light-emitting element 150 may be formed over an electrode electrically connected to a field-effect transistor (FET), for example, which is formed over any of the above-described substrates. Accordingly, an active matrix display device in which the FET controls the driving of the light-emitting element 150 can be manufactured.

The structure described above in this embodiment can be combined with any of the structures described in the other embodiments as appropriate.

Embodiment 4

Figure 3A:
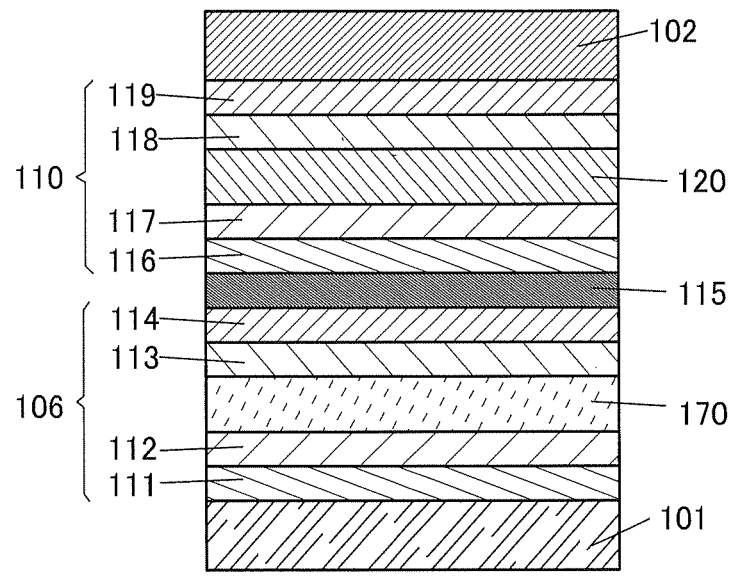
FIGS. 3A to 3C are schematic cross-sectional views illustrating a light-emitting element of one embodiment of the present invention and a schematic diagram illustrating the correlation of energy levels in a light-emitting layer.
Figure 3B:
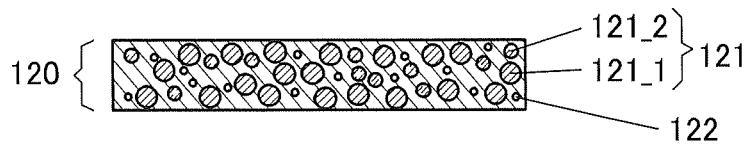

In this embodiment, a light-emitting element having a structure different from that described in Embodiment 3 and light emission mechanisms of the light-emitting elements will be described below with reference to FIGS. 3A to 3C. In FIGS. 3A and 3B, a portion having a function similar to that in FIGS. 1A to 1C is represented by the same hatch pattern as in FIGS. 1A to 1C and not especially denoted by a reference numeral in some cases. In addition, common reference numerals are used for portions having similar functions, and a detailed description of the portions is omitted in some cases.

<Structure Example 3 of Light-Emitting Element>

FIG. 3A is a schematic cross-sectional view of a light-emitting element 250.

The light-emitting element 250 illustrated in FIG. 3A includes a plurality of light-emitting units (a light-emitting unit 106 and a light-emitting unit 110) between a pair of electrodes (the electrode 101 and the electrode 102). One of the light-emitting units preferably has the same structure as the EL layer 100 illustrated in FIG. 1A. That is, it is preferable that the light-emitting element 150 illustrated in FIG. 1A include one light-emitting unit while the light-emitting element 250 include a plurality of light-emitting units. Note that the electrode 101 functions as an anode and the electrode 102 functions as a cathode in the following description of the light-emitting element 250; however, the functions may be interchanged in the light-emitting element 250.

In the light-emitting element 250 illustrated in FIG. 3A, the light-emitting unit 106 and the light-emitting unit 110 are stacked, and a charge-generation layer 115 is provided between the light-emitting unit 106 and the light-emitting unit 110. Note that the light-emitting unit 106 and the light-emitting unit 110 may have the same structure or different structures. For example, it is preferable that a structure similar to that of the EL layer 100 be used in the light-emitting unit 110.

The light-emitting element 250 includes the light-emitting layer 120 and a light-emitting layer 170. The light-emitting unit 106 includes the hole-injection layer 111, the hole-transport layer 112, the electron-transport layer 113, and the electron-injection layer 114 in addition to the light-emitting layer 170. The light-emitting unit 110 includes a hole-injection layer 116, a hole-transport layer 117, an electron-transport layer 118, and an electron-injection layer 119 in addition to the light-emitting layer 120.

The charge-generation layer 115 may have either a structure in which an acceptor substance that is an electron acceptor is added to a hole-transport material or a structure in which a donor substance that is an electron donor is added to an electron-transport material. Alternatively, both of these structures may be stacked.

In the case where the charge-generation layer 115 contains a composite material of an organic compound and an acceptor substance, the composite material that can be used for the hole-injection layer 111 described in Embodiment 3 may be used for the composite material. As the organic compound, a variety of compounds such as an aromatic amine compound, a carbazole compound, an aromatic hydrocarbon, and a high molecular compound (such as an oligomer, a dendrimer, or a polymer) can be used. A material having a hole mobility of $1\times10^{-6}$ cm$^2$/Vs or higher is preferably used as the organic compound. Note that any other material may be used as long as it has a property of transporting more holes than electrons. Since the composite material of an organic compound and an acceptor substance has excellent carrier-injection and carrier-transport properties, low-voltage driving or low-current driving can be realized. Note that when a surface of a light-emitting unit on the anode side is in contact with the charge-generation layer 115, the charge-generation layer 115 can also serve as a hole-injection layer or a hole-transport layer of the light-emitting unit; thus, a hole-injection layer or a hole-transport layer is not necessarily included in the light-emitting unit. Alternatively, when a surface of the light-emitting unit on the cathode side is in contact with the charge-generation layer 115, the charge-generation layer 115 can also serve as an electron-injection layer or an electron-transport layer of the light-emitting unit; thus, an electron-injection layer or an electron-transport layer is not necessarily included in the light-emitting unit.

The charge-generation layer 115 may have a stacked structure of a layer containing the composite material of an organic compound and an acceptor substance and a layer containing another material. For example, the charge-generation layer 115 may be formed using a combination of a layer containing the composite material of an organic compound and an acceptor substance with a layer containing one compound selected from among electron-donating materials and a compound having a high electron-transport property. Furthermore, the charge-generation layer 115 may be formed using a combination of a layer containing the composite material of an organic compound and an acceptor substance with a layer containing a transparent conductive film.

The charge-generation layer 115 provided between the light-emitting unit 106 and the light-emitting unit 110 is configured so that electrons are injected into one of the light-emitting units and holes are injected into the other light-emitting unit when a voltage is applied between the electrode 101 and the electrode 102. For example, in FIG. 3A, the charge-generation layer 115 injects electrons into the light-emitting unit 106 and holes into the light-emitting unit 110 when a voltage is applied such that the potential of the electrode 101 is higher than that of the electrode 102.

Note that in terms of light extraction efficiency, the charge-generation layer 115 preferably has a visible light transmittance (specifically, a visible light transmittance of higher than or equal to 40%). The charge-generation layer 115 functions even when having lower conductivity than the pair of electrodes (the electrodes 101 and 102).

The charge-generation layer 115 formed by using any of the above materials can suppress an increase in driving voltage caused by the stack of the light-emitting layers.

Although FIG. 3A illustrates the light-emitting element including the two light-emitting units, the light-emitting element can include three or more light-emitting units stacked. With a plurality of light-emitting units between a pair of electrodes, which are partitioned by the charge-generation layer as in the light-emitting element 250, it is possible to provide a light-emitting element which can emit high-luminance light with the current density kept low, has a long lifetime, and consumes low power.

Note that in each of the above-described structures, the emission colors of the guest materials used in the light-emitting unit 106 and the light-emitting unit 110 may be the same or different. In the case where guest materials emitting light of the same color are used for the light-emitting unit 106 and the light-emitting unit 110, the light-emitting element 250 can exhibit high emission luminance at a small current value, which is preferable. In the case where guest materials emitting light of different colors are used for the light-emitting unit 106 and the light-emitting unit 110, the light-emitting element 250 can exhibit multi-color light emission, which is preferable. In that case, when a plurality of light-emitting materials with different emission wavelengths are used in one or both of the light-emitting layers 120 and 170, lights with different emission peaks synthesize light emission from the light-emitting element 250. That is, the emission spectrum of the light-emitting element 250 has at least two maximum values.

The above-described structure is also suitable for obtaining white light emission. When the light-emitting layer 120 and the light-emitting layer 170 emit light of complementary colors, white light emission can be obtained. It is particularly favorable to select the guest materials so that white light emission with high color rendering properties or light emission of at least red, green, and blue can be obtained.

Note that when a light-emitting element in which three or more light-emitting units are stacked is used, the emission colors of the guest materials used in the light-emitting units may be the same or different. In the case where a light-emitting element includes light-emitting units that exhibit the same emission color, the emission color of the light-emitting units can have higher light emission luminance at a smaller current value than another emission color of a light-emitting unit. Such a structure is favorably used for adjusting the chromaticity of an emission color. The structure is particularly favorable when guest materials that have different emission efficiency and exhibit different emission colors are used. In the case where a light-emitting element includes three light-emitting units, for example, two light-emitting units containing fluorescent materials of the same color and one light-emitting unit containing a phosphorescent material that emits light of a different color from that of the fluorescent materials can adjust the emission intensity of fluorescence and phosphorescence. That is, the emission intensity of light of each color can be adjusted by the number of light-emitting units.

At least one of the light-emitting layers 120 and 170 may be divided into layers and each of the divided layers may contain a different light-emitting material. That is, at least one of the light-emitting layers 120 and 170 may consist of two or more layers. For example, in the case where the light-emitting layer is formed by stacking a first light-emitting layer and a second light-emitting layer in this order from the hole-transport layer side, the first light-emitting layer is formed using a material having a hole-transport property as the host material and the second light-emitting layer is formed using a material having an electron-transport property as the host material. In that case, a light-emitting material included in the first light-emitting layer may be the same as or different from a light-emitting material included in the second light-emitting layer. In addition, the materials may have functions of emitting light of the same color or light of different colors. White light emission with a high color rendering property that is formed of three primary colors or four or more colors can be obtained by using a plurality of light-emitting materials emitting light of different colors.

In addition, the light-emitting layer of the light-emitting unit 110 preferably contains a phosphorescent compound. When the structure with the organic compound of one embodiment of the present invention is used for at least one of the plurality of units, a light-emitting element with high reliability and high emission efficiency can be provided.

The light-emitting layer 120 included in the light-emitting unit 110 includes a host material 121 and a light-emitting material 122 as illustrated in FIG. 3B. The host material 121 includes an organic compound 121_1 and an organic compound 121_2. In the following description, the light-emitting material 122 included in the light-emitting layer 120 is a phosphorescent compound.

<<Light Emission Mechanism of Light-Emitting Layer 120>>

Next, the light emission mechanism and the material composition of the light-emitting layer 120 are described below.

The organic compound 121_1 and the organic compound 121_2 which are included in the light-emitting layer 120 preferably form an exciplex.

Although it is acceptable as long as the combination of the organic compound 121_1 and the organic compound 121_2 can form an exciplex, it is preferable that one of them be a compound having a hole-transport property and the other be a compound having an electron-transport property.

Figure 3C:
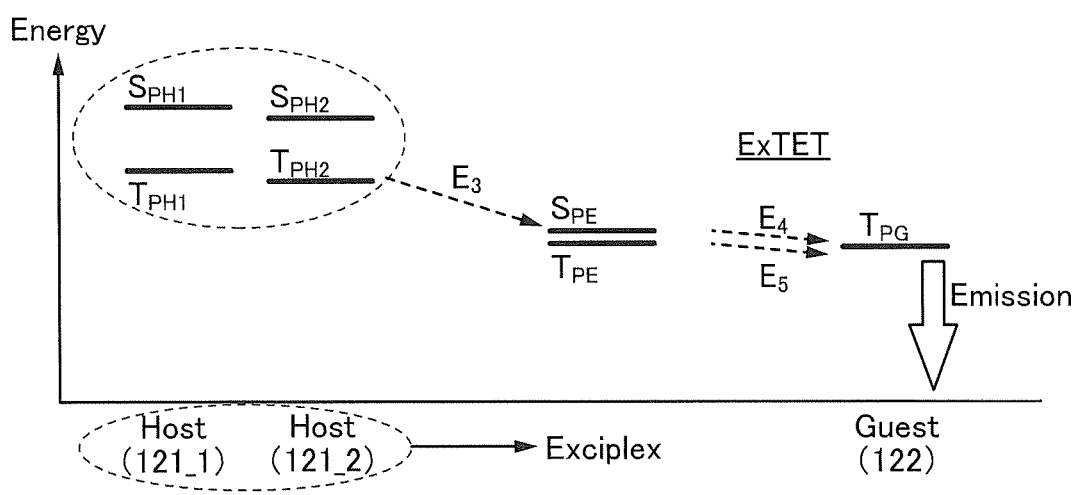

FIG. 3C shows a correlation between the energy levels of the organic compound 121_1, the organic compound 121_2, and the light-emitting material 122 in the light-emitting layer 120. The following explains what terms and numerals in FIG. 3C represent:

Host (121_1): the organic compound 121_1 (host material);

Host (121_2): the organic compound 121_2 (host material);

Guest (122): the light-emitting material 122 (the phosphorescent compound);

$S_{PH1}$: the S1 level of the organic compound 121_1 (host material);

$T_{PH1}$: the T1 level of the organic compound 121_1 (host material);

$S_{PH2}$: the S1 level of the organic compound 121_2 (host material);

$T_{PH2}$: the T1 level of the organic compound 121_2 (host material);

$T_{PG}$: the T1 level of the light-emitting material 122 (the phosphorescent compound);

$S_{PE}$: the S1 level of the exciplex; and $T_{PE}$: the T1 level of the exciplex.

One of the organic compound 121_1 and the organic compound 121_2 receives a hole and the other receives an electron to readily form an exciplex (see Route $E_3$ in FIG. 3C). Alternatively, when one of the organic compounds is brought into an excited state, the other immediately interacts with the one to form an exciplex. Because the excitation energy levels ($S_{PE}$ and $T_{PE}$) of the exciplex are lower than the Si levels ($S_{PH1}$ and $S_{PH2}$) of the host materials (the organic compounds 121_1 and 121_2) that form the exciplex, the excited state of the host material 121 can be formed with lower excitation energy. This can reduce the driving voltage of the light emitting element.

Both energies of $S_{PE}$ and $T_{PE}$ of the exciplex are then transferred to the T1 level of the light-emitting material 122 (the phosphorescent compound); thus, light emission is obtained (see Routes $E_4$ and $E_5$ in FIG. 3C).

Furthermore, the T1 level ($T_{PE}$) of the exciplex is preferably higher than the T1 level ($T_{PG}$) of the light-emitting material 122 and lower than or equal to the T1 levels ($T_{PH1}$ and $T_{PH2}$) of the organic compounds (the organic compound 121_1 and the organic compound 121_2) which form the exciplex. In this way, the singlet excitation energy and the triplet excitation energy of the formed exciplex can be efficiently transferred from the S1 level ($S_{PE}$) and the T1 level ($T_{PE}$) of the exciplex to the T1 level ($T_{PG}$) of the light-emitting material 122.

In order to efficiently form an exciplex by the organic compound 121_1 and the organic compound 121_2, it is preferable to satisfy the following: the HOMO level of one of the organic compound 121_1 and the organic compound 121_2 is higher than that of the other and the LUMO level of the one of the organic compound 121_1 and the organic compound 121_2 is higher than that of the other.

In the case where the combination of the organic compounds 121_1 and 121_2 is a combination of a compound having a hole-transport property and a compound having an electron-transport property, the carrier balance can be easily controlled by adjusting the mixture ratio. Specifically, the weight ratio of the compound having a hole-transport property to the compound having an electron-transport property is preferably within a range of 1:9 to 9:1. Since the carrier balance can be easily controlled with the structure, a carrier recombination region can also be controlled easily.

Note that the above-described processes through Routes $E_3$ to $E_5$ may be referred to as exciplex-triplet energy transfer (ExTET) in this specification and the like. In other words, in the light-emitting layer 120, excitation energy is transferred from the exciplex to the light-emitting material 122. In this case, the efficiency of reverse intersystem crossing from $T_{PE}$ to $S_{PE}$ does not need to be high and the emission quantum yield from $S_{PE}$ do not need to be high either; thus, materials can be selected from a wide range of options.

A light-emitting element with high reliability and emission efficiency can be obtained by utilizing ExTET.

Note that although the example in which the light-emitting layer 120 is a single layer is described in this embodiment for explanation, the light-emitting layer 120 may have a stacked structure of a plurality of light-emitting layers as the light-emitting element described in Embodiment 1. In this case, ExTET is preferably employed for all the phosphorescent light-emitting layers. As a result, a light-emitting element with high luminous efficiency and high reliability can be obtained. The organic compound of one embodiment of the present invention can be favorably used as the organic compound 121_1 or the organic compound 121_2.

The structure described above in this embodiment can be combined with any of the structures described in the other embodiments as appropriate.

Embodiment 5

In this embodiment, a light-emitting device including the light-emitting element described in Embodiment 3 and Embodiment 4 is described with reference to FIGS. 4A and 4B.

FIG. 4A is a top view of the light-emitting device and FIG. 4B is a cross-sectional view taken along the lines A-B and C-D in FIG. 4A. The light-emitting device includes a driver circuit portion (source side driver circuit) 601, a pixel portion 602, and a driver circuit portion (gate side driver circuit) 603, which control light emission of a light-emitting element and are illustrated with dotted lines. Moreover, a reference numeral 604 denotes a sealing substrate, a reference numeral 625 denotes a desiccant, and a reference numeral 605 denotes a sealant. A portion surrounded by the sealant 605 is a space 607.

Note that a lead wiring 608 is a wiring for transmitting signals to be input to the source side driver circuit 601 and the gate side driver circuit 603 and for receiving a video signal, a clock signal, a start signal, a reset signal, and the like from a flexible printed circuit (FPC) 609 functioning as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure of the light-emitting device is described with reference to FIG. 4B. The driver circuit portion and the pixel portion are formed over an element substrate 610. Here, the source side driver circuit 601, which is the driver circuit portion, and one pixel of the pixel portion 602 are illustrated.

In the source side driver circuit 601, a CMOS circuit is formed in which an n-channel TFT 623 and a p-channel TFT 624 are combined. The driver circuit may be formed using various circuits such as a CMOS circuit, a PMOS circuit, or an NMOS circuit. Although a driver-integrated type in which the driver circuit is formed over the substrate is described in this embodiment, the driver circuit is not necessarily formed over the substrate, and may be formed outside the substrate.

The pixel portion 602 includes a plurality of pixels including a switching TFT 611, a current controlling TFT 612, and a first electrode 613 electrically connected to a drain of the current controlling TFT 612. Note that an insulator 614 is formed to cover an end portion of the first electrode 613. The insulator 614 can be formed using a positive photosensitive resin film.

In order to improve coverage with a film that is formed over the insulator 614, the insulator 614 is formed to have a curved surface with curvature at its upper or lower end portion. For example, in the case where photosensitive acrylic is used as a material of the insulator 614, only the upper end portion of the insulator 614 preferably has a curved surface. The radius of curvature of the curved surface is preferably greater than or equal to 0.2 μm and less than or equal to 0.3 μm. As the insulator 614, either a negative photosensitive material or a positive photosensitive material can be used.

An EL layer 616 and a second electrode 617 are formed over the first electrode 613. As a material used for the first electrode 613 which functions as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack including a titanium nitride film and a film containing aluminum as its main component, a stack including three layers of a titanium nitride film, a film containing aluminum as its main component, and a titanium nitride film, or the like can be used. The stacked structure achieves low wiring resistance, a favorable ohmic contact, and a function as an anode.

The EL layer 616 is formed by any of a variety of methods such as an evaporation method using an evaporation mask, an inkjet method, and a spin coating method. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, Ca, or an alloy or a compound thereof, such as MgAg, MgIn, or AlLi) is preferably used. In the case where light generated in the EL layer 616 passes through the second electrode 617, a stack including a thin metal film and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that a light-emitting element 618 is formed with the first electrode 613, the EL layer 616, and the second electrode 617. The light-emitting element 618 preferably has the structure described in Embodiment 3 and Embodiment 4. In the light-emitting device of this embodiment, the pixel portion, which includes a plurality of light-emitting elements, may include both the light-emitting element with the structure described in Embodiment 3 and Embodiment 4 and a light-emitting element with a different structure.

The sealing substrate 604 is attached to the element substrate 610 with the sealant 605, so that the light-emitting element 618 is provided in the space 607 surrounded by the element substrate 610, the sealing substrate 604, and the sealant 605. The space 607 is filled with a filler. The filler may be an inert gas (such as nitrogen or argon), or a resin and/or a desiccant.

An epoxy-based resin or glass frit is preferably used for the sealant 605. It is preferable that such a material do not transmit moisture or oxygen as much as possible. As the sealing substrate 604, a glass substrate, a quartz substrate, or a plastic substrate formed of fiber reinforced plastic (FRP), polyvinyl fluoride (PVF), polyester, acrylic, or the like can be used.

As described above, the light-emitting device including the light-emitting element described in Embodiment 3 and Embodiment 4 can be obtained.

<Structure Example 1 of Light-Emitting Device>

As an example of a light-emitting device, FIGS. 5A and 5B each illustrate a light-emitting device including a light-emitting element exhibiting white light emission and a coloring layer (a color filter).

FIG. 5A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a second electrode 1029 of the light-emitting elements, a sealing substrate 1031, a sealant 1032, and the like.

In FIG. 5A, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 5A, light emitted from some of the light-emitting layers does not pass through the coloring layers, while light emitted from the others of the light-emitting layers passes through the coloring layers. Since light that does not pass through the coloring layers is white and light that passes through any one of the coloring layers is red, blue, or green, an image can be displayed using pixels of the four colors.

FIG. 5B illustrates an example in which the red coloring layer 1034R, the green coloring layer 1034G, and the blue coloring layer 1034B are formed between the gate insulating film 1003 and the first interlayer insulating film 1020. As illustrated in FIG. 5B, the coloring layers may be provided between the substrate 1001 and the sealing substrate 1031.

The above-described light-emitting device has a structure in which light is extracted from the substrate 1001 side where the TFTs are formed (a bottom emission structure), but may have a structure in which light is extracted from the sealing substrate 1031 side (a top emission structure).

<Structure Example 2 of Light-Emitting Device>

Figure 6:
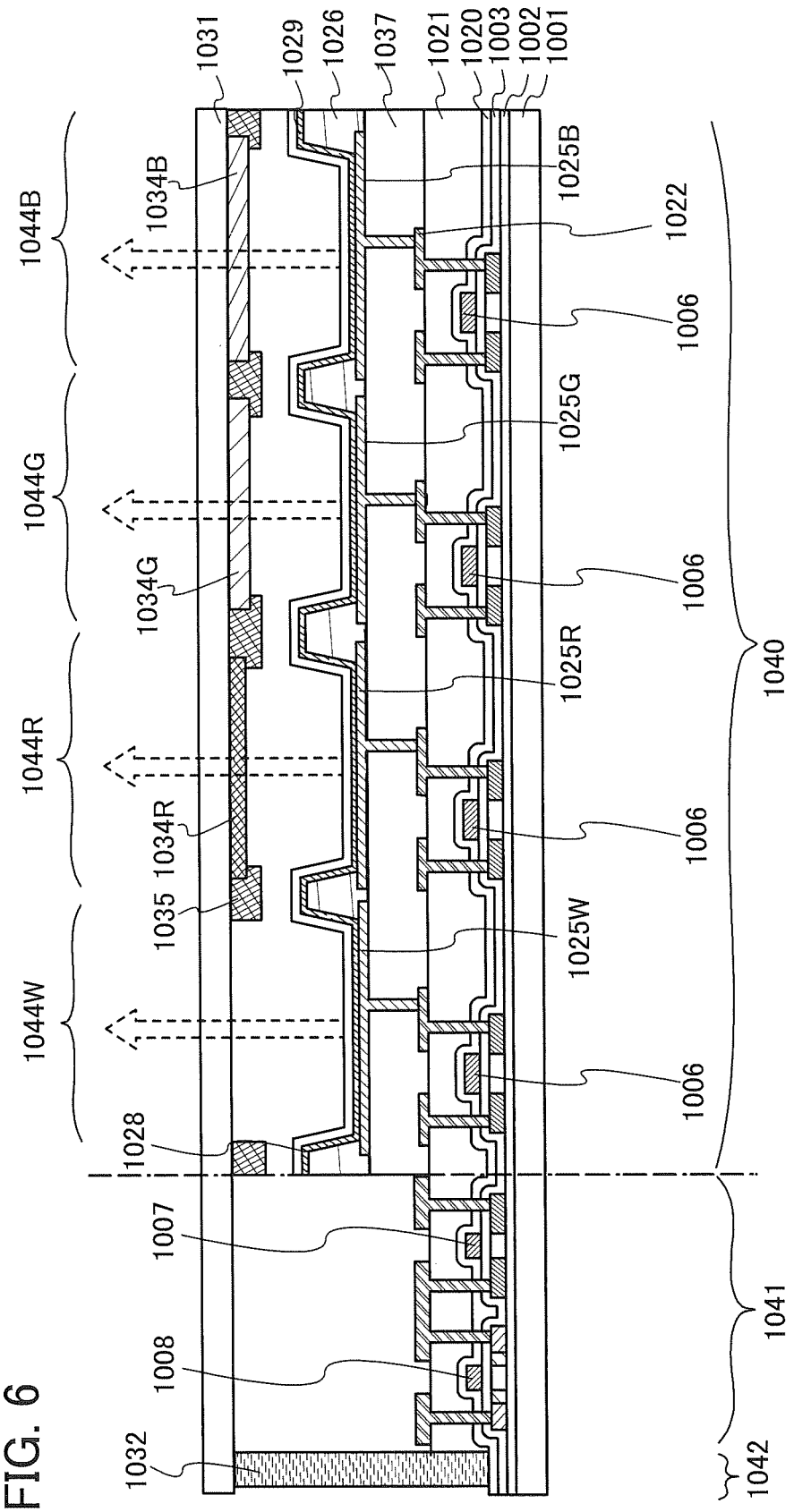
FIG. 6 is a conceptual diagram of an active matrix light-emitting device of one embodiment of the present invention.

FIG. 6 is a cross-sectional view of a light-emitting device having a top emission structure. In this case, a substrate that does not transmit light can be used as the substrate 1001. The process up to the step of forming of a connection electrode which connects the TFT and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film 1021, or can be formed using any other various materials.

Lower electrodes 1025W, 1025R, 1025G, and 1025B of the light-emitting elements each function as an anode here, but may function as a cathode. Furthermore, in the case of the light-emitting device having a top emission structure as illustrated in FIG. 6, the lower electrodes 1025W, 1025R, 1025G, and 1025B are preferably reflective electrodes. Note that the second electrode 1029 preferably has a function of reflecting light and a function of transmitting light. It is preferable that a microcavity structure be used between the second electrode 1029 and the lower electrodes 1025W, 1025R, 1025G, and 1025B, in which case light having a specific wavelength is amplified. The EL layer 1028 is formed to have a structure similar to the structure described in Embodiment 2, with which white light emission can be obtained.

In FIGS. 5A and 5B and FIG. 6, the structure of the EL layer for providing white light emission can be achieved by, for example, using a plurality of light-emitting layers or using a plurality of light-emitting units. Note that the structure to provide white light emission is not limited to the above.

In the case of a top emission structure as illustrated in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with a black layer (the black matrix) which is positioned between pixels. The coloring layers (the red coloring layer 1034R, the green coloring layer 1034G, and the blue coloring layer 1034B) and the black layer (the black matrix) may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

As described above, the light-emitting device including the light-emitting element described in Embodiment 3 and Embodiment 4 can be obtained.

This embodiment can be combined with any of the other embodiments as appropriate.

Embodiment 6

In this embodiment, electronic devices of embodiments of the present invention are described.

According to one embodiment of the present invention, highly reliable electronic devices having flat surfaces can be manufactured. According to one embodiment of the present invention, highly reliable electronic devices having curved surfaces can be manufactured. According to one embodiment of the present invention, flexible and highly reliable electronic devices can be manufactured.

Examples of the electronic devices include a television set, a desktop or laptop personal computer, a monitor of a computer or the like, a digital camera, a digital video camera, a digital photo frame, a mobile phone, a portable game machine, a portable information terminal, an audio reproducing device, and a large game machine such as a pachinko machine.

The light-emitting device of one embodiment of the present invention can achieve high visibility regardless of the intensity of external light. Thus, the light-emitting device of one embodiment of the present invention can be suitably used for a portable electronic device, a wearable electronic device (wearable device), an e-book reader, or the like.

Figure 7A:
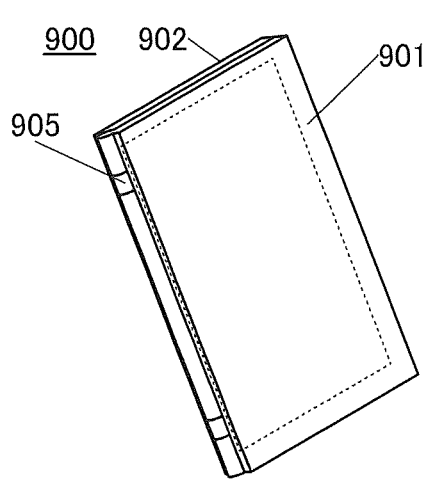
FIGS. 7A to 7D are schematic views of electronic devices of one embodiment of the present invention.
Figure 7B:
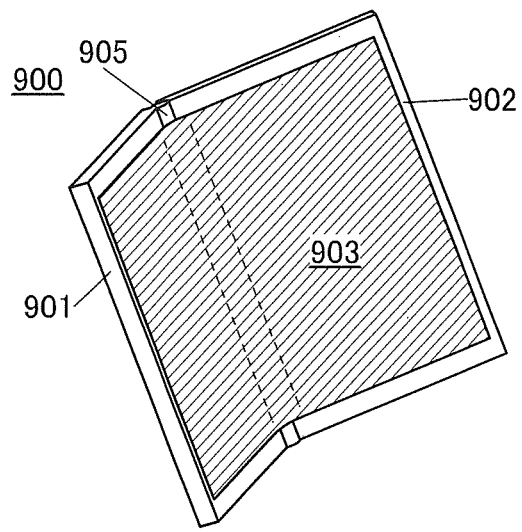

A portable information terminal 900 illustrated in FIGS. 7A and 7B includes a housing 901, a housing 902, a display portion 903, a hinge portion 905, and the like.

The housing 901 and the housing 902 are joined together with the hinge portion 905. The portable information terminal 900 can be opened as illustrated in FIG. 7B from a closed state (FIG. 7A). Thus, the portable information terminal 900 has high portability when carried and excellent visibility when used because of its large display region.

In the portable information terminal 900, the flexible display portion 903 is provided across the housing 901 and the housing 902 which are joined to each other by the hinge portion 905.

The light-emitting device manufactured using one embodiment of the present invention can be used for the display portion 903. Thus, the portable information terminal can be manufactured with high yield.

The display portion 903 can display at least one of a text, a still image, a moving image, and the like. When a text is displayed on the display portion, the portable information terminal 900 can be used as an e-book reader.

When the portable information terminal 900 is opened, the display portion 903 is significantly curved. For example, the display portion 903 is held while including a curved portion with a radius of curvature of greater than or equal to 1 mm and less than or equal to 50 mm, preferably greater than or equal to 5 mm and less than or equal to 30 mm. Part of the display portion 903 can display an image while being bent since pixels are continuously arranged from the housing 901 to the housing 902.

The display portion 903 functions as a touch panel and can be controlled with a finger, a stylus, or the like.

The display portion 903 is preferably formed using one flexible display. Thus, a continuous image can be displayed between the housing 901 and the housing 902. Note that each of the housing 901 and the housing 902 may be provided with a display.

The hinge portion 905 preferably includes a locking mechanism so that an angle formed between the housing 901 and the housing 902 does not become larger than a predetermined angle when the portable information terminal 900 is opened. For example, an angle at which the housing 901 and the housing 902 become locked (they are not opened any further) is preferably greater than or equal to 90° and less than 180° and can be typically 90°, 120°, 135°, 150°, 175°, or the like. In that case, the convenience, safety, and reliability of the portable information terminal 900 can be improved.

When the hinge portion 905 includes a locking mechanism, excessive force is not applied to the display portion 903; thus, breakage of the display portion 903 can be prevented. Therefore, a highly reliable portable information terminal can be provided.

A power button, an operation button, an external connection port, a speaker, a microphone, or the like may be provided for the housing 901 and the housing 902.

Either of the housing 901 and the housing 902 is provided with a wireless communication module, and data can be transmitted and received through a computer network such as the Internet, a local area network (LAN), or Wi-Fi (registered trademark).

Figure 7C:
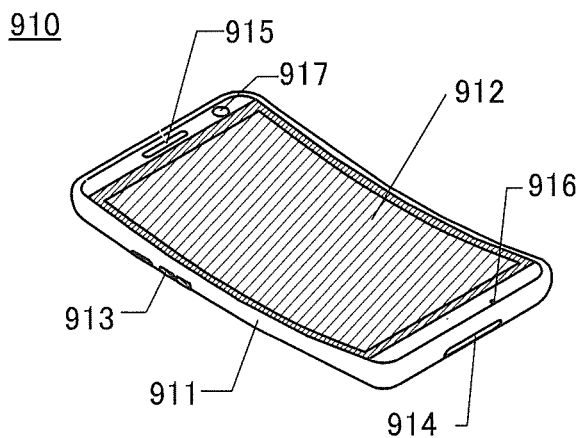

A portable information terminal 910 illustrated in FIG. 7C includes a housing 911, a display portion 912, an operation button 913, an external connection port 914, a speaker 915, a microphone 916, a camera 917, and the like.

The light-emitting device manufactured using one embodiment of the present invention can be used for the display portion 912. Thus, the portable information terminal can be manufactured with high yield.

The portable information terminal 910 includes a touch sensor in the display portion 912. Operations such as making a call and inputting a character can be performed by touch on the display portion 912 with a finger, a stylus, or the like.

With the operation button 913, the power can be turned on or off. In addition, types of images displayed on the display portion 912 can be switched; for example, switching an image from a mail creation screen to a main menu screen is performed with the operation button 913.

When a detection device such as a gyroscope sensor or an acceleration sensor is provided inside the portable information terminal 910, the direction of display on the screen of the display portion 912 can be automatically changed by determining the orientation of the portable information terminal 910 (whether the portable information terminal 910 is placed horizontally or vertically). Furthermore, the direction of display on the screen can be changed by touch on the display portion 912, operation with the operation button 913, sound input using the microphone 916, or the like.

The portable information terminal 910 functions as, for example, one or more of a telephone set, a notebook, and an information browsing system. Specifically, the portable information terminal 910 can be used as a smartphone. The portable information terminal 910 is capable of executing a variety of applications such as mobile phone calls, e-mailing, viewing and editing texts, music reproduction, reproducing a moving image, Internet communication, and computer games, for example.

Figure 7D:
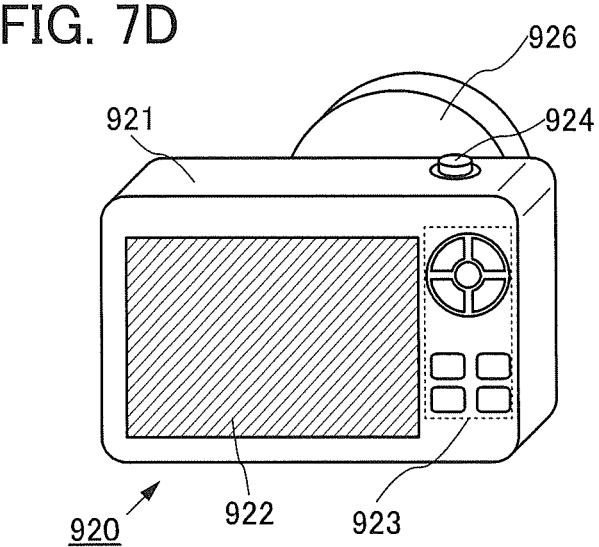

A camera 920 illustrated in FIG. 7D includes a housing 921, a display portion 922, operation buttons 923, a shutter button 924, and the like. Furthermore, an attachable lens 926 is attached to the camera 920.

The light-emitting device manufactured using one embodiment of the present invention can be used for the display portion 922. Thus, the camera can be manufactured with high yield.

Although the lens 926 of the camera 920 here is detachable from the housing 921 for replacement, the lens 926 may be incorporated into the housing 921.

A still image or a moving image can be taken with the camera 920 at the press of the shutter button 924. In addition, images can also be taken by the touch of the display portion 922 which has a function of a touch panel.

Note that a stroboscope, a viewfinder, or the like can be additionally attached to the camera 920. Alternatively, these may be incorporated into the housing 921.

FIGS. 8A to 8E illustrate electronic devices. These electronic devices each include a housing 9000, a display portion 9001, a speaker 9003, an operation key 9005 (including a power switch or an operation switch), a connection terminal 9006, a sensor 9007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone 9008, and the like.

The light-emitting device manufactured using one embodiment of the present invention can be favorably used for the display portion 9001. Thus, the electronic devices can be manufactured with high yield.

The electronic devices illustrated in FIGS. 8A to 8E can have a variety of functions, for example, a function of displaying a variety of information (a still image, a moving image, a text image, and the like) on the display portion, a touch panel function, a function of displaying a calendar, the date, the time, and the like, a function of controlling processing with a variety of software (programs), a wireless communication function, a function of being connected to a variety of computer networks with a wireless communication function, a function of transmitting and receiving a variety of data with a wireless communication function, a function of reading a program or data stored in a storage medium and displaying the program or data on the display portion, and the like. Note that the functions of the electronic devices illustrated in FIGS. 8A to 8E are not limited to the above, and the electronic devices may have other functions.

Figure 8A:
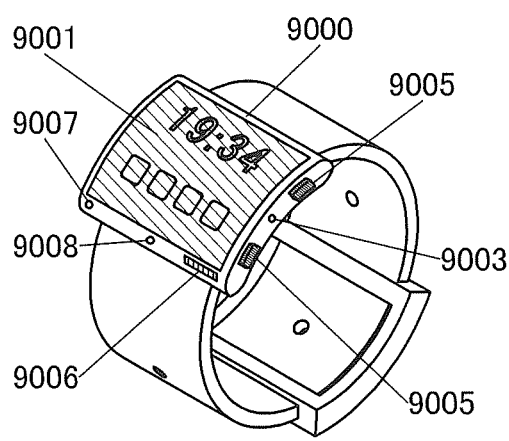
FIGS. 8A to 8E are schematic views of electronic devices of one embodiment of the present invention.
Figure 8B:
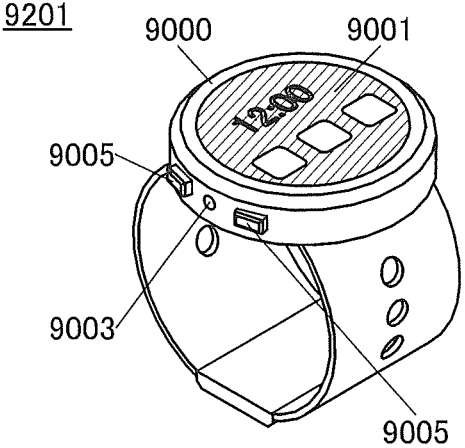

FIG. 8A is a perspective view of a watch-type portable information terminal 9200. FIG. 8B is a perspective view of a watch-type portable information terminal 9201.

The portable information terminal 9200 illustrated in FIG. 8A is capable of executing a variety of applications such as mobile phone calls, e-mailing, viewing and editing texts, music reproduction, Internet communication, and computer games. The display surface of the display portion 9001 is bent, and an image can be displayed on the bent display surface. The portable information terminal 9200 can employ near field communication conformable to a communication standard. In that case, for example, mutual communication between the portable information terminal 9200 and a headset capable of wireless communication can be performed, and thus hands-free calling is possible. The portable information terminal 9200 includes the connection terminal 9006, and data can be directly transmitted to and received from another information terminal via a connector. Power charging through the connection terminal 9006 is also possible. Note that the charging operation may be performed by wireless power feeding without using the connection terminal 9006.

Unlike in the portable information terminal illustrated in FIG. 8A, the display surface of the display portion 9001 is not curved in the portable information terminal 9201 illustrated in FIG. 8B. Furthermore, the external state of the display portion of the portable information terminal 9201 is a non-rectangular shape (a circular shape in FIG. 8B).

Figure 8C:
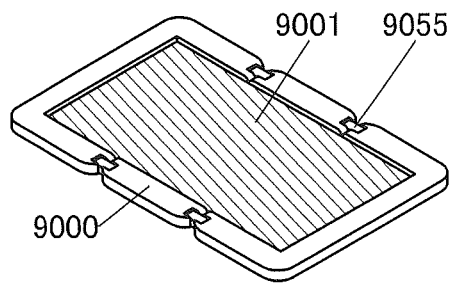
Figure 8D:
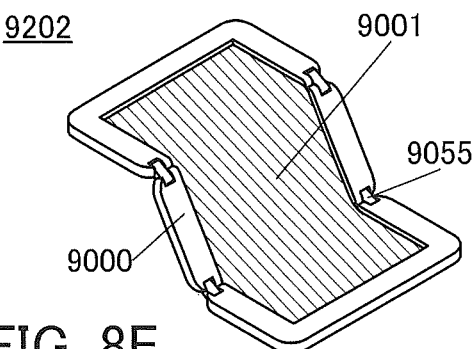
Figure 8E:
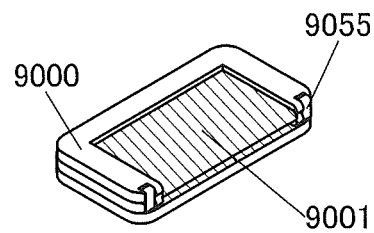

FIGS. 8C to 8E are perspective views of a foldable portable information terminal 9202. FIG. 8C is a perspective view illustrating the portable information terminal 9202 that is opened. FIG. 8D is a perspective view illustrating the portable information terminal 9202 that is being opened or being folded. FIG. 8E is a perspective view illustrating the portable information terminal 9202 that is folded.

The folded portable information terminal 9202 is highly portable, and the opened portable information terminal 9202 is highly browsable due to a seamless large display region. The display portion 9001 of the portable information terminal 9202 is supported by three housings 9000 joined together by hinges 9055. By folding the portable information terminal 9202 at a connection portion between two housings 9000 with the hinges 9055, the portable information terminal 9202 can be reversibly changed in shape from opened to folded. For example, the portable information terminal 9202 can be bent with a radius of curvature of greater than or equal to 1 mm and less than or equal to 150 mm.

This embodiment can be combined with any other embodiment as appropriate.

Embodiment 7

In this embodiment, examples in which the light-emitting element of one embodiment of the present invention is used for various lighting devices will be described with reference to FIGS. 9A to 9C and FIG. 10.

An electronic device or a lighting device that has a light-emitting region with a curved surface can be obtained with use of the light-emitting element of one embodiment of the present invention which is fabricated over a substrate having flexibility.

Furthermore, a light-emitting device in which the light-emitting element of one embodiment of the present invention is used can also be used for lighting for motor vehicles, examples of which are lighting for a windshield, a ceiling, and the like.

Figure 9A:
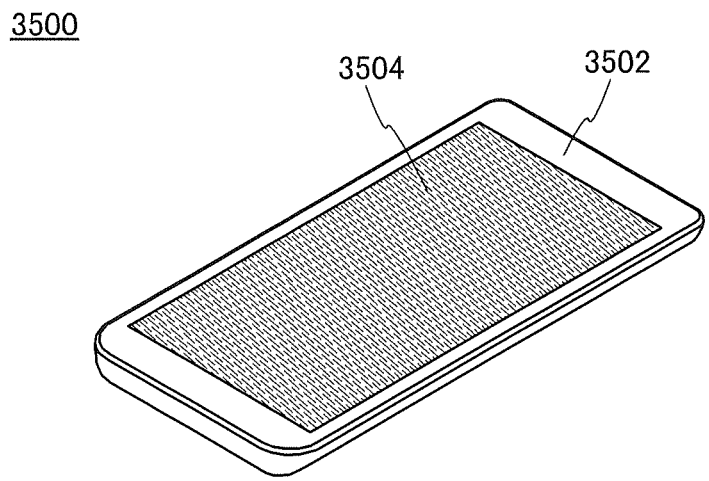
FIGS. 9A to 9C illustrate lighting devices of one embodiment of the present invention.
Figure 9B:
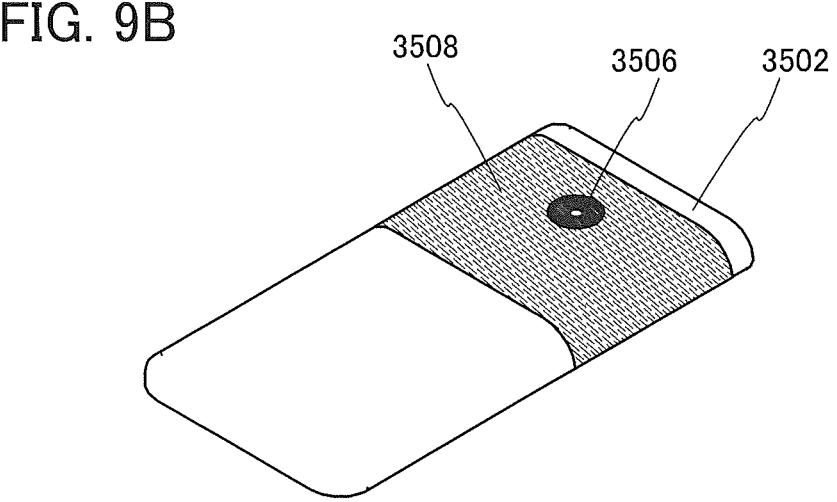

FIG. 9A is a perspective view illustrating one surface of a multifunction terminal 3500, and FIG. 9B is a perspective view illustrating the other surface of the multifunction terminal 3500. In a housing 3502 of the multifunction terminal 3500, a display portion 3504, a camera 3506, lighting 3508, and the like are incorporated. The light-emitting device of one embodiment of the present invention can be used for the lighting 3508.

The lighting 3508 that includes the light-emitting device of one embodiment of the present invention functions as a planar light source. Thus, unlike a point light source typified by an LED, the lighting 3508 can provide light emission with low directivity. When the lighting 3508 and the camera 3506 are used in combination, for example, imaging can be performed by the camera 3506 with the lighting 3508 lighting or flashing. Because the lighting 3508 functions as a planar light source, a photograph as if taken under natural light can be taken.

Note that the multifunction terminal 3500 illustrated in FIGS. 9A and 9B can have a variety of functions as in the electronic devices illustrated in FIGS. 7A to 7C.

The housing 3502 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared rays), a microphone, and the like. When a detection device including a sensor for detecting inclination, such as a gyroscope sensor or an acceleration sensor, is provided inside the multifunction terminal 3500, display on the screen of the display portion 3504 can be automatically switched by determining the orientation of the multifunction terminal 3500 (whether the multifunction terminal is placed horizontally or vertically for a landscape mode or a portrait mode).

The display portion 3504 may function as an image sensor. For example, an image of a palm print, a fingerprint, or the like is taken when the display portion 3504 is touched with the palm or the finger, whereby personal authentication can be performed. Furthermore, by providing a backlight or a sensing light source which emits near-infrared light in the display portion 3504, an image of a finger vein, a palm vein, or the like can be taken. Note that the light-emitting device of one embodiment of the present invention may be used for the display portion 3504.

Figure 9C:
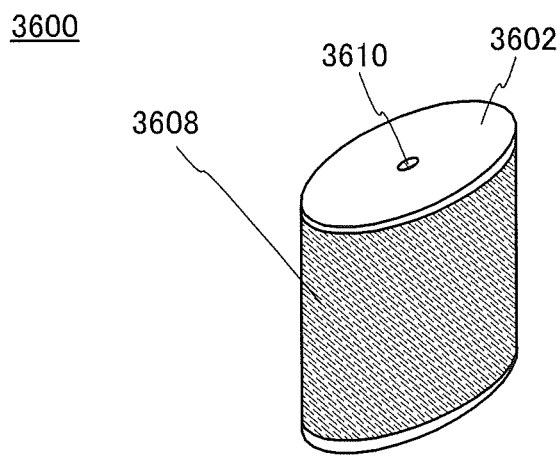

FIG. 9C is a perspective view of a security light 3600. The light 3600 includes lighting 3608 on the outside of the housing 3602, and a speaker 3610 and the like are incorporated in the housing 3602. The light-emitting element of one embodiment of the present invention can be used for the lighting 3608.

The light 3600 emits light when the lighting 3608 is gripped or held, for example. An electronic circuit that can control the manner of light emission from the light 3600 may be provided in the housing 3602. The electronic circuit may be a circuit that enables light emission once or intermittently a plurality of times or may be a circuit that can adjust the amount of emitted light by controlling the current value for light emission. A circuit with which a loud audible alarm is output from the speaker 3610 at the same time as light emission from the lighting 3608 may be incorporated.

The light 3600 can emit light in various directions; therefore, it is possible to intimidate a thug or the like with light, or light and sound. Moreover, the light 3600 may include a camera such as a digital still camera to have a photography function.

Figure 10:
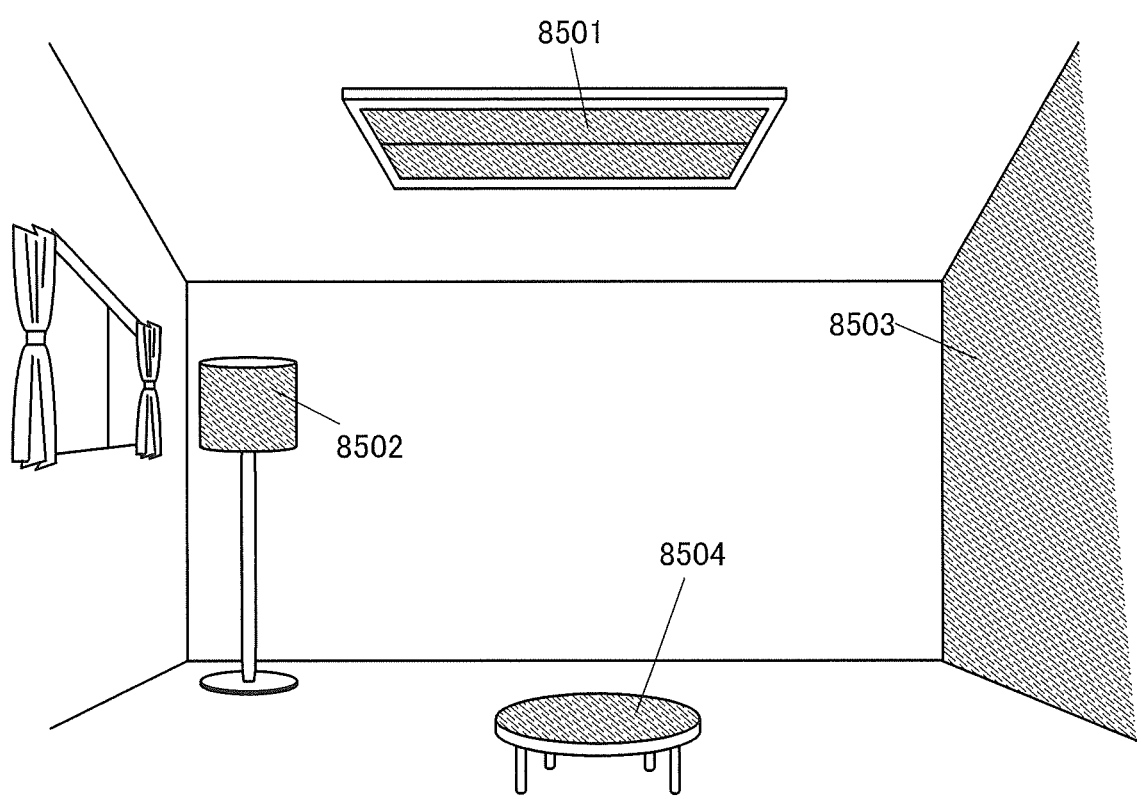
FIG. 10 illustrates lighting devices of one embodiment of the present invention.

FIG. 10 illustrates an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with use of a housing with a curved surface. A light-emitting element described in this embodiment is in the form of a thin film, which allows the housing to be designed more freely. Therefore, the lighting device can be elaborately designed in a variety of ways. Furthermore, a wall of the room may be provided with a large-sized lighting device 8503. Touch sensors may be provided in the lighting devices 8501, 8502, and 8503 to control the power on/off of the lighting devices.

Moreover, when the light-emitting element is used on the surface side of a table, a lighting device 8504 which has a function as a table can be obtained. When the light-emitting element is used as part of other furniture, a lighting device which has a function as the furniture can be obtained.

As described above, lighting devices and electronic devices can be obtained by application of the light-emitting device of one embodiment of the present invention. Note that the light-emitting device can be used for electronic devices in a variety of fields without being limited to the lighting devices and the electronic devices described in this embodiment.

The structure described in this embodiment can be combined with any of the structures described in the other embodiments and the example as appropriate.

Example 1

In this example, a method for synthesizing one of the compounds of one embodiment of the present invention and represented by General Formula (G0), 8-(9H-carbazol-9-yl)-4-(9'-phenyl-2,3'-bi-9H-carbazol-9-yl)benzofuro[3,2-d]pyrimidine (abbreviation: 8Cz-4PCCzBfpm-02) (Structural Formula (100)), and characteristics thereof are described.

Synthesis Example 1

Step 1: Synthesis of 8-chloro-4-(9'-phenyl-2,3'-bi-9H-carbazol-9-yl)benzofuro[3,2-d]pyrimidine Into a 200-mL three-neck flask the air in which was replaced with nitrogen, 0.30 g of sodium hydride (60%) was put, and 30 mL of N,N'-dimethylformamide (abbreviation: DMF) was dropped thereinto while stirring was performed. The three-neck flask was cooled to 0° C. with ice, a solution of 1.8 g of 9-phenyl-2,3'-bi-9H-carbazole and 15 mL of DMF was dropped to the mixture, the temperature of the mixture was raised to room temperature, and stirring was performed for one hour. After the stirring, a reaction container was cooled to 0° C. with ice, a solution of 0.82 g of 4,8-dichloro[1]benzofuro[3,2-d]pyrimidine and 20 mL of DMF was dropped to the mixture, the temperature of the mixture was raised to room temperature, and stirring was performed for 20 hours. The obtained reaction solution was added to ice water and subjected to extraction with toluene. The solution of the extract was washed with saturated saline. Then, magnesium sulfate was added and filtration was performed. The solvent of the obtained filtrate was distilled off. The obtained reaction mixture was purified by silica gel column chromatography.

Purification was performed by gradually increasing the proportion of toluene to hexane from 1:1 in a developing solvent. The obtained filtrate was concentrated, whereby 1.1 g of a target yellow solid of 8-chloro-4-(9'-phenyl-2,3'-bi-9H-carbazol-9-yl)benzofuro[3,2-d]pyrimidine was obtained with a yield of 45%. The synthesis scheme of Step 1 is shown in (A-1) below.

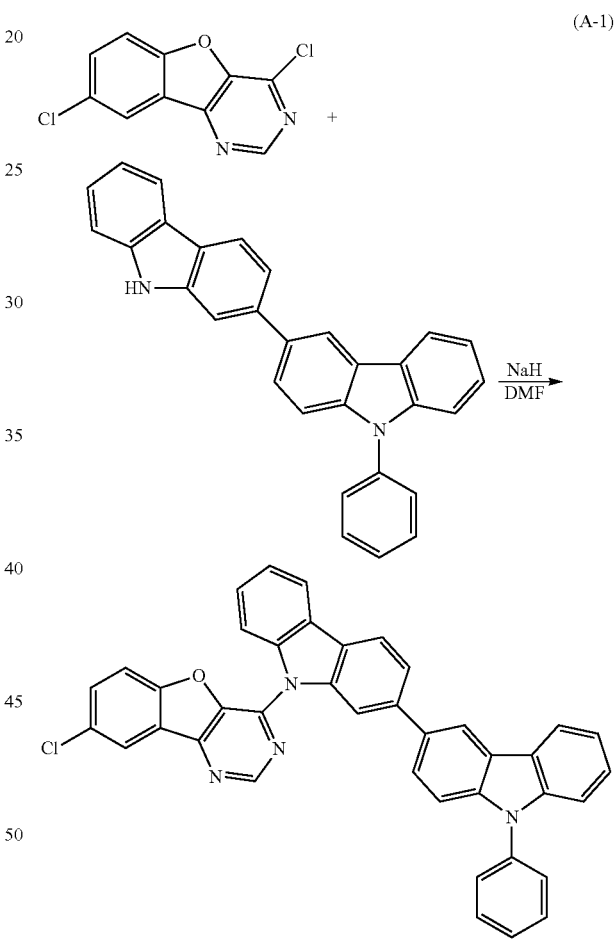

(A-1)

Step 2: Synthesis of 8-(9H-carbazol-9-yl)-4-(9'-phenyl-2,3'-bi-9H-carbazol-9-yl)benzofuro[3,2-d]pyrimidine (abbreviation: 8Cz-4PCCzBfpm-02)

Figure 11A:
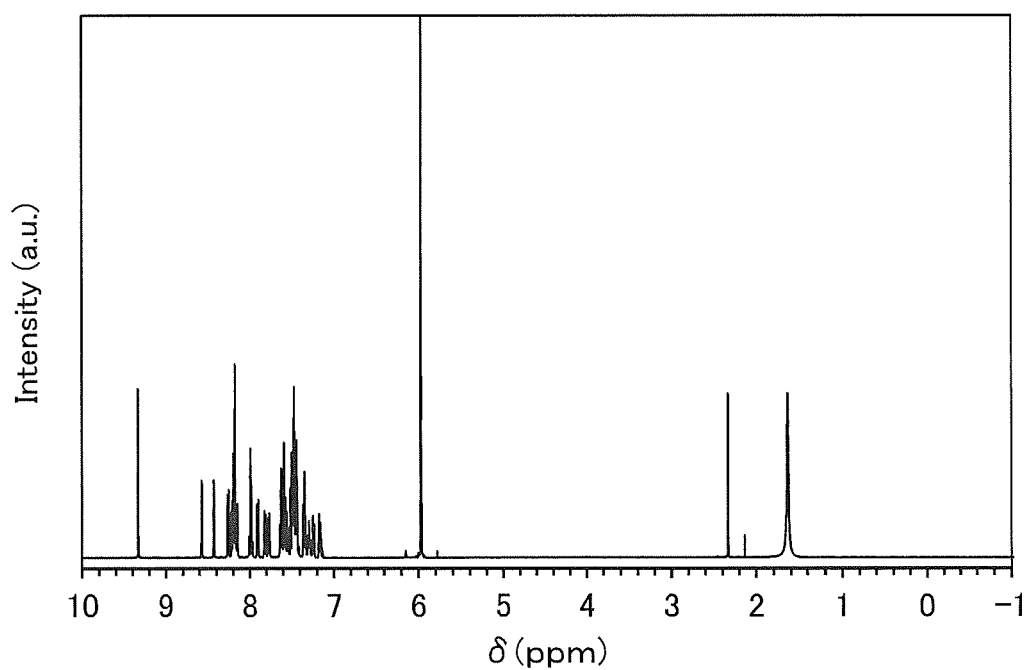
FIGS. 11A and 11B show NMR charts of a compound in Example.

Into a 200-mL three-neck flask, 1.6 g of 8-chloro-4-(9'-phenyl-2,3'-bi-9H-carbazol-9-yl)benzofuro[3,2-d]pyrimidine obtained in Step 1, 0.53 g of 9H-carbazole, 0.61 g of sodium tert-butoxide, and 50 mL of mesitylene were put, and the air in the flask was replaced with nitrogen. Then, 37 mg of di-tert-butyl(1-methyl-2,2-diphenylcyclopropyl)phosphine (abbreviation: cBRIDP) and 10 mg of allylpalladium(II)chloride dimer were added, and the mixture was heated under a nitrogen stream at 160° C. for 4 hours. The obtained reaction mixture was filtered, and washing with water and then washing with ethanol were performed. The obtained residue was purified by silica gel column chromatography. First, only toluene was in a developing solvent. Purification was performed by gradually increasing the proportion of ethyl acetate until the ratio of toluene to ethyl acetate became 10:1 in the developing solvent. The obtained filtrate was concentrated to obtain a solid and the solid was recrystallized with toluene and ethanol, whereby 0.98 g of a target yellow solid of 8Cz-4PCCzBfpm-02 was obtained with a yield of 50%. The synthesis scheme of this step is shown in (A-2) below.

in the range of 7.0 ppm to 9.6 ppm of FIG. 11A. The results revealed that 8Cz-4PCCzBfpm-02, which was the target substance, was obtained.

<Characteristics of 8Cz-4PCCzBfpm-02>

Next, 8Cz-4PCCzBfpm-02 obtained in this example was analyzed by liquid chromatography mass spectrometry (LC/MS).

In the analysis by LC/MS, liquid chromatography (LC) separation was carried out with UltiMate 3000 manufactured by Thermo Fisher Scientific K.K., and the MS analysis was carried out with Q Exactive manufactured by Thermo Fisher Scientific K.K.

In the LC separation, a given column was used at a column temperature of 40° C., and solution sending was

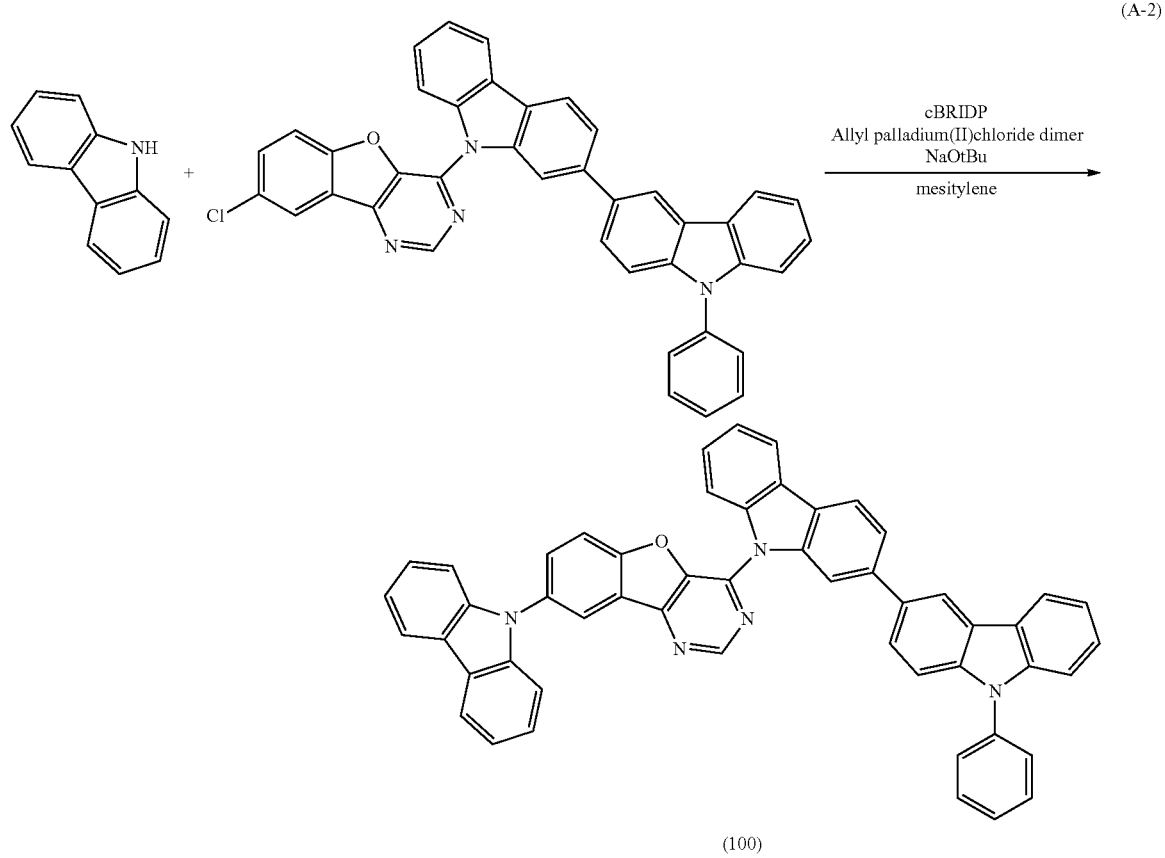

(A-2)

(100)

Then, 0.98 g of the yellow solid was purified by a train sublimation method. In the purification by sublimation, the yellow solid was heated at 330° C. under a pressure of 2.6 Pa with a flow rate of an argon gas of 5 mL/min. After the purification by sublimation, 0.68 g of a target brown solid was obtained at a collection rate of 69%.

The obtained solid was subjected to nuclear magnetic resonance spectrometry ($^1$H NMR), and the results are shown below.

$^1$H-NMR δ(CDCl$_3$): 7.27-7.31 (dt, 1H), 7.32-7.36 (t, 2H), 7.42-7.51 (m, 9H), 7.54-7.64 (m, 5H), 7.77 (d, 1H), 7.81 (d, 1H), 7.90 (d, 1H), 7.96-8.01 (m, 2H), 8.15-8.22 (m, 5H), 8.26 (d, 1H), 8.42 (1, 1H), 8.57 (s, 1H), 9.33 (s, 1H). Note that the peaks at around 2.33, 7.13-7.17, and 7.23-7.26 are derived from toluene.

Figure 11B:
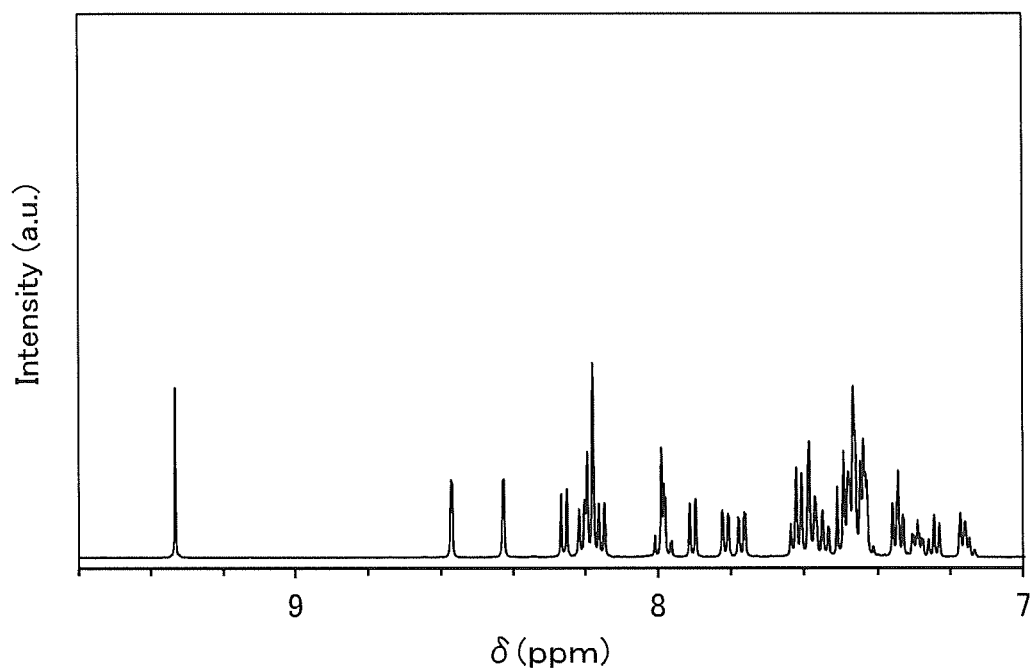

FIGS. 11A and 11B are $^1$H NMR charts of the obtained solid. Note that FIG. 11B is a chart showing an enlarged part performed in such a manner that an appropriate solvent was selected, the sample was prepared by dissolving 8Cz-4PCCzBfpm-02 in an organic solvent at an arbitrary concentration, and the injection amount was 5.0 μL.

In the MS analysis, a component with m/z of 741.25, which is an ion derived from 8Cz-4PCCzBfpm-02, was measured by a Targeted-MS$^2$ method. For Targeted-MS$^2$, the mass range was set to ±4.0 m/z and detection was performed in a positive mode. Energy for accelerating an ion (normalized collision energy: NCE) was set to 60 for the measurement. The obtained MS spectrum is shown in FIG. 12.

Figure 12:
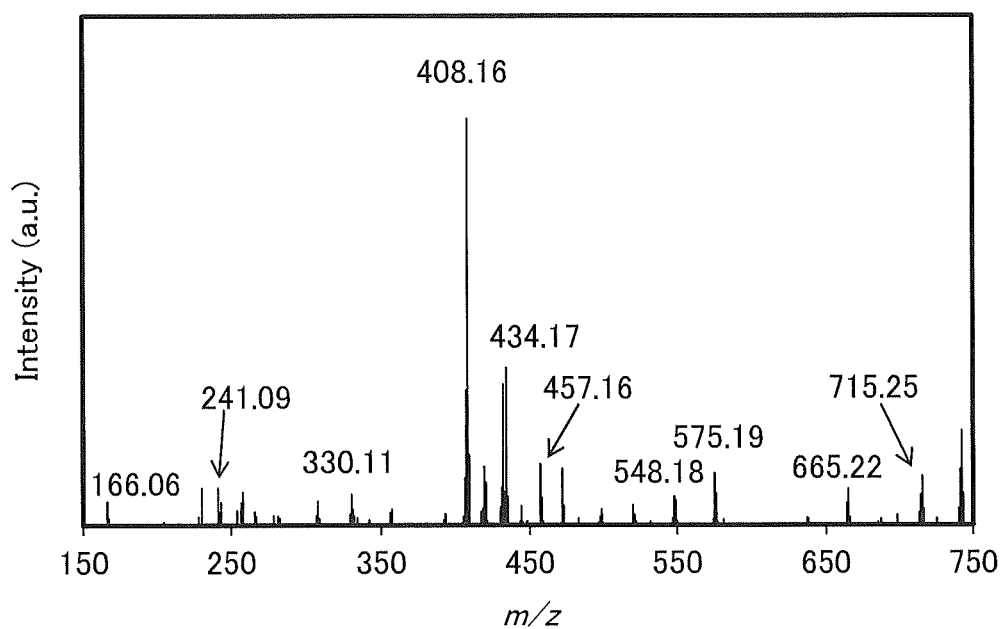
FIG. 12 shows an MS spectrum of a compound in Example.

FIG. 12 shows that product ions of 8Cz-4PCCzBfpm-02 are mainly detected around m/z=715, 665, 575, 548, 457, 434, 408, 330, 241, and 166. Note that the results in FIG. 12 show characteristics derived from 8Cz-4PCCzBfpm-02 and thus can be regarded as important data for identifying 8Cz-4PCCzBfpm-02 contained in a mixture.

The product ion around m/z=715 is presumed to be a cation generated due to dissociation of nitrile by cleavage of a pyrimidine skeleton in 8Cz-4PCCzBfpm-02. The product ion around m/z=548 is presumed to be a cation generated due to further dissociation of a carbazolyl group. The product ion around m/z=458 is presumed to be a cation generated due to dissociation of phenol by further cleavage of a benzofuran skeleton. The product ion around m/z=434 is presumed to be a cation generated due to further dissociation of an ethyl group. The product ion around m/z=408 is presumed to be a cation generated due to further dissociation of nitrile. These data suggest that 8Cz-4PCCzBfpm-02 includes a carbazolyl group and a benzofuropyrimidinyl group.

The product ion around m/z=665 is presumed to be a cation generated due to dissociation of phenyl in 8Cz-4PCCzBfpm-02. This data suggests that 8Cz-4PCCzBfpm-02 includes a phenyl group.

The product ion around m/z=575 is presumed to be a cation generated due to dissociation of carbazole in 8Cz-4PCCzBfpm-02. This data suggests that 8Cz-4PCCzBfpm-02 includes a carbazolyl group.

The product ion around m/z=241 is presumed to be a cation of a phenylcarbazole group. This data suggests that 8Cz-4PCCzBfpm-02 includes a phenylcarbazole group.

The product ion around m/z=166 is presumed to be a cation of a carbazolyl group. This data suggests that 8Cz-4PCCzBfpm-02 includes a carbazolyl group.

Figure 13:
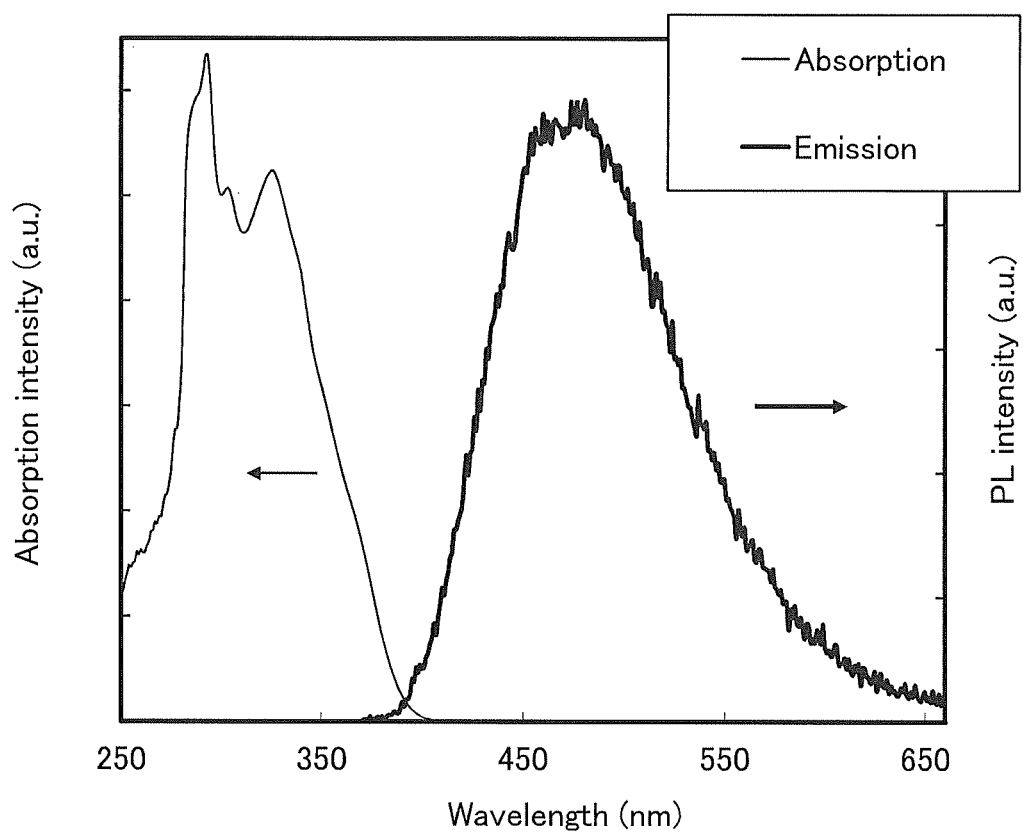
FIG. 13 shows absorption and emission spectra of a compound in Example.

Absorption and emission spectra of 8Cz-4PCCzBfpm-02 in a toluene solution are shown in FIG. 13.

The absorption spectrum was measured using a UV-visible spectrophotometer (V-550, manufactured by JASCO Corporation). A toluene solution of 8Cz-4PCCzBfpm-02 was put in a quartz cell and an absorption spectrum of 8Cz-4PCCzBfpm-02 in the toluene solution was measured. From this absorption spectrum, an absorption spectrum of the toluene solution measured with the quartz cell was subtracted, and the resultant value was shown in the drawing. The emission spectrum was measured using a PL-EL measurement apparatus (manufactured by Hamamatsu Photonics K.K.). The emission spectrum of 8Cz-4PCCzBfpm-02 in the toluene solution was measured with the toluene solution of 8Cz-4PCCzBfpm-02 put in a quartz cell.

It was found that the absorption peak wavelengths of 8Cz-4PCCzBfpm-02 in the toluene solution were around 292 nm, 302 nm, 305 nm, 327 nm, and 366 nm, and the emission peak wavelengths thereof were around 462 nm and 481 nm (an excitation wavelength of 354 nm).

Example 2

In this example, a method for synthesizing one of the compounds that are one embodiment of the present invention and represented by General Formula (G0), 4,8-bis(9'-phenyl-2,3'-bi-9H-carbazol-9-yl)benzofuro[3,2-d]pyrimidine (abbreviation: 4,8PCCz2Bfpm-02) (Structural Formula (102)), and characteristics of thereof are described.

Synthesis Example 2

Synthesis of 4,8-bis(9'-phenyl-2,3'-bi-9H-carbazol-9-yl)benzofuro[3,2-d]pyrimidine (abbreviation: 4,8PCCz2Bfpm-02)

Into a 200-mL three-neck flask with a reflux pipe, 1.0 g of 4,8-dichloro[1]benzofuro[3,2-d]pyrimidine, 3.8 g of 9'-phenyl-2,3'-bi-9H-carbazole, 1.8 g of sodium tert-butoxide, and 130 ml of mesitylene were put, and the air in the flask was replaced with nitrogen. Then, 120 mg of cBRIDP (abbreviation) and 31 mg of allylpalladium(II)chloride dimer were added, and the mixture was stirred at 140° C. for 7 hours. The solvent was distilled off from the obtained reaction mixture, the concentrated obtained reaction mixture was dissolved in toluene, and the solution was filtered through celite, alumina, and then celite. The obtained filtrate was concentrated, whereby 1.8 g of a target yellow solid of 4,8PCCz2Bfpm-02 was obtained with a yield of 41%. The synthesis scheme of this step is shown in (B-1) below.

(B-1)

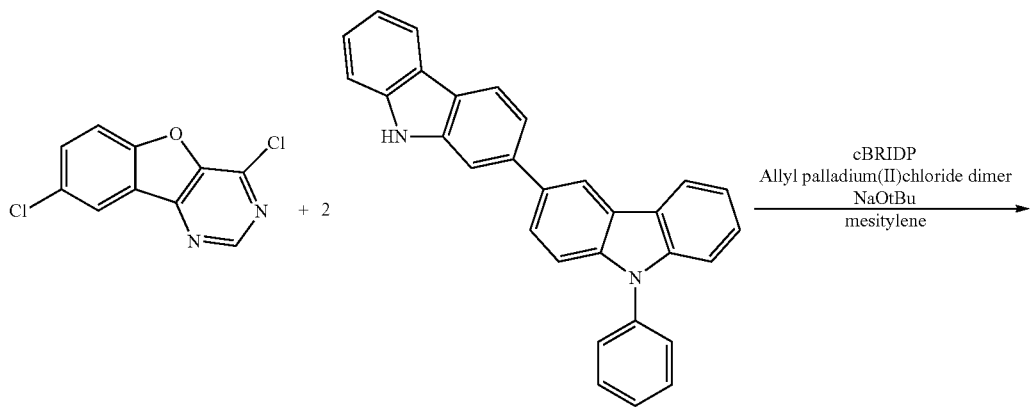

-continued

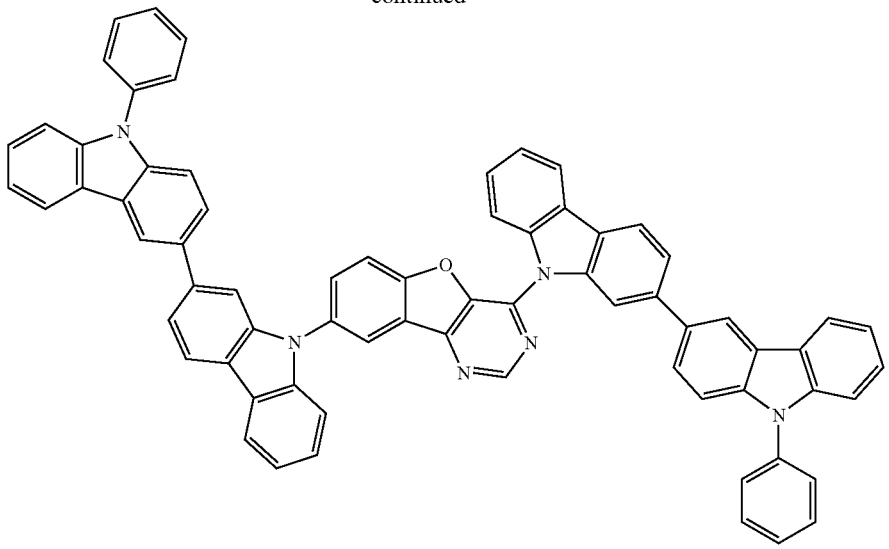

Then, 1.8 g of the yellow solid was purified by a train sublimation method. In the purification by sublimation, the yellow solid was heated at 390° C. under a pressure of 8.2×10$^{-3}$ Pa. After the purification by sublimation, 0.67 g of a target brown solid was obtained at a collection rate of 37%.

The obtained solid was subjected to nuclear magnetic resonance spectrometry ($^1$H NMR), and the results are shown below.

$^1$H-NMR δ(TCE-d$_2$): 7.22-7.26 (m, 2H), 7.36-7.61 (m, 21H), 7.68-7.73 (m, 3H), 7.77 (d, 1H), 7.81 (d, 1H), 7.88 (d, 1H), 8.01-8.05 (t, 2H), 8.11 (d, 1H), 8.14 (d, 1H), 8.20-8.29 (m, 5H), 8.35 (s, 1H), 8.42 (s, 1H), 8.65 (s, 1H), 9.33 (s, 1H).

Figure 14A:
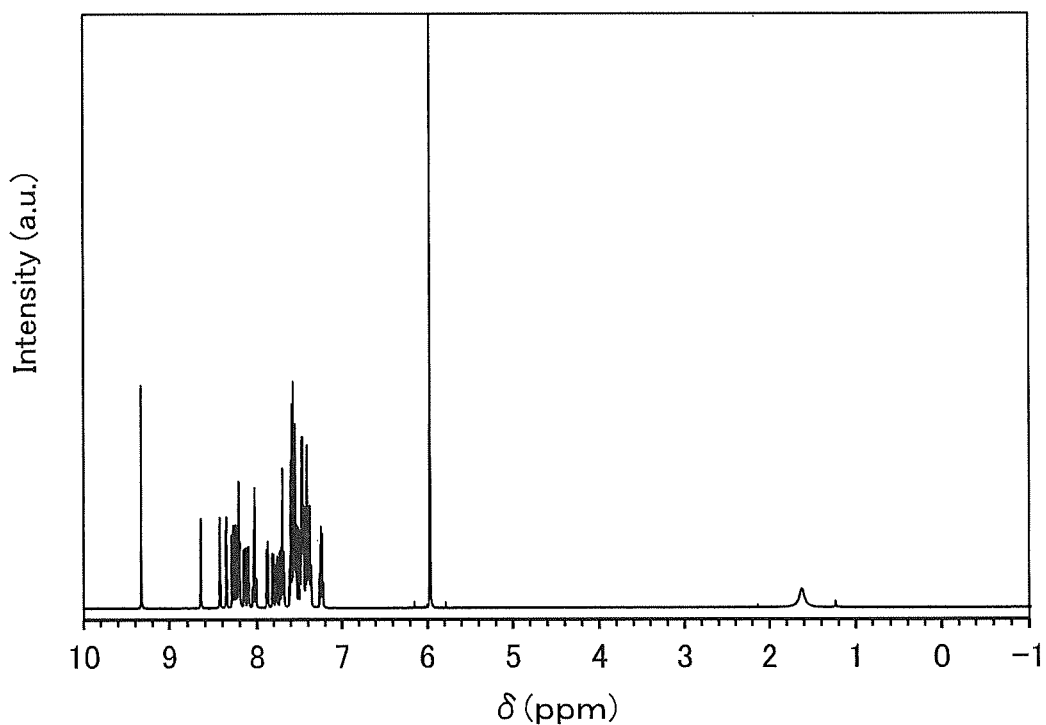
FIGS. 14A and 14B show NMR charts of a compound in Example.
Figure 14B:
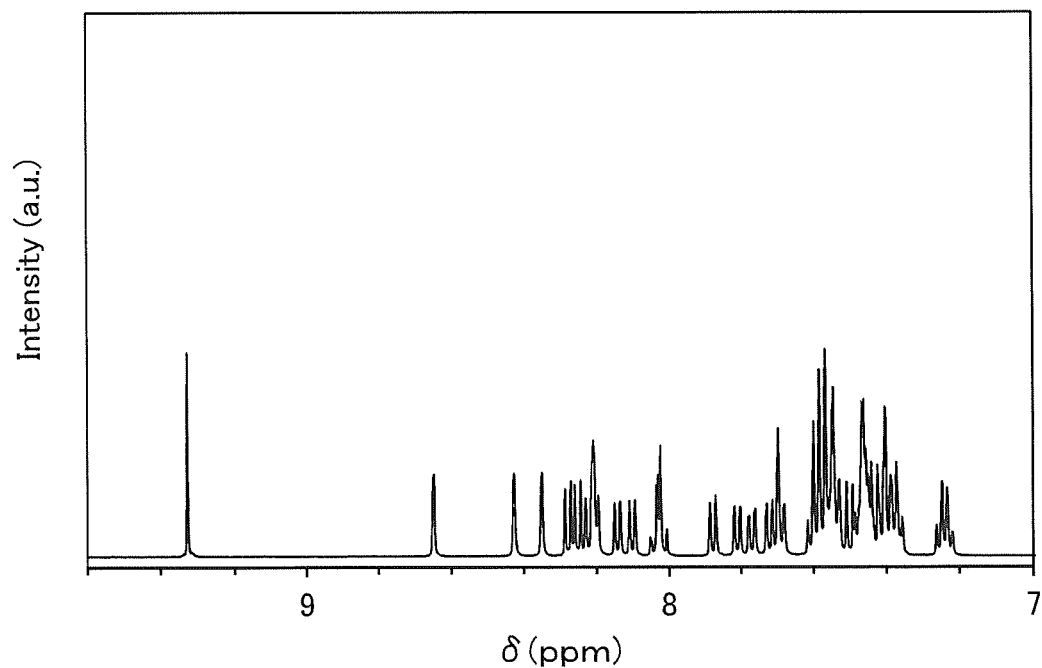

FIGS. 14A and 14B are $^1$H NMR charts of the obtained solid. Note that FIG. 14B is a chart showing an enlarged part in the range of 7.0 ppm to 9.6 ppm of FIG. 14A. The results revealed that 4,8PCCz2Bfpm-02, which was the target substance, was obtained.

<Characteristics of 4,8PCCz2Bfpm-02>

Figure 15:
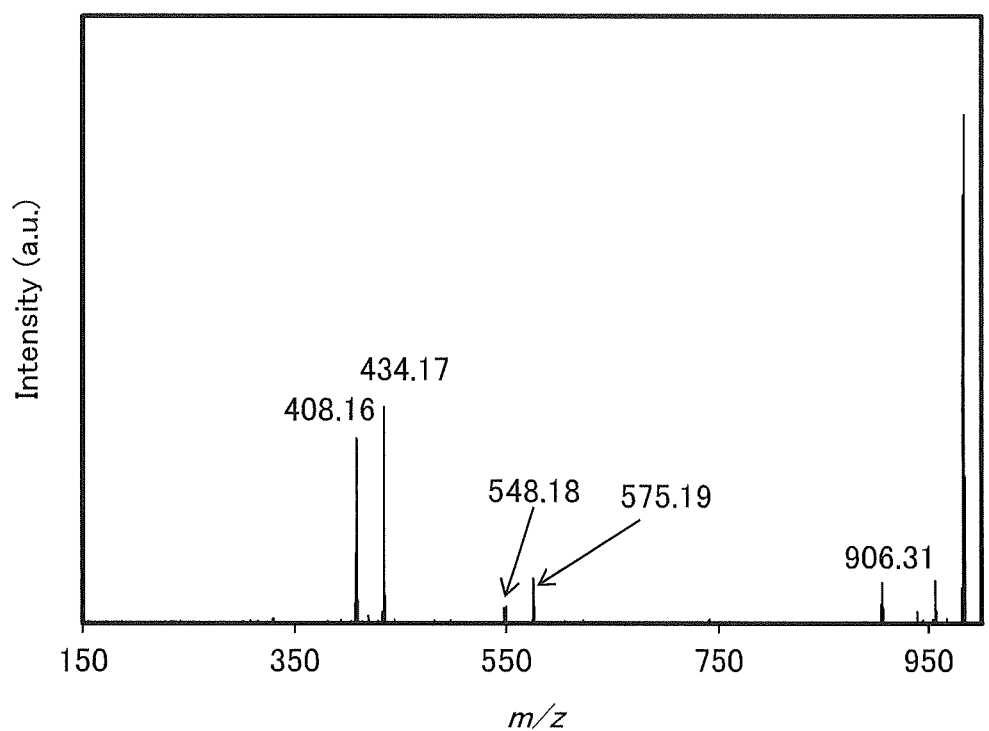
FIG. 15 shows an MS spectrum of a compound in Example.

Next, 4,8PCCz2Bfpm-02 obtained in this example was analyzed by LC/MS. The results are shown in FIG. 15. The analysis method was the same as that in the above example. In the MS analysis, a component with m/z of 987.34 was measured by a Targeted-MS$^2$ method.

FIG. 15 shows that product ions of 4,8PCCz2Bfpm-02 are mainly detected around m/z=906, 575, 548, 434, and 408. Note that the results in FIG. 15 show characteristics derived from 4,8PCCz2Bfpm-02 and thus can be regarded as important data for identifying 4,8PCCz2Bfpm-02 contained in a mixture.

The product ion around m/z=905 is presumed to be a cation generated due to dissociation of a phenyl group in 4,8PCCz2Bfpm-02. The product ion around m/z=575 is presumed to be a cation generated due to further dissociation of a bicarbazolyl group. These data suggest that 4,8PCCz2Bfpm-02 includes a phenylbicarbazolyl group.

The product ion around m/z=434 is presumed to be a cation generated by dissociation of a benzofuranyl group and a cyano group due to further cleavage of a benzofuropyrimidine skeleton from the product ion around m/z=575. This data suggests that 4,8PCCz2Bfpm-02 has a benzofuropyrimidine skeleton.

The product ion around m/z=408 is presumed to be a cation of a phenylbicarbazolyl group. This data suggests that 4,8PCCz2Bfpm-02 includes a phenylbicarbazolyl group.

Figure 16:
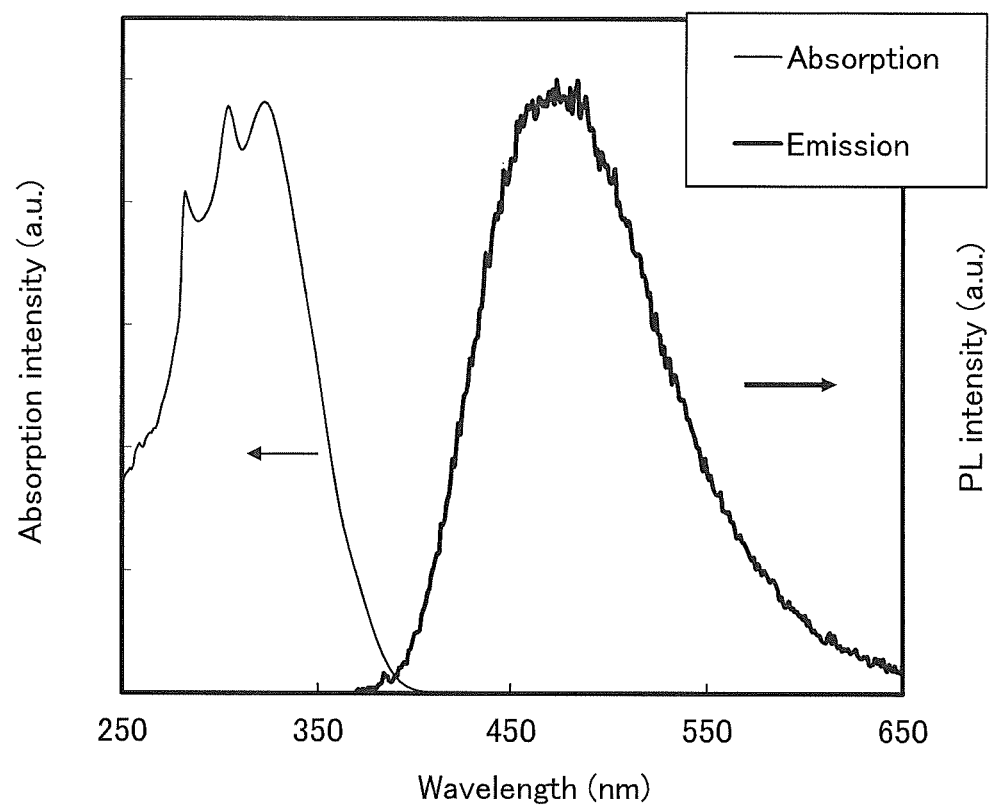
FIG. 16 shows absorption and emission spectra of a compound in Example.

Absorption and emission spectra of 4,8PCCz2Bfpm-02 in a toluene solution are shown in FIG. 16. The measurement was performed in a manner similar to that described in the above example.

As shown in FIG. 16, the absorption peak wavelengths of 4,8PCCz2Bfpm-02 in the toluene solution were around 282 nm, 302 nm, and 321 nm, and the emission peak wavelength thereof was around 473 nm (an excitation wavelength of 344 nm).

Example 3

In this example, fabrication examples of light-emitting elements each including the organic compound of one embodiment of the present invention and characteristics of the light-emitting elements are described. A comparative light-emitting element 2 was also fabricated. A cross-sectional view of the structure of each of the elements fabricated in this example is similar to that in FIG. 1A. Table 1 shows details of the element structure. In addition, structures and abbreviations of compounds used here are given below. Note that the above example can be referred to for other organic compounds.

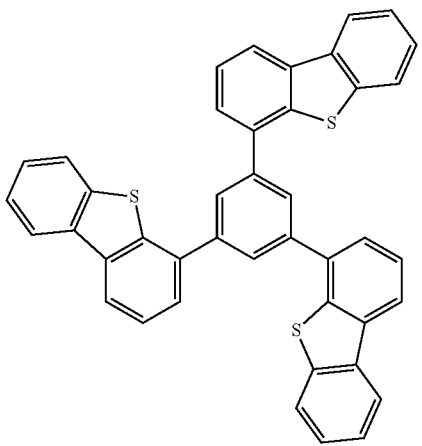

(DBT3P-II)

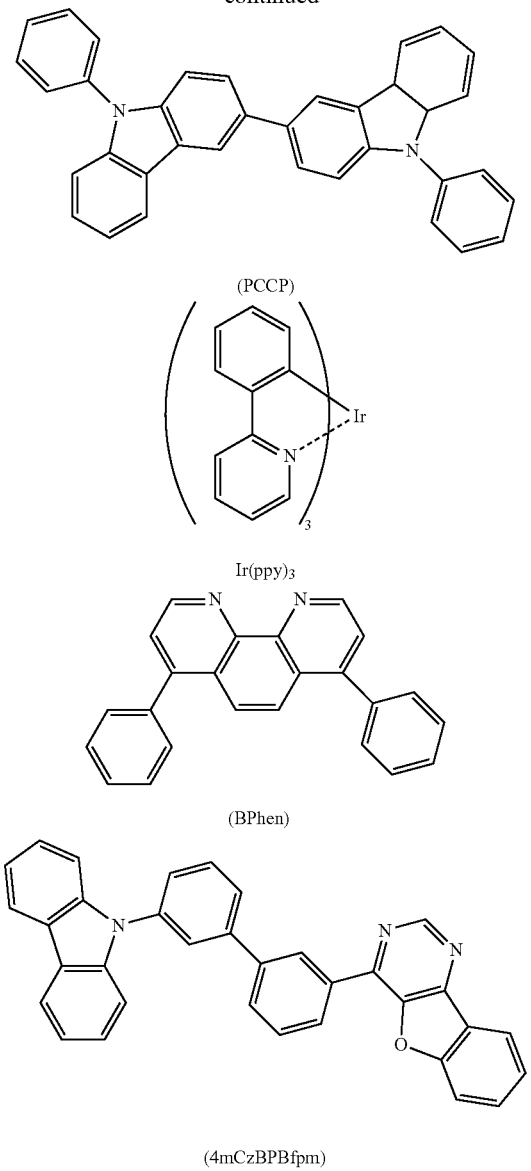

<<Fabrication of Light-Emitting Element 1>>

As the electrode 101, an ITSO film was formed to a thickness of 70 nm over the substrate 200. The electrode area of the electrode 101 was set to 4 mm² (2 mm×2 mm).

As the hole-injection layer 111, 4,4′,4″-(benzene-1,3,5-triyl)tri(dibenzothiophene) (abbreviation: DBT3P-II) and molybdenum oxide (MoO$_3$) were deposited over the electrode 101 by co-evaporation in a weight ratio of DBT3P-II:MoO$_3$=1:0.5 to a thickness of 50 nm.

As the hole-transport layer 112, 3,3′-bis(9-phenyl-9H-carbazole) (abbreviation: PCCP) was deposited over the hole-injection layer 111 by evaporation to a thickness of 20 nm.

Then, as the light-emitting layer 130, 8Cz-4PCCzBfpm-02 and tris(2-phenylpyridinato-N,C$^{2'}$)iridium(III) (abbreviation: Ir(ppy)$_3$) were deposited over the hole-transport layer 112 by co-evaporation such that the deposited layer had a weight ratio of 8Cz-4PCCzBfpm-02:Ir(ppy)$_3$=0.9:0.1 and a thickness of 40 nm. Note that in the light-emitting layer 130, Ir(ppy)$_3$ corresponds to the guest material that emits phosphorescence.

As the electron-transport layer 118, 8Cz-4PCCzBfpm-02 and bathophenanthroline (abbreviation: BPhen) were sequentially deposited by evaporation to thicknesses of 15 nm and 10 nm, respectively, over the light-emitting layer 130. Then, as the electron-injection layer 119, LiF was deposited over the electron-transport layer 118 by evaporation to a thickness of 1 nm.

As the electrode 102, aluminum (Al) was deposited over the electron-injection layer 119 to a thickness of 200 nm.

Next, in a glove box containing a nitrogen atmosphere, a light-emitting element 1 was sealed by fixing the substrate 220 to the substrate 200 over which the organic material was deposited using a sealant for an organic EL device. Specifically, after the sealant was applied to surround the organic material over the substrate 200 and the substrate 200 was bonded to the substrate 220, irradiation with ultraviolet light having a wavelength of 365 nm at 6 J/cm² and heat treatment at 80° C. for one hour were performed. Through the process, the light-emitting element 1 was obtained.

<<Fabrication of Comparative Light-Emitting Element 2>>

The comparative light-emitting element 2 was fabricated through the same steps as those for the light-emitting element 1 except for the steps of forming the light-emitting layer 130 and the electron-transport layer 118.

TABLE 1

| | Layer | Reference numeral | Thickness (nm) | Material | Weight ratio |
|---|---|---|---|---|---|
| Light-emitting element 1 | Electrode | 102 | 200 | Al | — |
| | Electron-injection layer | 119 | 1 | LiF | — |
| | Electron-transport layer | 118(2) | 10 | BPhen | — |
| | | 118(1) | 15 | 8Cz-4PCCzBfPm-02 | — |
| | Light-emitting layer | 130 | 40 | 8Cz-4PCCzBfPm-02:Ir(ppy)$_3$ | 0.9:0.1 |
| | Hole-transport layer | 112 | 20 | PCCP | — |
| | Hole-injection layer | 111 | 50 | DBT3P-II:MoO$_3$ | 1:0.5 |
| | Electrode | 101 | 70 | ITSO | — |
| Comparative Light-emitting element 2 | Electrode | 102 | 200 | Al | — |
| | Electron-injection layer | 119 | 1 | LiF | — |
| | Electron-transport layer | 118(2) | 10 | BPhen | — |
| | | 118(1) | 15 | 4mCzBPBfpm | — |
| | Light-emitting layer | 130 | 40 | 4mCzBPBfpm:Ir(ppy)$_3$ | 0.9:0.1 |
| | Hole-transport layer | 112 | 20 | PCCP | — |
| | Hole-injection layer | 111 | 50 | DBT3P-II:MoO$_3$ | 1:0.5 |
| | Electrode | 101 | 70 | ITSO | — |

As the light-emitting layer 130 of the comparative light-emitting element, 4-{3-[3'-(9H-carbazol-9-yl)]biphenyl-3-yl}benzofuro[3,2-d]pyrimidine (abbreviation: 4mCzBPBfpm) and Ir(ppy)$_3$ were deposited over the hole-transport layer 112 by co-evaporation such that the deposited layer had a weight ratio of 4mCzBPBfpm:Ir(ppy)$_3$=0.9:0.1 and a thickness of 40 nm. Note that in the light-emitting layer 130, Ir(ppy)$_3$ corresponds to the guest material that emits phosphorescence.

As the electron-transport layer 118, 4mCzBPBfpm and bathophenanthroline (abbreviation: BPhen) were sequentially deposited by evaporation to thicknesses of 15 nm and 10 nm, respectively, over the light-emitting layer 130.

<Characteristics of Light-Emitting Elements>

Figure 17:
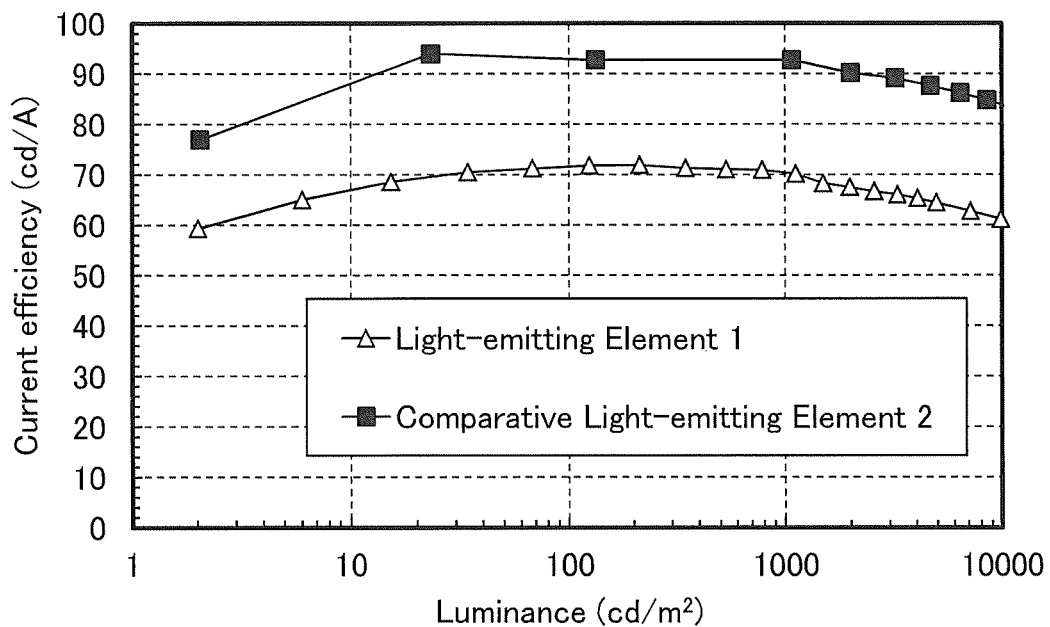
FIG. 17 shows current efficiency-luminance characteristics of light-emitting elements in Example.
Figure 18:
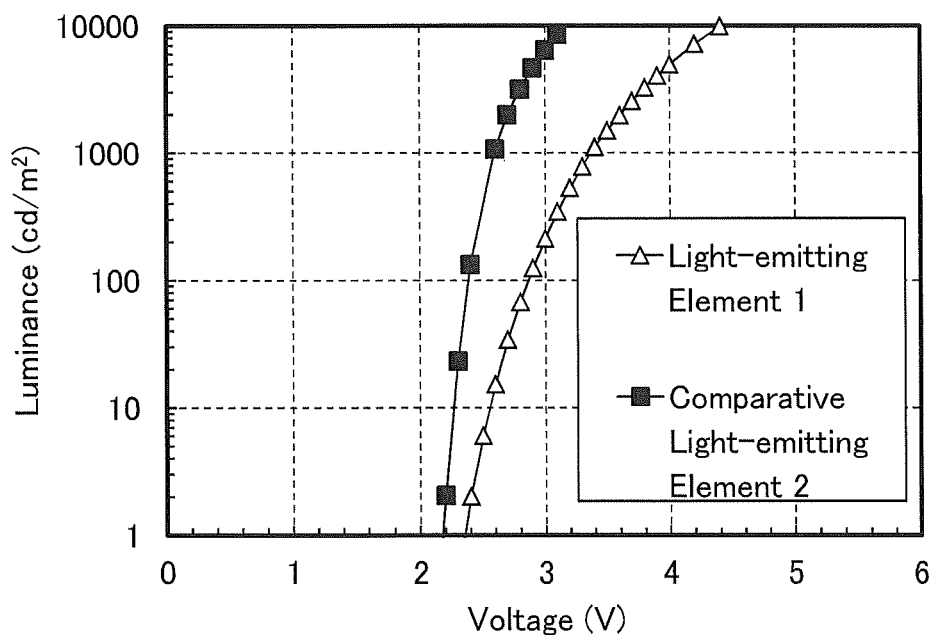
FIG. 18 shows luminance-voltage characteristics of light-emitting elements in Example.
Figure 19:
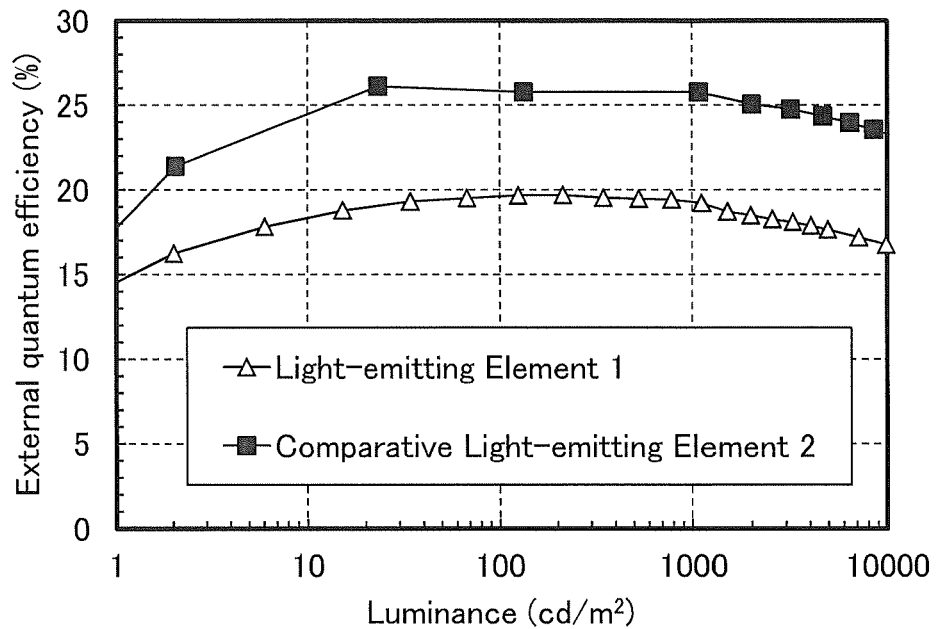
FIG. 19 shows external quantum efficiency-luminance characteristics of light-emitting elements in Example.
Figure 20:
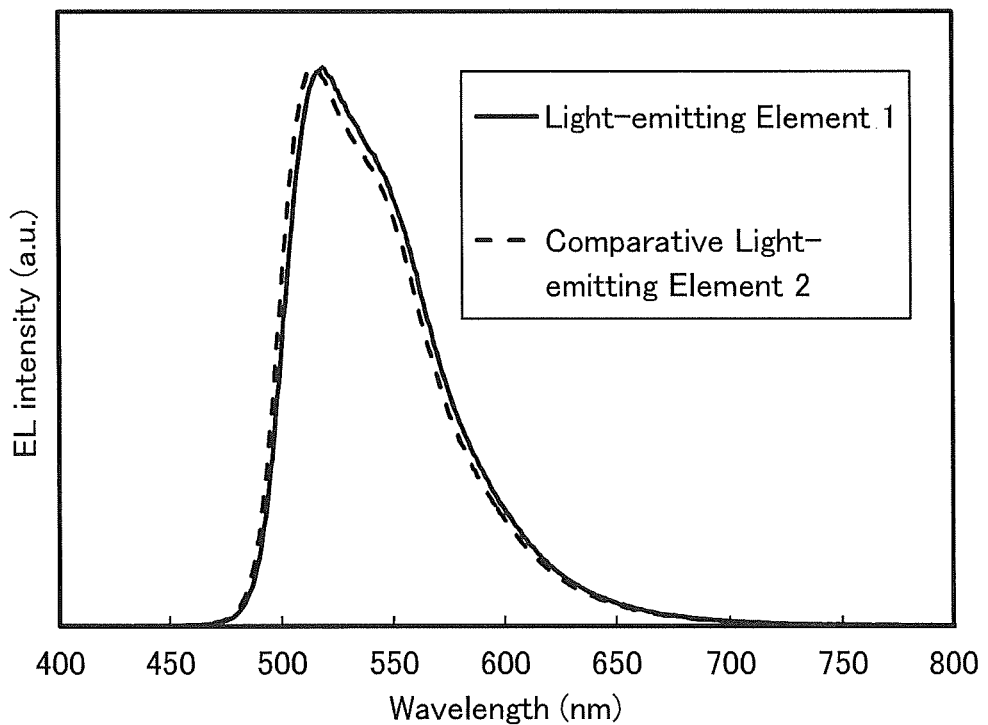
FIG. 20 shows emission spectra of light-emitting elements in Example.

The current efficiency-luminance characteristics of the fabricated light-emitting element 1 and the fabricated comparative light-emitting element 2 are shown in FIG. 17. The luminance-voltage characteristics thereof are shown in FIG. 18. The external quantum efficiency-luminance characteristics thereof are shown in FIG. 19. The measurements of the light-emitting elements were performed at room temperature (in an atmosphere kept at 23° C.). FIG. 20 shows the electroluminescence spectra obtained when a current at a current density of 2.5 mA/cm$^2$ was supplied to the light-emitting element 1 and the comparative light-emitting element 2. The measurements were performed at room temperature.

Table 2 shows the element characteristics of the light-emitting element 1 and the comparative light-emitting element 2 at around 1000 cd/m$^2$.

TABLE 2

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 1 | 3.4 | 1.59 | (0.31, 0.64) | 1117 | 70 | 64 | 19 |
| Comparative light-emitting element 2 | 2.6 | 1.16 | (0.31, 0.64) | 1075 | 93 | 112 | 26 |

As shown in FIG. 17 to FIG. 19 and Table 2, the light-emitting element 1 and the comparative light-emitting element 2 exhibited high current efficiency and high external quantum efficiency. In addition, a fall (roll-off) in the current efficiency and the external quantum efficiency of the light-emitting element 1 and the comparative light-emitting element 2 was small even on the high luminance side, which is excellent.

As shown in FIG. 20, the light-emitting element 1 and the comparative light-emitting element 2 emitted green light having electroluminescence spectra with peaks at wavelengths of 519 nm and 513 nm, respectively, and full widths at half maximum of 69 nm. The obtained electroluminescence spectrum reveals that light is emitted from Ir(ppy)$_3$ as the guest material.

<Reliability of Light-Emitting Elements>

Figure 21:
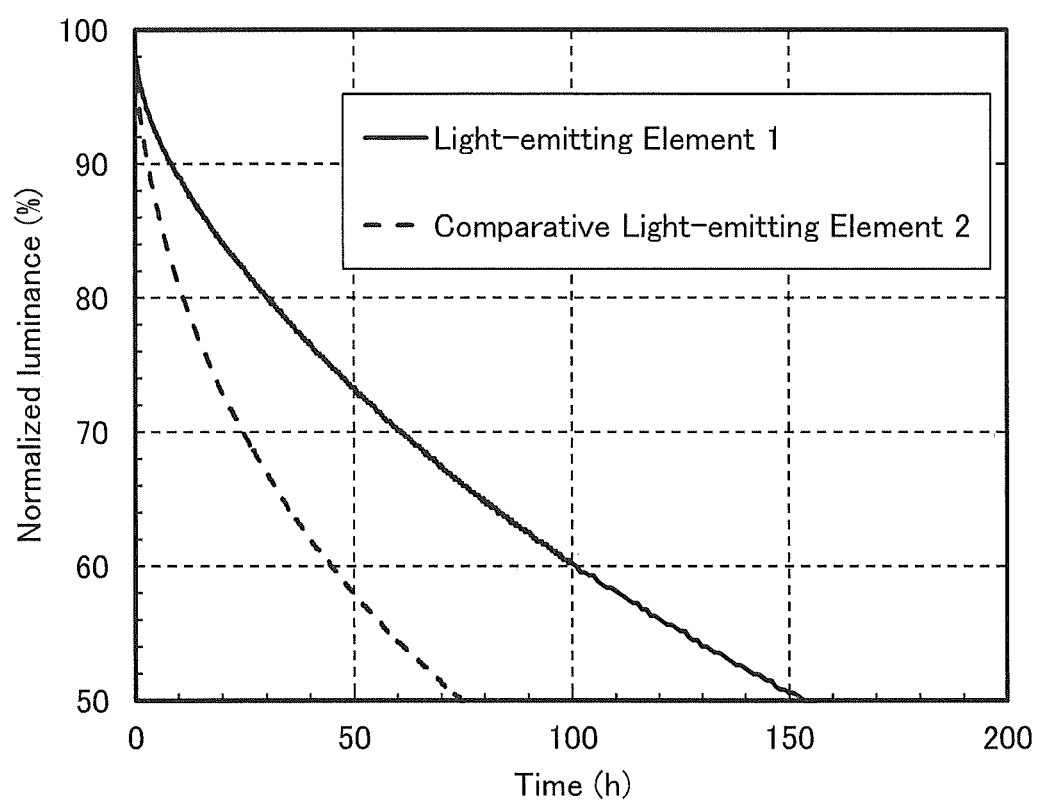
FIG. 21 shows reliability test results of light-emitting elements in Example.

Next, driving tests at a constant current of 2 mA were performed on the light-emitting element 1 and the comparative light-emitting element 2. The results are shown in FIG. 21. As shown in FIG. 21, the luminance half-life of the light-emitting element 1 was approximately twice as long as that of the comparative light-emitting element 2. It is because 8Cz-4PCCzBfpm-02 of one embodiment of the present invention has high electrochemical stability by having a carbazole skeleton, which is one of condensed rings, in the 6-, 7-, 8-, or 9-position of a benzofuro[3,2-d]pyrimidine skeleton.

Example 4

In this example, a method for synthesizing one of the compounds that are one embodiment of the present invention and represented by General Formula (G0), 8-(9H-carbazol-9-yl)-4-[3-(9'-phenyl-2,3'-bi-9H-carbazol-9-yl)phenyl]benzofuro[3,2-d]pyrimidine (abbreviation: 8Cz-4mPCCzPBfpm) (Structural Formula (104)), and characteristics thereof are described.

Synthesis Example 3

Step 1: Synthesis of 9-(3-bromophenyl)-9'-phenyl-2,3'-bi-9H-carbazole

Into a 500-mL three-neck flask, 16 g of 9-phenyl-2,3'-bi-9H-carbazole, 14 g of 3-bromoiodobenzene, and 12 g of tripotassium phosphate were put, and the air in the flask was replaced with nitrogen. Then, 190 mL of 1,4-dioxane, 0.65 g of trans-1,2-diaminocyclohexane, and 0.54 g of copper(I) iodide were added thereto, and the mixture was heated under a nitrogen stream at 120° C. for 8 hours. Furthermore, 3.0 g of tripotassium phosphate, 0.16 g of trans-1,2-diaminocyclohexane, and 0.13 g of copper(I) iodide were added, and the mixture was heated under a nitrogen stream at 120° C. for 14 hours. Water and ethanol were added to the obtained reaction mixture and filtration was performed. The filtrate was extracted with toluene, the solution of the extract was washed with saturated saline, magnesium sulfate was added, and then filtration was performed. The solvent of the filtrate was distilled off and the residue was dissolved in hot toluene. Purification was performed by silica gel column chromatography using a mixed solvent of a 1:2 ratio of toluene to hexane as a developing solvent, whereby 16 g of a target pale yellow solid was obtained in a yield of 72%. The synthesis scheme of Step 1 is shown in (C-1) below.

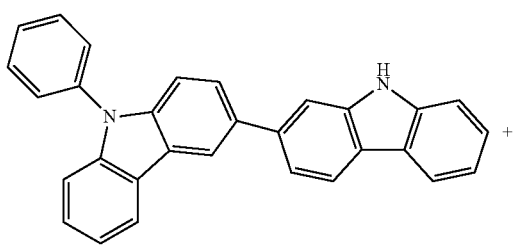

(C-1)

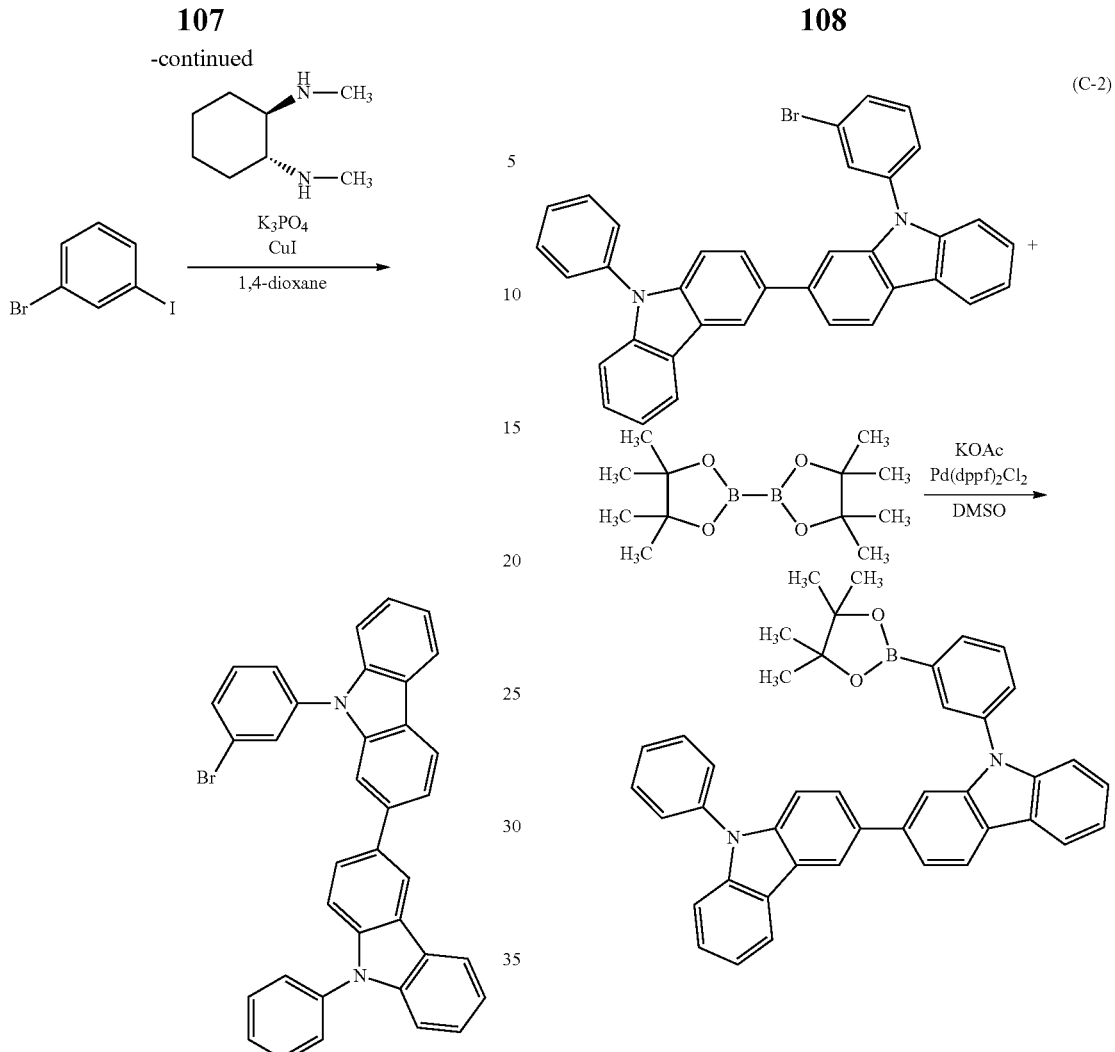

Step 3: Synthesis of 8-chloro-4-[3-(9'-phenyl-2,3'-bi-9H-carbazol-9-yl)phenyl]benzofuro[3,2-d]pyrimidine Step 2: Synthesis of 9-[3-(4,4,5,5-tetramethyl-1,3,2-dioxaborolan-2-yl)phenyl]-9'-phenyl-2,3'-bi-9H-carbazole Into a 500-mL three-neck flask, 16 g of 9-(3-bromophenyl)-9'-phenyl-2,3'-bi-9H-carbazole obtained in Step 1, 9.1 g of bis(pinacolato)diboron, and 9.1 g of potassium acetate were put, and the air in the flask was replaced with nitrogen. Then, 150 mL of dimethyl sulfoxide (abbreviation: DMSO) and 1.1 g of [1,1'-bis(diphenylphosphino)ferrocene]dichloropalladium(II) (abbreviation: Pd(dppf)$_2$Cl$_2$) were added thereto, and the mixture was stirred at 110° C. for 13 hours. Water was added to the obtained reaction mixture and the mixture was filtered. The filtrate was extracted with toluene, the solution of the extract was washed with saturated saline, magnesium sulfate was added, and then filtration was performed. The solvent of the obtained filtrate was distilled off, and the residue was purified by neutral silica gel column chromatography. Purification was performed by gradually increasing the proportion of toluene to hexane from 1:10 in a developing solvent. The solvent of the obtained fraction was distilled off and the obtained solid was recrystallized with a mixed solvent of toluene and hexane, whereby 9.7 g of a target pale yellow solid was obtained in a yield of 58%. The synthesis scheme of Step 2 is shown in (C-2) below.

Into a 100-mL three-neck flask, 1.1 g of 4,8-dichloro[1]benzofuro[3,2-d]pyrimidine, 3.7 g of 9-[3-(4,4,5,5-tetramethyl-1,3,2-dioxaborolan-2-yl)phenyl]-9'-phenyl-2,3'-bi-9H-carbazole obtained in Step 2, 1.7 g of a 2M cesium fluoride solution, 50 mL of toluene, and 5 mL of ethanol were put, and the air in the flask was replaced with nitrogen. Then, 21 mg of palladium(II) acetate and 67 mg of di(1-adamantyl)-n-butylphosphine were added, and the mixture was heated at 90° C. for 21 hours. Water and ethanol were added to the obtained reaction mixture, the mixture was filtered, and the residue was washed with ethanol. The residue was purified by neutral silica gel column chromatography. First, only toluene was in a developing solvent. Purification was performed by gradually increasing the proportion of ethyl acetate until the ratio of toluene to ethyl acetate became 1:10 in the developing solvent. The obtained fraction was dried, whereby 1.9 g of a target pale yellow solid was obtained in a yield of 59%. Synthesis was performed again by a method similar to that described above, whereby 1 g of a target pale yellow solid was additionally synthesized. The synthesis scheme of Step 3 is shown in (C-3) below.

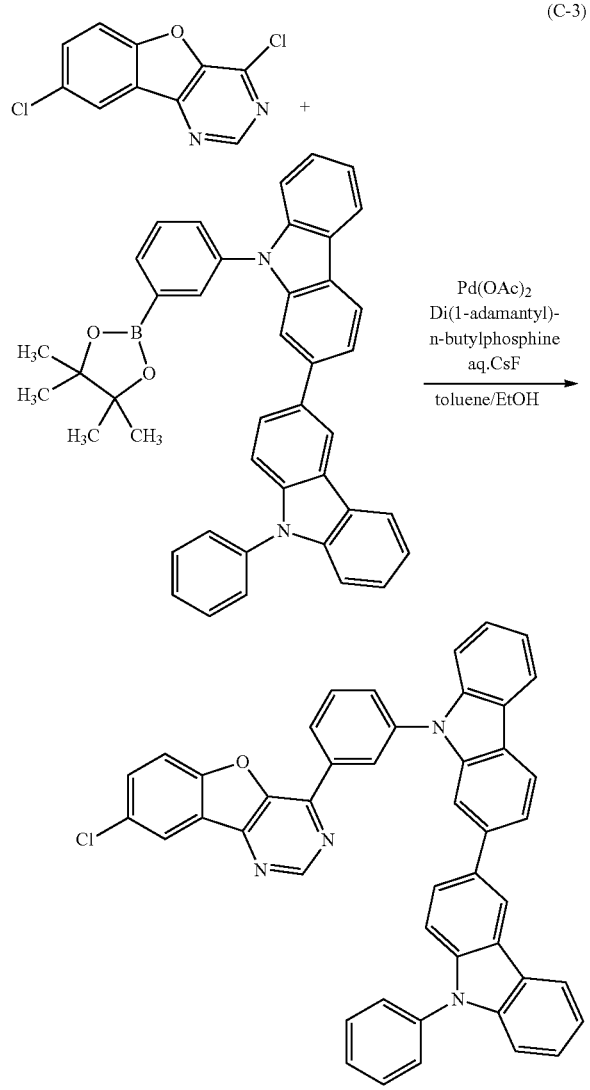

(C-3)

Step 4: Synthesis of 8-(9H-carbazol-9-yl)-4-[3-(9'-phenyl-2,3'-bi-9H-carbazol-9-yl)phenyl]benzofuro[3,2-d]pyrimidine (abbreviation: 8Cz-4mPCCzPBfpm)

Into a 200-mL three-neck flask, 2.9 g of 8-chloro-4-[3-(9'-phenyl-2,3'-bi-9H-carbazol-9-yl)phenyl]benzofuro[3,2-d]pyrimidine obtained in Step 3, 0.84 g of 9H-carbazole, 0.97 g of sodium tert-butoxide, and 100 mL of mesitylene were put, and the air in the flask was replaced with nitrogen. Then, 59 mg of di-tert-butyl(1-methyl-2,2-diphenylcyclopropyl)phosphine (abbreviation: cBRIDP) and 15 mg of allylpalladium(II)chloride dimer were added thereto, and the mixture was heated under a nitrogen stream at 160° C. for 21 hours. Water was added to the obtained reaction mixture and the mixture was filtered. The filtrate was extracted with toluene, the solution of the extract was washed with saturated saline, magnesium sulfate was added, and then filtration was performed. The solvent of the filtrate was distilled off. The obtained reaction mixture was purified by silica gel column chromatography. First, only toluene was in a developing solvent. Purification was performed by gradually increasing the proportion of ethyl acetate until the ratio of toluene to ethyl acetate became 1:10 in the developing solvent. The solvent of the obtained fraction was distilled off and the obtained solid was recrystallized with a mixed solvent of toluene and hexane, whereby 1.0 g of a target pale yellow solid of 8Cz-4mPCCzPBfpm was obtained in a yield of 29%. The synthesis scheme of Step 4 is shown in (C-4) below.

(C-4)

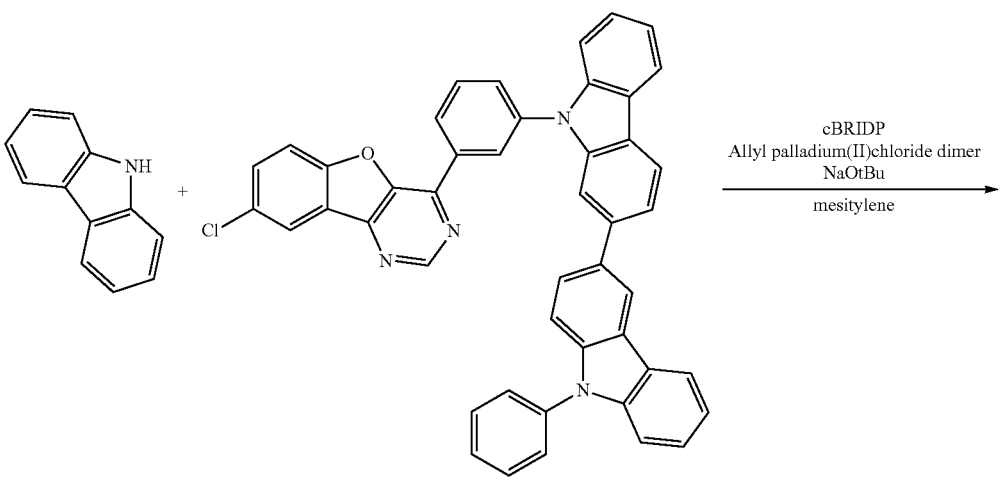

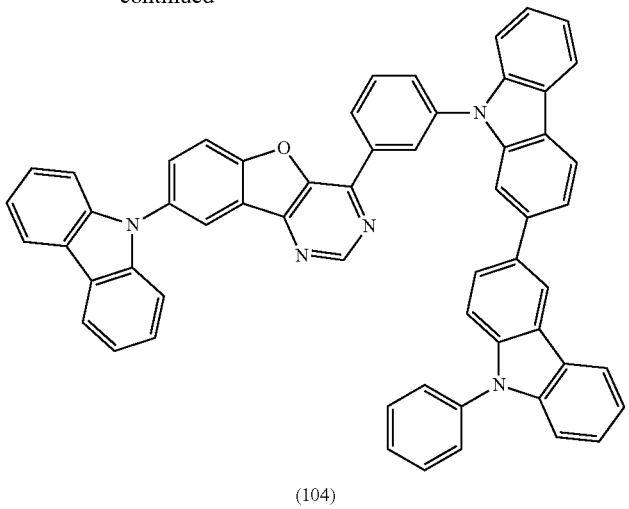

(104)

Then, 1.0 g of the obtained pale yellow solid was purified by a train sublimation method. In the purification by sublimation, the pale yellow solid was heated at 380° C. under a pressure of 2.3 Pa with a flow rate of an argon gas of 10 mL/min. After the purification by sublimation, 0.77 g of a target yellow solid was obtained at a collection rate of 76%.

The obtained solid was subjected to nuclear magnetic resonance spectrometry ($^1$H NMR), and the results are shown below.

$^1$H-NMR δ(TCE-$d_2$): 7.22-7.25 (dt, 1H), 7.30-7.32 (m, 4H), 7.37-7.56 (m, 12H), 7.62 (dd, 2H), 7.67 (dd, 1H), 7.74-7.78 (dt, 2H), 7.93-7.97 (m, 3H), 8.07 (d, 1H), 8.15 (d, 2H), 8.23 (d, 1H), 8.29 (d, 1H), 8.43 (dd, 1H), 8.72 (td, 1H), 8.95 (s, 1H), 9.32 (s, 1H).

Figure 22A:
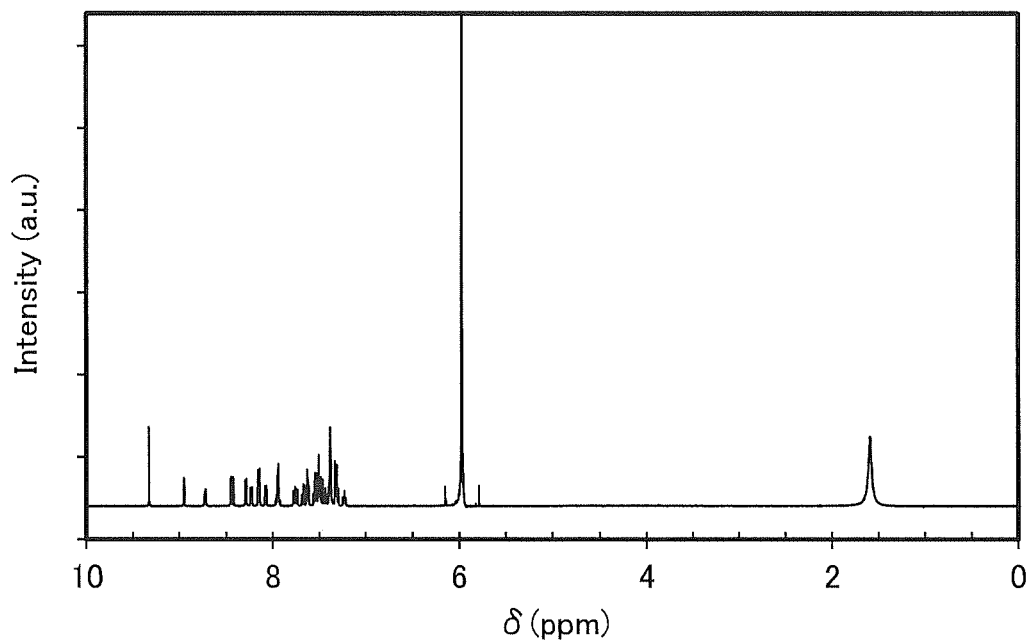
FIGS. 22A and 22B show NMR charts of a compound in Example.
Figure 22B:
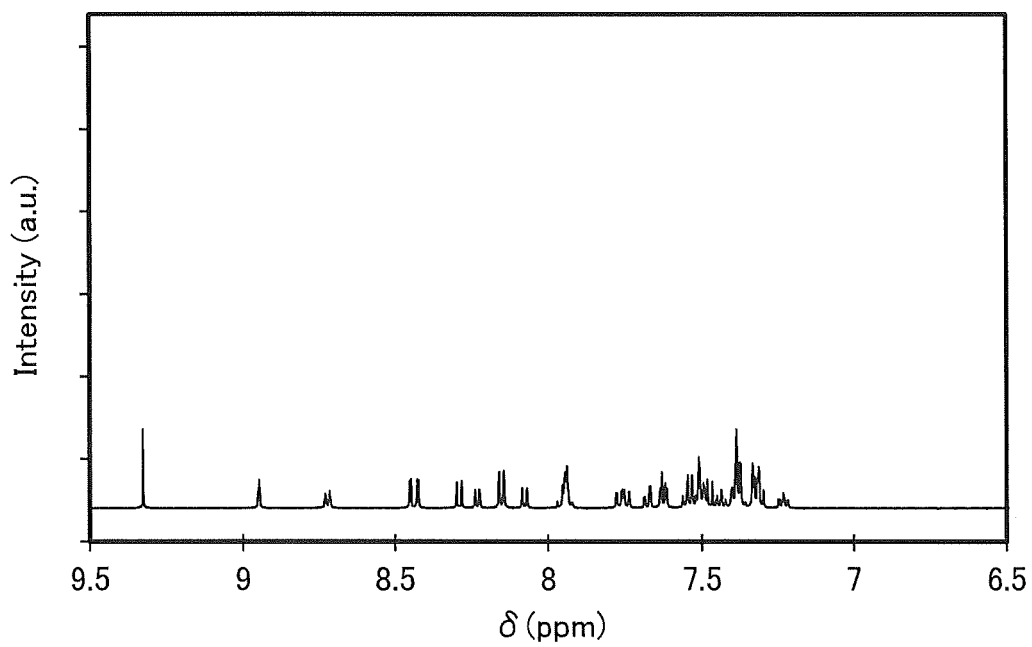

FIGS. 22A and 22B are $^1$H NMR charts of the obtained solid. Note that FIG. 22B is a chart showing an enlarged part in the range of 6.5 ppm to 9.5 ppm of FIG. 22A. The results revealed that 4Ph-2,8mDBtP2Bfpm, which was the target substance, was obtained.

<Characteristics of 8Cz-4mPCCzPBfpm>

Figure 23:
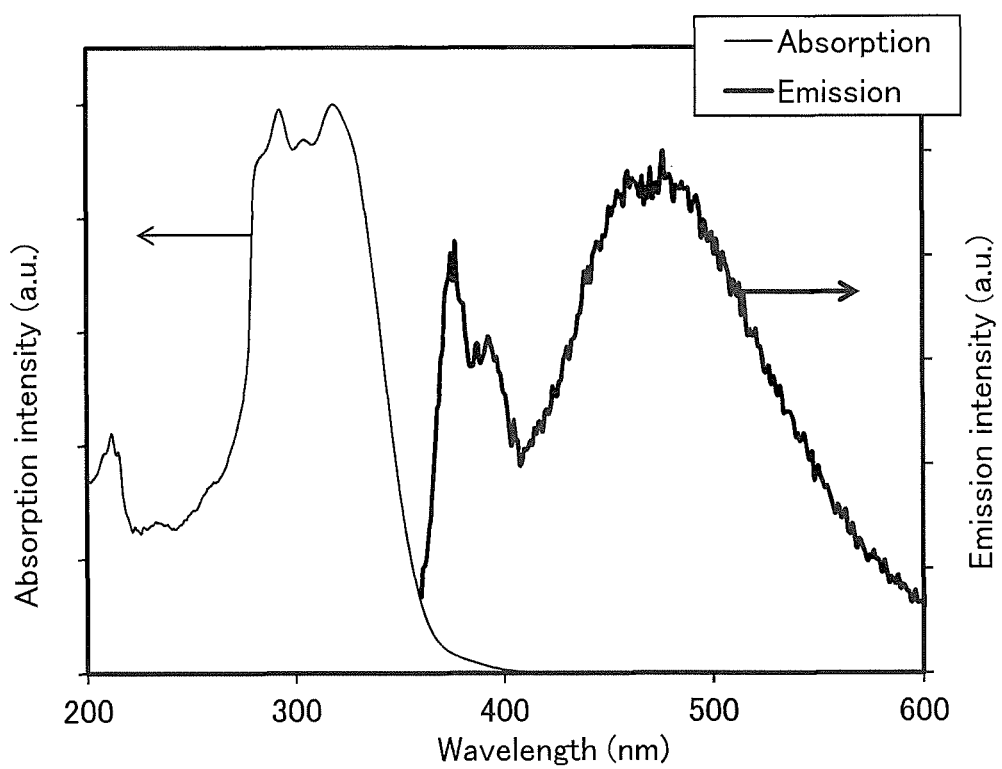
FIG. 23 shows absorption and emission spectra of a compound in Example.

Absorption and emission spectra of 8Cz-4mPCCzPBfpm in a toluene solution are shown in FIG. 23. The horizontal axis represents wavelength and the vertical axes represent absorption intensity and emission intensity. The measurement method was the same as that described in the above example.

As shown in FIG. 23, the absorption peak wavelengths of 8Cz-4mPCCzPBfpm in the toluene solution were around 292 nm, 303 nm, and 323 nm, and the emission peak wavelengths thereof were around 371 nm and 477 nm (an excitation wavelength of 341 nm).

Figure 24:
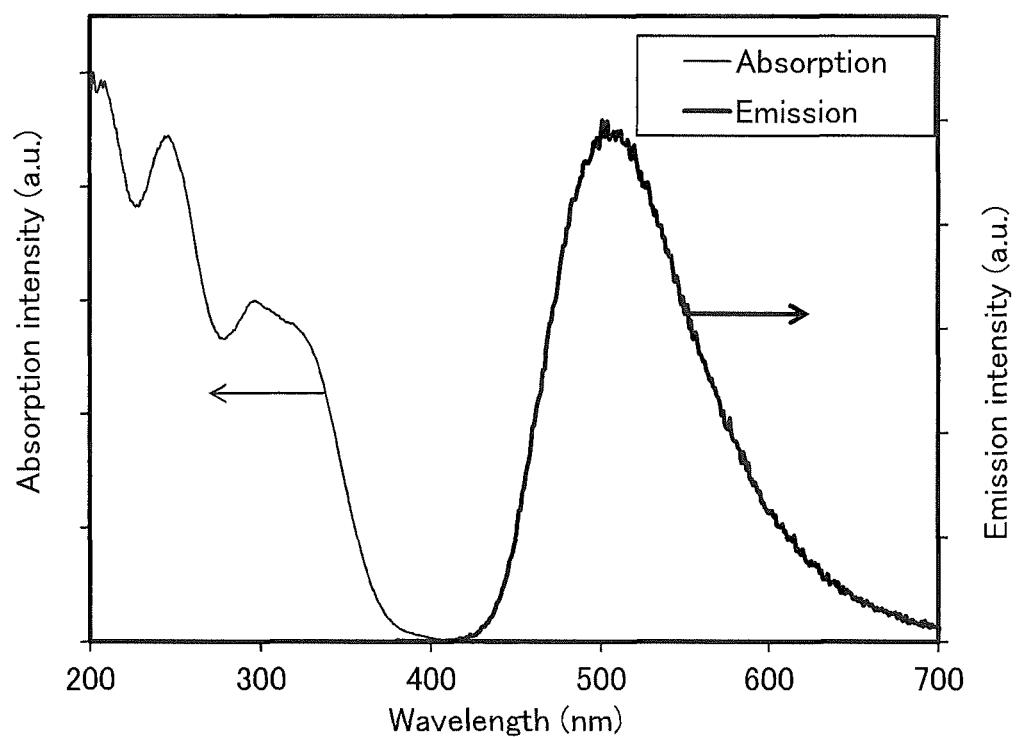
FIG. 24 shows absorption and emission spectra of a compound in Example.

Next, absorption and emission spectra of a solid thin film of 8Cz-4mPCCzPBfpm were measured. The solid thin film was formed over a quartz substrate by a vacuum evaporation method. The absorption spectrum of the thin film was calculated using an absorbance ($-\log_{10}$ [% T/(100−% R)]) obtained from a transmittance and a reflectance of a substrate and the thin film. Note that % T represents transmittance and % R represents reflectance. The absorption spectrum was measured using a UV-visible spectrophotometer (U-4100, manufactured by Hitachi High-Technologies Corporation). The emission spectrum was measured using a fluorescence spectrophotometer (FS920, manufactured by Hamamatsu Photonics K.K.). FIG. 24 shows the measurement results of the obtained absorption and emission spectra of the solid thin film. The horizontal axis represents wavelength and the vertical axes represent absorption intensity and emission intensity.

According to the measurement results in FIG. 24, the absorption peak wavelengths of the solid thin film of 8Cz-4mPCCzPBfpm were around 206 nm, 246 nm, 297 nm, and 332 nm, and the emission peak wavelength thereof was around 507 nm (an excitation wavelength of 370 nm).

Example 5

In this example, fabrication examples of light-emitting elements, which are different from the light-emitting elements described in Example 3, each including the organic compound of one embodiment of the present invention and characteristics of the light-emitting elements are described. A comparative light-emitting element 3 was also fabricated. A cross-sectional view of the structure of each of the elements fabricated in this example is similar to that in FIG. 1A. Table 3 shows details of the element structure. In addition, structures and abbreviations of compounds used here are given below. Note that the above example can be referred to for other organic compounds.

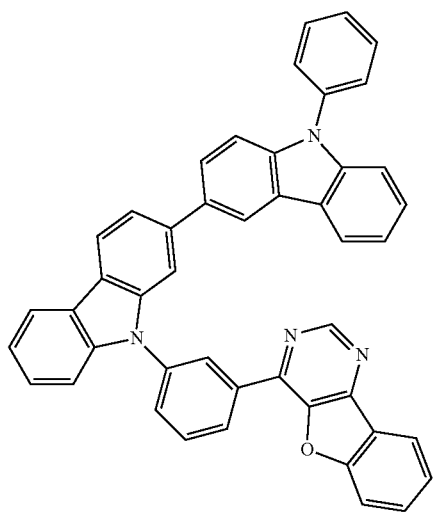

(4mPCCzPBfpm-02)

-continued

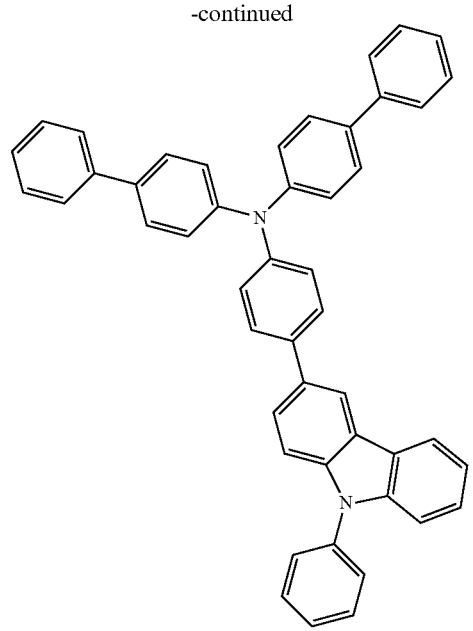

(PCBBi1BP)

TABLE 3

| | Layer | Reference numeral | Thickness (nm) | Material | Weight ratio |
|---|---|---|---|---|---|
| Comparative light-emitting element 3 | Electrode | 102 | 200 | Al | — |
| | Electron-injection layer | 119 | 1 | LiF | — |
| | Electron-transport layer | 118(2) | 15 | Bphen | — |
| | | 118(1) | 20 | 4mPCCzPBfpm-02 | — |
| | Light-emitting layer | 130 | 40 | 4mPCCzPBfpm-02:PCCP:GD270 | 0.5:0.5:0.1 |
| | Hole-transport layer | 112 | 20 | PCBBi1BP | — |
| | Hole-injection layer | 111 | 45 | DBT3P-II:MoO$_3$ | 1:0.5 |
| | Electrode | 101 | 70 | ITSO | — |
| Light-emitting element 4 | Electrode | 102 | 200 | Al | — |
| | Electron-injection layer | 119 | 1 | LiF | — |
| | Electron-transport layer | 118(2) | 15 | Bphen | — |
| | | 118(1) | 20 | 8Cz-4PCCzBfpm-02 | — |
| | Light-emitting layer | 130 | 40 | 8Cz-4PCCzBfpm-02:PCCP:GD270 | 0.5:0.5:0.1 |
| | Hole-transport layer | 112 | 20 | PCBBi1BP | — |
| | Hole-injection layer | 111 | 45 | DBT3P-II:MoO$_3$ | 1:0.5 |
| | Electrode | 101 | 70 | ITSO | — |
| Light-emitting element 5 | Electrode | 102 | 200 | Al | — |
| | Electron-injection layer | 119 | 1 | LiF | — |
| | Electron-transport layer | 118(2) | 15 | Bphen | — |
| | | 118(1) | 20 | 8Cz-4mPCCzPBfpm | — |
| | Light-emitting layer | 130 | 40 | 8Cz-4mPCCzPBfpm:PCCP:GD270 | 0.5:0.5:0.1 |
| | Hole-transport layer | 112 | 20 | PCBBi1BP | — |
| | Hole-injection layer | 111 | 45 | DBT3P-II:MoO$_3$ | 1:0.5 |
| | Electrode | 101 | 70 | ITSO | — |

<<Fabrication of Comparative Light-Emitting Element 3>>

As the electrode 101, an ITSO film was formed to a thickness of 70 nm over the substrate 200. The electrode area of the electrode 101 was set to 4 mm² (2 mm×2 mm).

As the hole-injection layer 111, 4,4',4''-(benzene-1,3,5-triyl)tri(dibenzothiophene) (abbreviation: DBT3P-II) and molybdenum oxide (MoO₃) were deposited over the electrode 101 by co-evaporation in a weight ratio of DBT3P-II:MoO₃=1:0.5 to a thickness of 45 nm.

As the hole-transport layer 112, 4,4'-diphenyl-4''-(9-phenyl-9H-carbazol-3-yl)triphenylamine (abbreviation: PCBBi1BP) was deposited over the hole-injection layer 111 by evaporation to a thickness of 20 nm.

As the light-emitting layer 130 over the hole-transport layer 112, 4-[3-(9'-phenyl-2,3'-bi-9H-carbazol-9-yl)phenyl]benzofuro[3,2-d]pyrimidine (abbreviation: 4mPCCzPBfpm-02), PCCP, and GD270 (manufactured by Jilin Optical and Electronic Materials Co., Ltd.) were deposited by co-evaporation in a weight ratio of 4mPCCzPBfpm-02:PCCP:GD270=0.5:0.5:0.1 to a thickness of 40 nm. Note that in the light-emitting layer 130, GD270 corresponds to the guest material that emits phosphorescence.

As the electron-transport layer 118, 4mPCCzPBfpm-02 and BPhen were sequentially deposited by evaporation to thicknesses of 20 nm and 15 nm, respectively, over the light-emitting layer 130. Then, as the electron-injection layer 119, LiF was deposited over the electron-transport layer 118 by evaporation to a thickness of 1 nm.

As the electrode 102, aluminum (Al) was deposited over the electron-injection layer 119 to a thickness of 200 nm.

Next, in a glove box containing a nitrogen atmosphere, the comparative light-emitting element 3 was sealed by fixing the substrate 220 to the substrate 200 over which the organic material was deposited using a sealant for an organic EL device. Specifically, after the sealant was applied to surround the organic material over the substrate 200 and the substrate 200 was bonded to the substrate 220, irradiation with ultraviolet light having a wavelength of 365 nm at 6 J/cm² and heat treatment at 80° C. for one hour were performed. Through the process, the comparative light-emitting element 3 was obtained.

<<Fabrication of Light-Emitting Element 4>>

A light-emitting element 4 was fabricated through the same steps as those for the comparative light-emitting element 3 except for the steps of forming the light-emitting layer 130 and the electron-transport layer 118.

As the light-emitting layer 130 over the hole-transport layer 112, 8Cz-4PCCzBfpm-02, PCCP, and GD270 (manufactured by Jilin Optical and Electronic Materials Co., Ltd.) were deposited by co-evaporation in a weight ratio of 8Cz-4PCCzBfpm-02:PCCP:GD270=0.5:0.5:0.1 to a thickness of 40 nm. Note that in the light-emitting layer 130, GD270 corresponds to the guest material that emits phosphorescence.

As the electron-transport layer 118, 8Cz-4PCCzBfpm-02 and BPhen were sequentially deposited by evaporation to thicknesses of 20 nm and 15 nm, respectively, over the light-emitting layer 130.

<<Fabrication of Light-Emitting Element 5>>

A light-emitting element 5 was fabricated through the same steps as those for the comparative light-emitting element 3 except for the steps of forming the light-emitting layer 130 and the electron-transport layer 118.

As the light-emitting layer 130 over the hole-transport layer 112, 8Cz-4mPCCzPBfpm, PCCP, and GD270 (manufactured by Jilin Optical and Electronic Materials Co., Ltd.) were deposited by co-evaporation in a weight ratio of 8Cz-4mPCCzPBfpm:PCCP:GD270=0.5:0.5:0.1 to a thickness of 40 nm. Note that in the light-emitting layer 130, GD270 corresponds to the guest material that emits phosphorescence.

As the electron-transport layer 118, 8Cz-4mPCCzPBfpm and BPhen were sequentially deposited by evaporation to thicknesses of 20 nm and 15 nm, respectively, over the light-emitting layer 130.

<Characteristics of Light-Emitting Elements>

Figure 25:
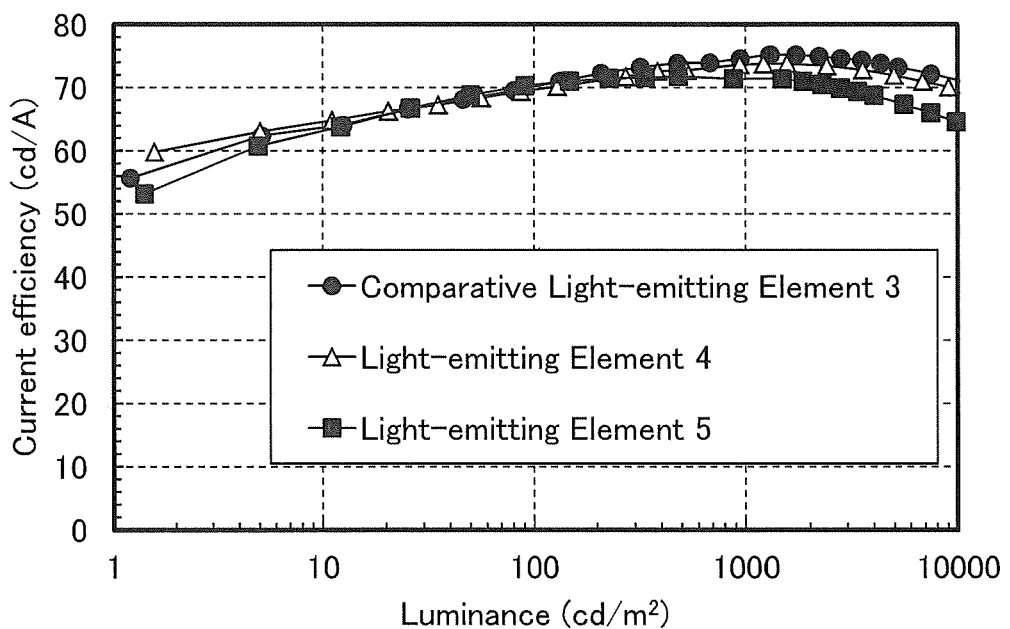
FIG. 25 shows current efficiency-luminance characteristics of light-emitting elements in Example.
Figure 26:
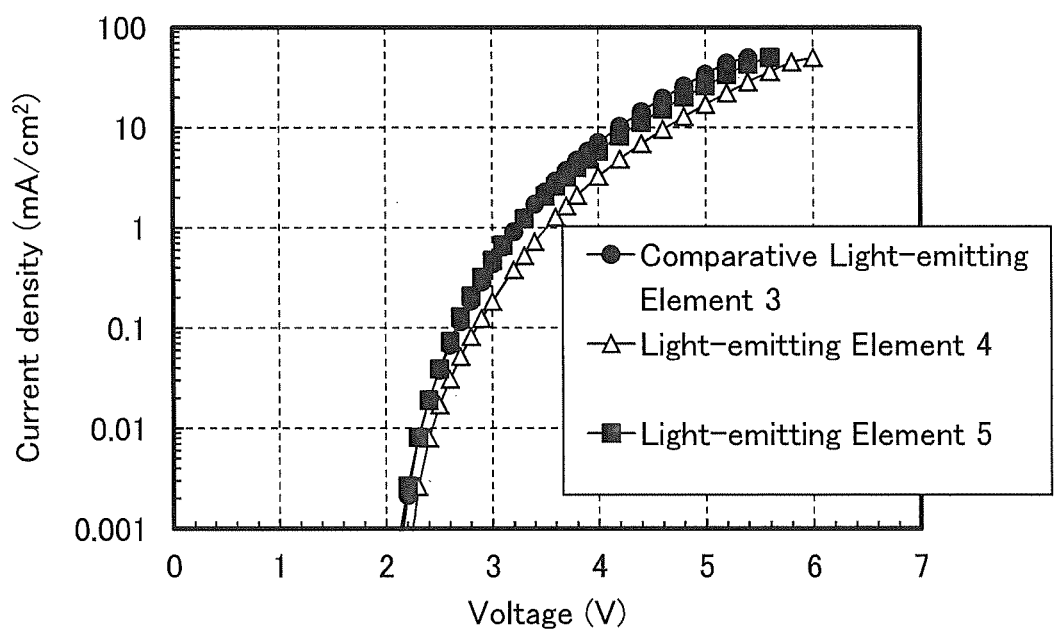
FIG. 26 shows current density-voltage characteristics of light-emitting elements in Example.
Figure 27:
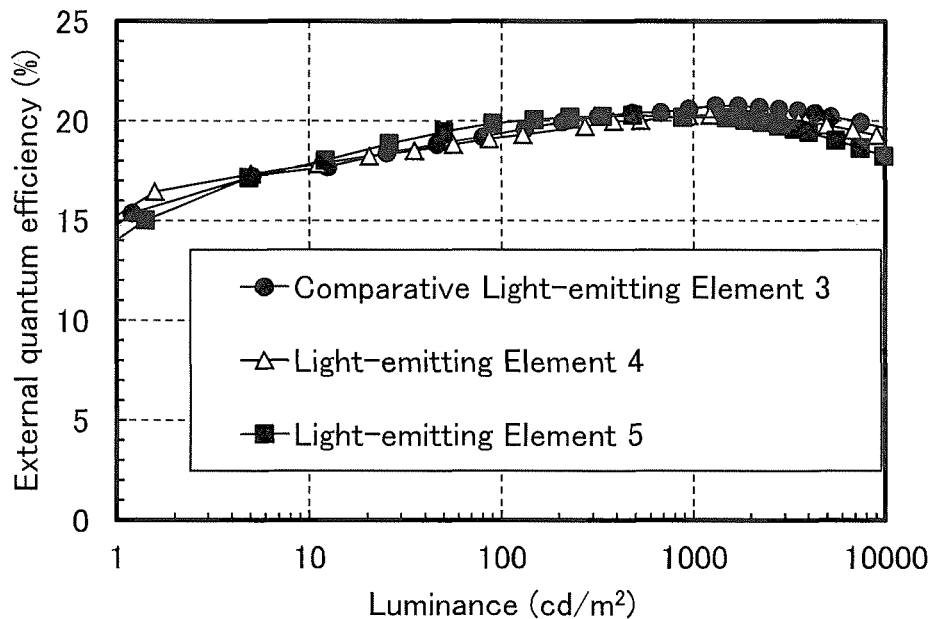
FIG. 27 shows external quantum efficiency-luminance characteristics of light-emitting elements in Example.
Figure 28:
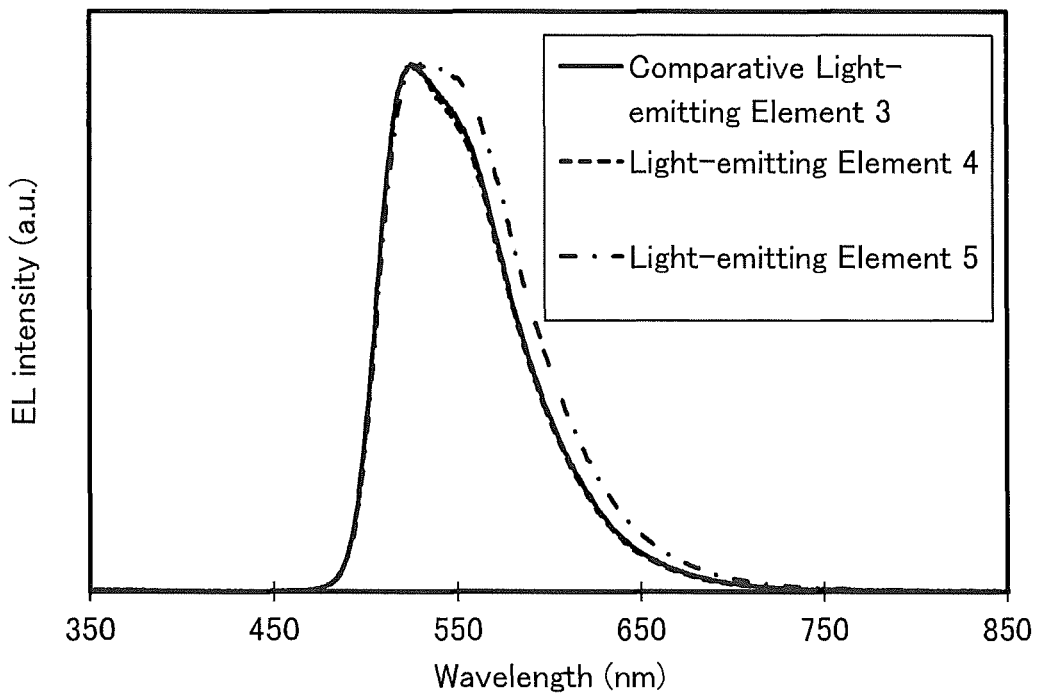
FIG. 28 shows emission spectra of light-emitting elements in Example.

The current efficiency-luminance characteristics of the fabricated comparative light-emitting element 3 and the fabricated light-emitting elements 4 and 5 are shown in FIG. 25. The current density-voltage characteristics thereof are shown in FIG. 26. The external quantum efficiency-luminance characteristics thereof are shown in FIG. 27. The measurements of the light-emitting elements were performed at room temperature (in an atmosphere kept at 23° C.). FIG. 28 shows the electroluminescence spectra obtained when a current at a current density of 2.5 mA/cm² was supplied to the comparative light-emitting element 3 and the light-emitting elements 4 and 5. The measurements were performed at room temperature.

Table 4 shows element characteristics of the comparative light-emitting element 3 and the light-emitting elements 4 and 5 at around 1000 cd/m².

TABLE 4

|  | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Comparative light-emitting element 3 | 3.3 | 1.3 | (0.35, 0.62) | 950 | 75 | 71 | 21 |
| Light-emitting element 4 | 3.6 | 1.3 | (0.35, 0.62) | 940 | 74 | 64 | 20 |
| Light-emitting element 5 | 3.3 | 1.2 | (0.37, 0.60) | 880 | 71 | 68 | 20 |

As shown in FIG. 25 to FIG. 27 and Table 4, the comparative light-emitting element 3 and the light-emitting elements 4 and 5 exhibited high current efficiency and high external quantum efficiency which are equivalent to each other. In addition, a fall (roll-off) in the current efficiency and the external quantum efficiency of the comparative light-emitting element 3 and the light-emitting elements 4 and 5 was small even on the high luminance side, which is excellent. Similarly, the comparative light-emitting element 3 and the light-emitting elements 4 and 5 exhibited high driving voltages which are equivalent to each other.

As shown in FIG. 28, the comparative light-emitting element 3 and the light-emitting elements 4 and 5 emitted green light having electroluminescence spectra with peaks at wavelengths of 525 nm, 525 nm, and 530 nm, respectively, and full widths at half maximum of 80 nm, 78 nm, and 88 nm, respectively. The obtained electroluminescence spectrum reveals that light is emitted from GD270 as the guest material.

<Reliability of Light-Emitting Elements>

Figure 29:
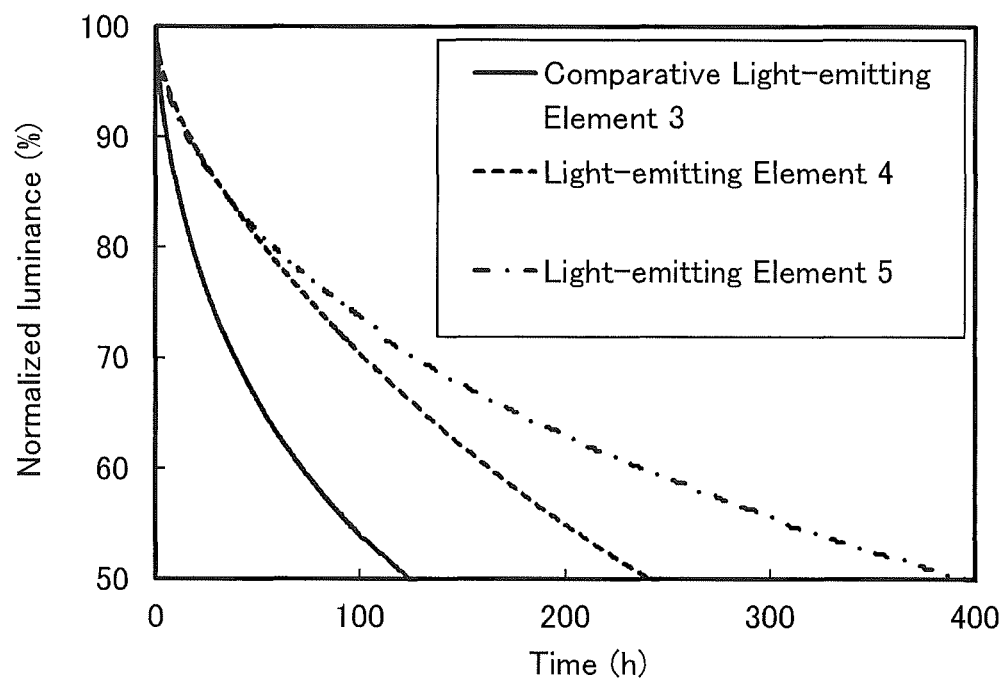
FIG. 29 shows reliability test results of light-emitting elements in Example.

Next, driving tests at a constant current of 2 mA were performed on the comparative light-emitting element 3 and the light-emitting elements 4 and 5. The results are shown in FIG. 29. As shown in FIG. 29, the reliability of the light-emitting elements 4 and 5 was improved more than that of the comparative light-emitting element 3. Accordingly, it is suggested that an organic compound including a condensed ring in the 6-, 7-, 8-, or 9-position of a benzofuro[3,2-d] pyrimidine skeleton has higher reliability than an organic compound not including a condensed ring in the 6-, 7-, 8-, or 9-position of a benzofuro[3,2-d]pyrimidine skeleton. Furthermore, it was found that the light-emitting element 5 had higher reliability than the light-emitting element 4. Thus, it is suggested that the structure in which a carbazole skeleton, which is a hole-transport skeleton, is bonded to the 4-position of a benzofuro[3,2-d]pyrimidine skeleton through a phenyl group, which is one of aryl groups, has higher reliability than the structure in which a carbazole skeleton is directly bonded to the 4-position of a benzofuro[3,2-d] pyrimidine skeleton.

This application is based on Japanese Patent Application Serial No. 2016-250190 filed with Japan Patent Office on Dec. 23, 2016, the entire contents of which are hereby incorporated by reference.

What is claimed is:

1. An organic compound represented by General Formula (G0):

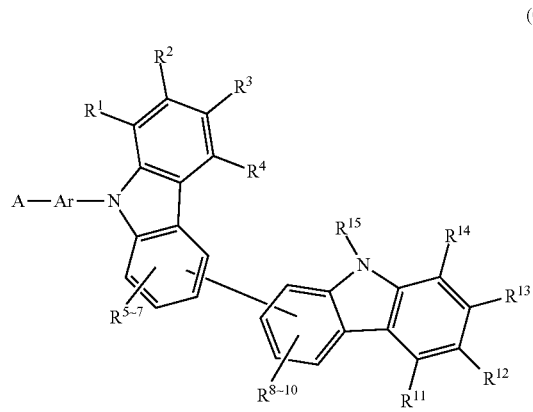

(G0)

wherein A represents a substituted or unsubstituted benzofuro[3,2-d]pyrimidine skeleton having a carbazole ring as a substituent; each of $R^1$ to $R^{15}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms;

and Ar represents a substituted or unsubstituted arylene group having 6 to 25 carbon atoms, or a single bond.

2. The organic compound according to claim 1, wherein the Ar is bonded to a 4-position of the benzofuro[3,2-d] pyrimidine skeleton.

3. The organic compound according to claim 1, the organic compound is represented by General Formula (G1):

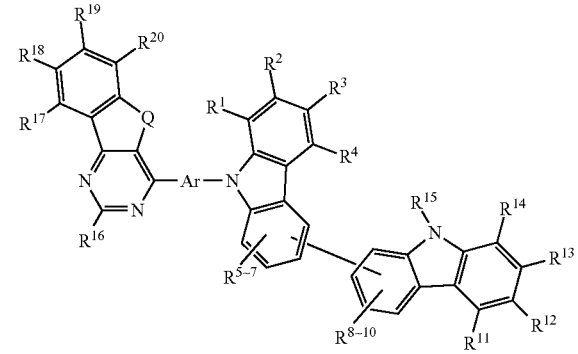

(G1)

wherein Q represents oxygen; any one of $R^{16}$ to $R^{20}$ represents a substituent having a carbazole ring as a substituent and each of the others independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms.

4. An organic compound represented by General Formula (G2):

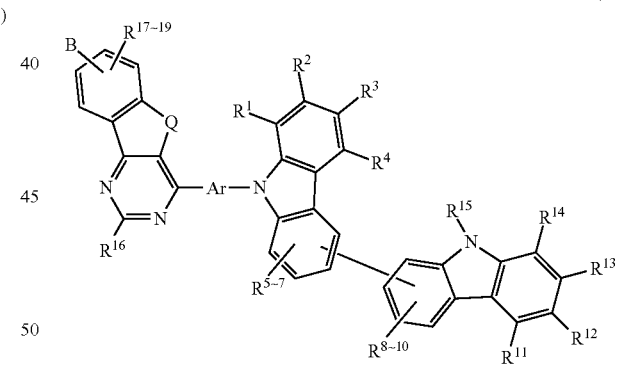

(G2)

wherein Q represents oxygen; each of $R^1$ to $R^{19}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms; Ar represents a substituted or unsubstituted arylene group having 6 to 25 carbon atoms, or a single bond; and B represents a substituent having a carbazole ring as a substituent.

5. The organic compound according to claim 4, the organic compound is represented by General Formula (G3):

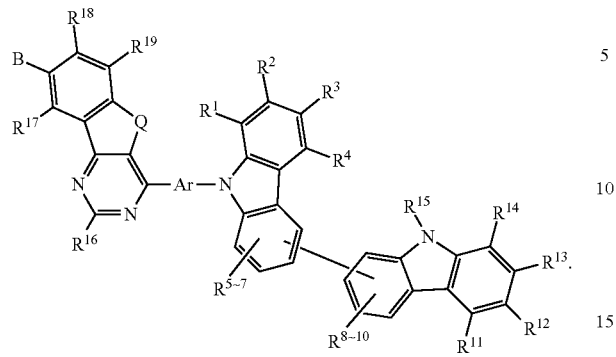
(G3)
6. The organic compound according to claim 5, the organic compound is represented by General Formula (G4):
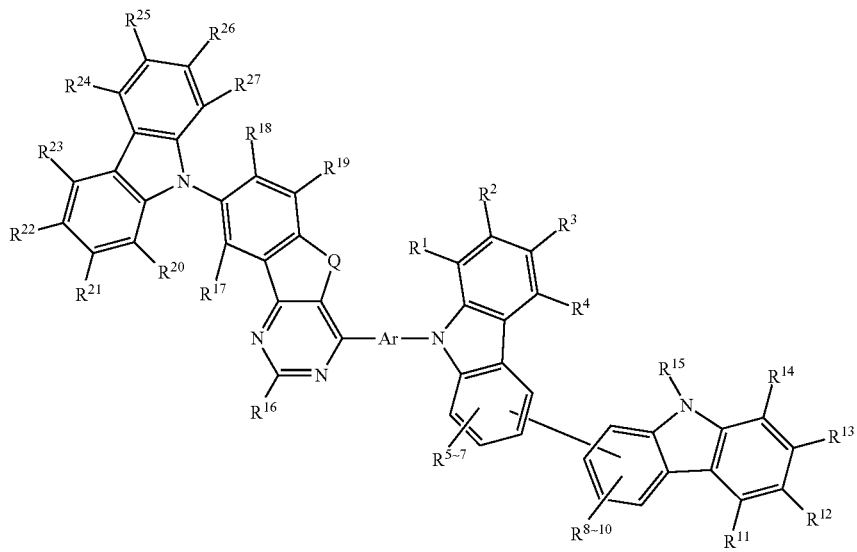
(G4)
wherein each of $R^{20}$ to $R^{27}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

7. The organic compound according to claim 6, the organic compound is represented by General Formula (G6):

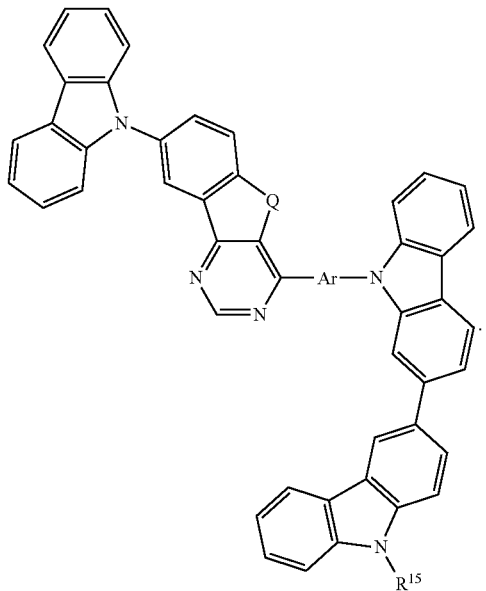

(G6)

8. A light-emitting element comprising:
a pair of electrode; and
a layer provided between the pair of electrode, the layer comprises an organic compound represented by General Formula (G0),

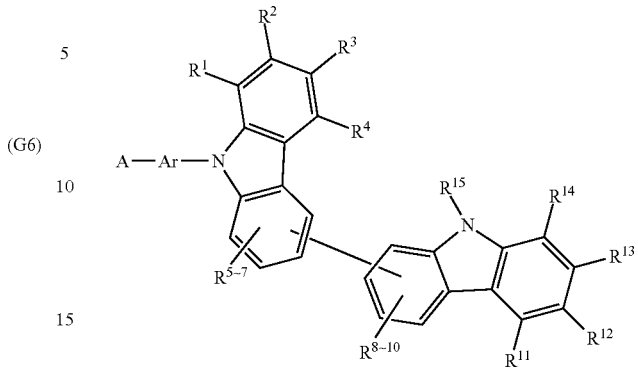

(G0)

wherein A represents a substituted or unsubstituted benzofuro[3,2-d]pyrimidine skeleton having a carbazole ring as a substituent; each of $R^1$ to $R^{15}$ independently represents any of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms;

and Ar represents a substituted or unsubstituted arylene group having 6 to 25 carbon atoms, or a single bond.

9. The light-emitting element according to claim 8, wherein the Ar is bonded to a 4-position of the benzofuro[3,2-d]pyrimidine skeleton.

10. The light-emitting element according to claim 8, the light-emitting element is configured to emit light containing a component including delayed fluorescence.

11. The light-emitting element according to claim 8, further comprising a phosphorescent material.

12. A light-emitting device comprising:
a light-emitting portion comprising the light-emitting element according to claim 8; and
a substrate.

* * * * *